United States Patent
Li et al.

(10) Patent No.: US 12,037,541 B2
(45) Date of Patent: Jul. 16, 2024

(54) ANIONIC-CATIONIC-NONIONIC SURFACTANT, PRODUCTION AND USE THEREOF

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Yingcheng Li, Shanghai (CN); Songyuan Gu, Shanghai (CN); Weidong Zhang, Shanghai (CN); Xinning Bao, Shanghai (CN); Ou Sha, Shanghai (CN); Zhiqin Shen, Shanghai (CN); Yiqing Yang, Shanghai (CN); Xiaodong Zhai, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 0 days.

(21) Appl. No.: 17/451,086

(22) Filed: Oct. 15, 2021

(65) Prior Publication Data
US 2022/0033705 A1    Feb. 3, 2022

Related U.S. Application Data

(60) Division of application No. 16/509,057, filed on Jul. 11, 2019, now Pat. No. 11,186,764, which is a continuation of application No. 15/520,377, filed as application No. PCT/CN2014/000939 on Oct. 22, 2014, now Pat. No. 10,400,156.

(51) Int. Cl.
| | |
|---|---|
| C09K 8/584 | (2006.01) |
| C07C 213/06 | (2006.01) |
| C07C 217/08 | (2006.01) |
| C07C 231/14 | (2006.01) |
| C07C 233/05 | (2006.01) |
| C07C 233/09 | (2006.01) |
| C07C 233/36 | (2006.01) |
| C07C 237/08 | (2006.01) |
| C07C 237/40 | (2006.01) |
| C07C 303/22 | (2006.01) |
| C07C 309/10 | (2006.01) |
| C09K 8/60 | (2006.01) |

(52) U.S. Cl.
CPC ............ *C09K 8/584* (2013.01); *C07C 213/06* (2013.01); *C07C 217/08* (2013.01); *C07C 231/14* (2013.01); *C07C 233/05* (2013.01); *C07C 233/09* (2013.01); *C07C 233/36* (2013.01); *C07C 237/08* (2013.01); *C07C 237/40* (2013.01); *C07C 303/22* (2013.01); *C07C 309/10* (2013.01); *C09K 8/602* (2013.01)

(58) Field of Classification Search
CPC ....... C09K 8/584; C09K 8/602; C07C 211/00; C07C 217/08; C07C 237/08; C07C 309/10; E21B 43/20
See application file for complete search history.

(56) References Cited

U.S. PATENT DOCUMENTS

| | | | | |
|---|---|---|---|---|
| 3,684,427 A | * | 8/1972 | Walz ..................... | D06P 1/6076 8/590 |
| 3,925,262 A | * | 12/1975 | Laughlin ................. | C11D 1/88 510/345 |
| 4,159,277 A | * | 6/1979 | Gosselink ............. | C07C 305/10 558/45 |
| 4,895,667 A | * | 1/1990 | Fox ........................ | C11D 1/645 510/515 |

(Continued)

FOREIGN PATENT DOCUMENTS

| | | |
|---|---|---|
| CN | 102161883 A | 8/2011 |
| CN | 103740354 A | 4/2014 |

(Continued)

OTHER PUBLICATIONS

Gong, Yuj-Un et al. "The solubilization of catanionic surfactants mixture", Journal of Northwest Univeristy (National Science edition), vol. 30 No. 1, p. 28-31 (2000), Department of Chemistry, Yanan University, Yanan 716000, China (Abstract at the bottom).

(Continued)

*Primary Examiner* — Aiqun Li
(74) *Attorney, Agent, or Firm* — NKL Law; Allen Xue

(57) ABSTRACT

An anionic-cationic-nonionic surfactant represented by the formula (I)

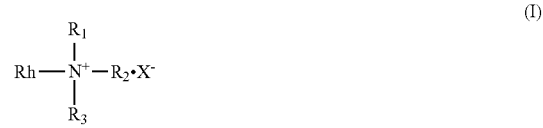

exhibits significantly improved interfacial activity and stability as compared with the prior art. With the present anionic-cationic-nonionic surfactant, a flooding fluid composition for tertiary oil recovery with improved oil displacement efficiency and oil washing capability as compared with the prior art could be produced.

7 Claims, No Drawings

(56) References Cited

U.S. PATENT DOCUMENTS

| | | | |
|---|---|---|---|
| 5,424,445 A | 6/1995 | Hendrick ter Maat et al. | |
| 5,879,561 A | 3/1999 | Klomp et al. | |
| 5,922,663 A * | 7/1999 | Gabriel | C09K 23/00 510/528 |
| 6,503,413 B2 | 1/2003 | Uchiyama et al. | |
| 8,309,759 B2 | 11/2012 | Baumann et al. | |

FOREIGN PATENT DOCUMENTS

| | | |
|---|---|---|
| CN | 103965853 A | 8/2014 |
| CN | 103967462 A | 8/2014 |
| RU | 2478777 C1 | 4/2013 |
| RU | 2266300 C2 | 12/2015 |
| WO | 2011110502 A1 | 9/2011 |
| WO | 2011130310 A1 | 10/2011 |

OTHER PUBLICATIONS

Huang, Hungdu et al. "Synergistic effect of Oil-displacing Surfactant with Non-ionic Surfactant and Cationic Surfactant", Journal of Oil and Gas Technology, vol. 29, No. 4, p. 101-104 (2007).

* cited by examiner

ANIONIC-CATIONIC-NONIONIC SURFACTANT, PRODUCTION AND USE THEREOF

CROSS-REFERENCE TO RELATED APPLICATIONS

This application is a divisional application of U.S. application Ser. No. 16/509,057, filed Jul. 11, 2019, which is a continuation application of U.S. application Ser. No. 15/520,377, filed Apr. 19, 2017 (now U.S. Pat. No. 10,400,156, issued Sep. 3, 2019), which is a national-stage application under 35 USC § 371 of PCT/CN2014/000939, filed on Oct. 22, 2014, the contents of which are incorporated herein by reference in their entirety.

TECHNICAL FIELD

This invention relates to an anionic-cationic-nonionic surfactant. Specifically, this invention relates to an anionic-cationic-nonionic surfactant for tertiary oil recovery, production and use thereof in tertiary oil recovery.

BACKGROUND ART

With the increase in world energy demand, rational development and utilization of crude oil has caused more and more attention, the demand on crude oil output and recovery efficiency are also getting higher and higher. The conventional (primary or secondary) crude oil recovery process generally extracts only ⅓ of the geological crude oil reserves, with about ⅔ thereof failing to be extracted. Therefore, with the increasing tense in energy consumption, enhanced oil recovery has become an important topic in the research of crude oil recovery.

The tertiary oil recovery technology is an effective process for enhanced oil recovery. Specifically, among tertiary oil recovery technologies, the chemical enhanced oil recovery (CEOR) technology represents a very important and large-scale implemented technology, including the polymer flooding technology, the surfactant flooding technology, the alkali water flooding technology and a combination thereof. The CEOR technology makes use of the combination of a physical and chemical effects, wherein the chemical action mainly resides in reducing the interfacial tension between a flooding fluid and crude oil. A surfactant contains both lipophilic (hydrophobic) and hydrophilic (lipophobic) segments, when dissolved into water, mainly adsorbed at the oil-water interface, whereby significantly reducing the oil-water interfacial tension (IFT). The reduction in the oil-water interfacial tension leads to the increase of capillary number, which will help the passing of crude oil through a pore throat. The flooding function observed with a surfactant is further indicated by the effects like alteration in the surface wettability of oleophylic rock, emulsification of crude oil, increment of the surface charge density and oil droplet coalescence, all of which explain why the surfactant has been identified as a critical component in a flooding fluid.

However, the prior art flooding fluid for tertiary oil recovery suffers from such problems as poor interfacial activity of the surfactant component, leading to a relatively lower oil displacement efficiency for the flooding fluid produced therefrom, an over-complicated composition with the flooding fluid, which makes difficult the demulsification of the recovered liquid and the treatment of produced water; necessarily containing an inorganic alkali, which is harmful to the reservoir and oil wells, leading to corrosion of equipments and pipings. Further, an inorganic alkali will significantly decrease the viscosity of a polymer component, then a relatively higher amount of polymer has to be used to achieve a predetermined level of viscosity, which increases the overall cost of oil recovery. The prior art surfactant component is insufficient in the tolerance to elevated temperatures, and the tolerance to high salinity and high total dissolved salt (TDS), and tends to generate precipitation during compounding due to its poor stability.

Therefore, there is still a need for a surfactant, which is deprived of the problems in association with the prior arts, and shows improved interfacial activity and stability as compared with the prior arts.

INVENTION SUMMARY

The present inventors, on the basis of the prior art, found a novel anionic-cationic-nonionic surfactant, and further found that, when a flooding fluid composition for tertiary oil recovery (i.e. a flooding fluid) is produced with this anionic-cationic-nonionic surfactant, the aforesaid problems in association with the prior art can be solved, and then this invention is achieved.

Specifically, this invention relates to the following aspects. 1. An anionic-cationic-nonionic surfactant, representing one or more selected from the group consisting of compounds as substantially represented by the formula (I),

in the formula (I), the group $N^+$ represents a quaternary nitrogen cation; the groups $R_1$ to $R_3$ may be identical with or different from one another, each independently selected from the group consisting of an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (preferably $C_{5-7}$ monocyclic cycloalkyl, for example, cyclohexyl), an optionally substituted $C_{2-50}$ (preferably $C_{2-20}$) linear or branched alkenyl, an optionally substituted $C_{6-50}$ (preferably $C_{6-20}$) aryl and a group represented by the formula -Link-(Poly-L-Salt)$_x$, with the proviso that at least one out of the groups $R_1$ to $R_3$ represents the group represented by the formula -Link—(Poly-L-Salt)$_x$, by "optionally substituted" herein, it refers to optionally substituted by one or more substituent selected from the group consisting of oxo, hydroxyl, a group represented by the formula -Link-(Poly-L-Salt)$_x$, a $C_{1-20}$ (preferably $C_{1-10}$) linear or branched alkyl, a $C_{5-10}$ (preferably $C_{5-8}$ or $C_{5-7}$) monocyclic or polycyclic cycloalkyl (for example, cyclohexyl), a $C_{2-20}$ (preferably $C_{2-10}$) linear or branched alkenyl and a $C_{6-20}$ (preferably $C_6$-10) aryl; the group Rh represents an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl or an optionally substituted $C_{6-50}$ (preferably $C_{6-20}$) aryl; the group $X^-$ represents a halogen ion (preferably fluoride ion, chloride ion, bromide ion or iodide ion, more preferably chloride ion) or hydroxide ion ($OH^-$); the group Link represents an optionally substituted x+1 valent $C_{1-50}$ (preferably $C_{1-20}$) linear or branched alkyl, an optionally substituted x+1 valent $C_{5-50}$ (preferably $C_{5-10}$ or $C_{5-8}$) monocyclic or polycyclic cycloalkyl (preferably $C_{5-7}$ monocyclic cycloalkyl, for example, cyclohexyl), an optionally substituted x+1 valent $C_{2-50}$ (preferably $C_{2-20}$) linear or branched alkenyl, an optionally substituted x+1 valent $C_{6-50}$ (preferably $C_{6-20}$) aryl or an optionally substituted x+1 valent $C_{3-50}$ (preferably $C_{3-20}$) linear or branched heteroalkyl; plural group Poly may be identical with or different from one another, each independently represents a group represented by the formula

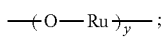

plural group L may be identical with or different from one another, each independently selected from the group consisting of an optionally substituted $C_{1-10}$ linear or branched alkylene and an optionally substituted $C_{2-10}$ linear or branched alkenylene (preferably each independently represents an optionally substituted $C_{1-5}$ linear or branched alkylene); plural group Salt may be identical with or different from one another, each independently represents a group represented by the formula $-A^-(M)_r{}^+$, wherein the group $A^-$ represents a carboxylate ion ($COO^-$) or a sulfonate ion ($SO_3^-$); the numerical value x represents an integer from 1 to 10 (preferably an integer from 1 to 4, for example, 1, 2 or 3); among plural group Poly, plural numerical value y may be identical with or different from one another, each independently represents a value from 0 to 200 (preferably a value from 0 to 100), with the proviso that the sum of all (i.e. x in total) numerical values y is greater than 0; among plural group Poly, plural group Ru may be identical with or different from one another, each independently represents a $C_{2-6}$ linear or branched alkylene (preferably each independently represents $-CH_2-CH_2-$ or $-CH_2-CH(CH_3)-$); the group M represents alkali metal (preferably Li, Na or K), alkaline earth metal (preferably Mg or Ca) or ammonium ($NH_4$); when the group M represents alkali metal or ammonium, r=1; when the group M represents alkaline earth metal, r=0.5, unless otherwise specified, by "optionally substituted", it refers to optionally substituted by one or more substituent selected from the group consisting of oxo, hydroxyl, a $C_{1-20}$ (preferably $C_{1-10}$) linear or branched alkyl, a $C_{5-10}$ (preferably $C_{5-8}$ or $C_{5-7}$) monocyclic or polycyclic cycloalkyl (for example, cyclohexyl), a $C_{2-20}$ (preferably $C_{2-10}$) linear or branched alkenyl and a $C_{6-20}$ (preferably $C_6$-10) aryl, wherein, the linear or branched heteroalkyl represents a group obtained by directly replacing one or more group $-CH_2-$ locating inside the molecular structure of a linear or branched alkyl by a corresponding number of replacing group selected from $-O-$, $-S-$, $-NR'-$ (wherein the group R' represents an optionally substituted $C_{1-20}$ (preferably $C_{1-10}$) linear or branched alkyl, an optionally substituted $C_{5-10}$ (preferably $C_{5-8}$ or $C_{5-7}$) monocyclic or polycyclic cycloalkyl, an optionally substituted $C_{2-20}$ (preferably $C_{2-10}$) linear or branched alkenyl or an optionally substituted $C_{6-20}$ (preferably $C_{6-10}$) aryl) or

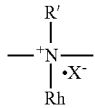

(wherein the group $N^+$ represents a quaternary nitrogen cation; the group R' represents an optionally substituted $C_{1-20}$ (preferably $C_{1-10}$) linear or branched alkyl, an optionally substituted $C_{5-10}$ (preferably $C_{5-8}$ or $C_{5-7}$) monocyclic or polycyclic cycloalkyl, an optionally substituted $C_{2-20}$ (preferably $C_{2-10}$) linear or branched alkenyl or an optionally substituted $C_{6-20}$ (preferably $C_{6-20}$) aryl; the group Rh represents an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl or an optionally substituted $C_{6-50}$ (preferably $C_{6-20}$) aryl; the group $X^-$ represents a halogen ion (preferably fluoride ion, chloride ion, bromide ion or iodide ion, more preferably chloride ion) or hydroxide ion ($OH^-$)), or a group obtained by directly replacing one or more group

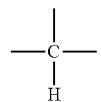

locating inside the molecular structure of a linear or branched alkyl by a corresponding number of replacing group

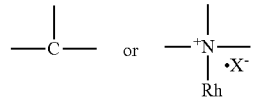

(wherein the group $N^+$ represents a quaternary nitrogen cation; the group Rh represents an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl or an optionally substituted $C_{6-50}$ (preferably $C_{6-20}$) aryl; the group $X^-$ represents a halogen ion (preferably fluoride ion, chloride ion, bromide ion or iodide ion, more preferably chloride ion) or hydroxide ion ($OH^-$)), with the proviso that at least one out of the group $R_1$, the group $R_2$, the group $R_3$ and the group Rh comprises in its molecular structure a $C_8$ linear moiety.

2. The anionic-cationic-nonionic surfactant according to any preceding aspect, wherein the plural group Poly each independently represents an ether segment represented by the formula

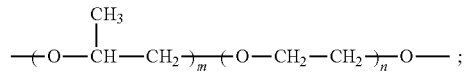

among plural group Poly, plural numerical value m may be identical with or different from one another, each independently represents a value from 0 to 100, preferably a value from 0 to 50; among plural group Poly, plural numerical value n may be identical with or different from one another, each independently represents a value from 0 to 100, preferably a value from 0 to 50, with the proviso that the sum of all numerical values m and all numerical values n is greater than 0; preferably, the sum of all numerical values m is greater than 0 but not greater than 100 (preferably not greater than 50) and/or the sum of all numerical values n is greater than 0 but not greater than 100 (preferably not greater than 50).

3. The anionic-cationic-nonionic surfactant according to any preceding aspect, representing one or more selected from the group consisting of the compound as substantially represented by the formula (I-1), the compound as substantially represented by the formula (I-2), the compound as substantially represented by the formula (I-3) and the compound as substantially represented by the formula (I-4), with the proviso that, at least one N atom contained in the molecular structure thereof bonds to an additional group Rh and an additional group X so as to form into a quaternary ammonium salt/hydroxide group represented by the formula

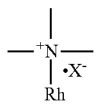

(wherein the group $N^+$ represents the at least one N atom in the form of quaternary nitrogen cation; the group Rh represents an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl or an optionally substituted $C_{6-50}$ (preferably $C_{6-20}$) aryl; the group $X^-$ represents a halogen ion (preferably fluoride ion, chloride ion, bromide ion or iodide ion, more preferably chloride ion) or hydroxide ion ($OH^-$)),

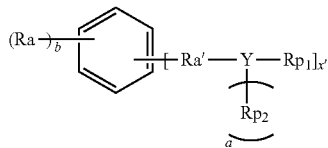
(I-1)

in the formula (I-1), plural group Ra may be identical with or different from one another, each independently selected from the group consisting of hydrogen, an optionally substituted $C_1$-20 linear or branched alkyl, an optionally substituted $C_{2-20}$ linear or branched alkenyl and an optionally substituted $C_{6-10}$ aryl; plural group Ra' may be identical with or different from one another, each independently selected from the group consisting of a single bond, an optionally substituted $C_{1-10}$ linear or branched alkylene, an optionally substituted $C_{2-10}$ linear or branched alkenylene, carbonyl, an optionally substituted $C_{1-10}$ linear or branched alkylene carbonyl and an optionally substituted $C_{2-10}$ linear or branched alkenylene carbonyl, preferably each independently selected from the group consisting of a single bond and an optionally substituted $C_{1-6}$ linear or branched alkylene; the numerical value b represents an integer from 1 to 3, preferably 1; plural group Y may be identical with or different from one another, each independently selected from the group consisting of N and O, with the proviso that when the group Y represents N, a=1, when the group Y represents O, a=0, and at least one group Y represents N; the numerical value x' represents an integer from 1 to 5 (preferably an integer from 1 to 4, for example, 1, 2 or 3); plural group $Rp_1$ may be identical with or different from one another, each independently selected from the group consisting of a group represented by the formula

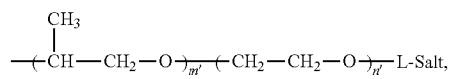

hydrogen, an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl and an optionally substituted $C_{6-50}$ (preferably $C_{6-20}$) aryl, with the proviso that at least one of the groups $Rp_1$ represents a group represented by the formula

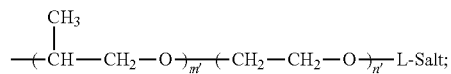

plural group $Rp_2$ may be identical with or different from one another, each independently selected from the group consisting of a group represented by the formula

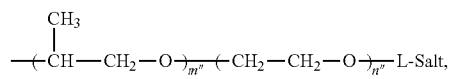

hydrogen, an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl and an optionally substituted $C_{6-50}$ (preferably $C_{6-20}$) aryl; plural numerical value m' may be identical with or different from one another, each independently represents a value from 0 to 100, preferably a value from 0 to 50, plural numerical value n' may be identical with or different from one another, each independently represents a value from 0 to 100, preferably a value from 0 to 50, plural numerical value m" may be identical with or different from one another, each independently represents a value from 0 to 100, preferably a value from 0 to 50, plural numerical value n" may be identical with or different from one another, each independently represents a value from 0 to 100, preferably a value from 0 to 50, with the proviso that the sum of all numerical values m' and all numerical values m" and all numerical values n' and all numerical values n" is greater than 0 but not greater than 200 (preferably greater than 0 but not greater than 100); plural group L may be identical with or different from one another, each independently selected from the group consisting of an optionally substituted $C_{1-10}$ linear or branched alkylene and an optionally substituted $C_{2-10}$ linear or branched alkenylene (preferably each independently represents an optionally substituted $C_{1-5}$ linear or branched alkylene); plural group Salt may be identical with or different from one another, each independently represents a group represented by the formula -$A^-(M)_r^+$, wherein the group $A^-$ represents a carboxylate ion ($COO^-$) or a sulfonate ion ($SO_3^-$); the group M represents alkali metal (preferably Li, Na or K), alkaline earth metal (preferably Mg or Ca) or ammonium ($NH_4$); when the group M represents alkali metal or ammonium, r=1; when the group M represents alkaline earth metal, r=0.5, with the proviso that at least one out of the group Ra and the group Rh comprises in its molecular structure a $C_8$ linear moiety,

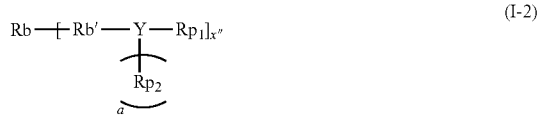
(I-2)

in the formula (I-2), the group Rb represents an optionally substituted $C_{1-49}$ linear or branched alkyl, an optionally substituted $C_{5-49}$ monocyclic or polycyclic cycloalkyl or an optionally substituted $C_{2-49}$ linear or branched alkenyl (preferably an optionally substituted $C_{1-29}$ linear or branched alkyl, an optionally substituted $C_{5-10}$ monocyclic or polycyclic cycloalkyl or an optionally substituted $C_{2-29}$ linear or branched alkenyl, or an optionally substituted $C_{8-29}$ linear or branched alkyl, an optionally substituted $C_{5-8}$ monocyclic or polycyclic cycloalkyl or an optionally substituted $C_{8-29}$ linear or branched alkenyl, or an optionally substituted $C_{8-19}$ linear or branched alkyl, an optionally substituted $C_{5-7}$ monocyclic cycloalkyl (for example, cyclohexyl) or an optionally substituted $C_{8-19}$ linear or branched alkenyl); plural group Rb' may be identical with or different from one another, each independently selected from the group consisting of a single bond and carbonyl; plural group Y may be identical with or different from one another, each independently selected from the group consisting of N and O, with the proviso that when the group Y represents N, a=1, when the group Y represents O, a=0, and at least one group Y represents N; the numerical value x" represents an integer from 1 to 10 (preferably an integer from 1 to 4, for example, 1, 2 or 3); plural group $Rp_1$ may be identical with or different from one another, each independently selected from the group consisting of a group represented by the formula

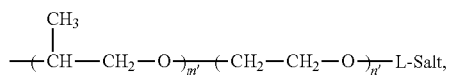

hydrogen, an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl and an optionally substituted $C_{6-50}$ (preferably $C_{6-20}$) aryl, with the proviso that at least one of the groups $Rp_1$ represents a group represented by the formula

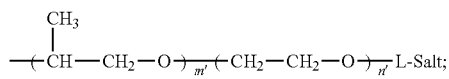

plural group $Rp_2$ may be identical with or different from one another, each independently selected from the group consisting of a group represented by the formula

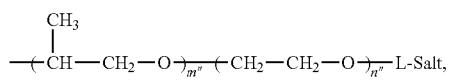

hydrogen, an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl and an optionally substituted $C_{6-50}$ (preferably $C_{6-20}$) aryl; plural numerical value m' may be identical with or different from one another, each independently represents a value from 0 to 100, preferably a value from 0 to 50, plural numerical value n' may be identical with or different from one another, each independently represents a value from 0 to 100, preferably a value from 0 to 50, plural numerical value m" may be identical with or different from one another, each independently represents a value from 0 to 100, preferably a value from 0 to 50, plural numerical value n" may be identical with or different from one another, each independently represents a value from 0 to 100, preferably a value from 0 to 50, with the proviso that the sum of all numerical values m' and all numerical values m" and all numerical values n' and all numerical values n" is greater than 0 but not greater than 200 (preferably greater than 0 but not greater than 100); plural group L may be identical with or different from one another, each independently selected from the group consisting of an optionally substituted $C_{1-10}$ linear or branched alkylene and an optionally substituted $C_{2-10}$ linear or branched alkenylene (preferably each independently represents an optionally substituted $C_{1-5}$ linear or branched alkylene); plural group Salt may be identical with or different from one another, each independently represents a group represented by the formula $-A^-(M)_r^+$, wherein the group $A^-$ represents a carboxylate ion ($COO^-$) or a sulfonate ion ($SO_3^-$); the group M represents alkali metal (preferably Li, Na or K), alkaline earth metal (preferably Mg or Ca) or ammonium ($NH_4$); when the group M represents alkali metal or ammonium, r=1; when the group M represents alkaline earth metal, r=0.5, with the proviso that at least one out of the group Rb and the group Rh comprises in its molecular structure a $C_8$ linear moiety,

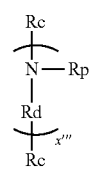
(I-3)

in the formula (I-3), plural group Rc may be identical with or different from one another, each independently selected from the group consisting of an optionally substituted $C_{1-20}$ linear or branched alkyl, an optionally substituted $C_{2-20}$ linear or branched alkenyl, an optionally substituted $C_{1-20}$ linear or branched alkyl carbonyl and an optionally substituted $C_{2-20}$ linear or branched alkenyl carbonyl (or each independently selected from the group consisting of an optionally substituted $C_{1-10}$ linear or branched alkyl, an optionally substituted $C_{2-10}$ linear or branched alkenyl, an optionally substituted $C_{1-10}$ linear or branched alkyl carbonyl and an optionally substituted $C_{2-10}$ linear or branched alkenyl carbonyl, or each independently selected from the group consisting of an optionally substituted $C_{5-20}$ linear or branched alkyl, an optionally substituted $C_{5-20}$ linear or branched alkenyl, an optionally substituted $C_{5-20}$ linear or branched alkyl carbonyl and an optionally substituted $C_{5-20}$ linear or branched alkenyl carbonyl); plural group Rd may be identical with or different from one another, each independently selected from the group consisting of an optionally substituted $C_{1-10}$ linear or branched alkylene, an optionally substituted $C_{2-10}$ linear or branched alkenylene, an optionally substituted $C_{1-10}$ linear or branched alkylene carbonyl, an optionally substituted $C_{2-10}$ linear or branched alkenylene carbonyl, an optionally substituted carbonyl $C_{1-10}$ linear or branched alkylene carbonyl and an optionally substituted carbonyl $C_{2-10}$ linear or branched alkenylene carbonyl (preferably each independently selected from the group consisting of an optionally substituted $C_{1-5}$ linear or branched alkylene and an optionally substituted $C_{1-5}$ linear or branched alkylene carbonyl); the numerical value x''' represents an integer from 1 to 10 (preferably an integer from 1 to 4, for example, 1, 2 or 3); plural group Rp may be identical with or different from one another, each independently selected from the group consisting of a group represented by the formula

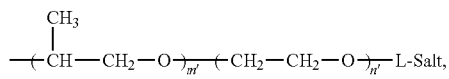

hydrogen, an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl and an optionally substituted $C_{6-50}$ (preferably $C_{6-20}$) aryl, with the proviso that at least one of the groups Rp represents a group represented by the formula

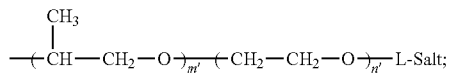

plural numerical value m' may be identical with or different from one another, each independently represents a value from 0 to 100, preferably a value from 0 to 50, plural numerical value n' may be identical with or different from one another, each independently represents a value from 0 to 100, preferably a value from 0 to 50, with the proviso that the sum of all numerical values m' and all numerical values n' is greater than 0 but not greater than 200 (preferably greater than 0 but not greater than 100); plural group L may be identical with or different from one another, each independently selected from the group consisting of an optionally substituted $C_{1-10}$ linear or branched alkylene and an optionally substituted $C_{2-10}$ linear or branched alkenylene (preferably each independently represents an optionally substituted $C_{1-5}$ linear or branched alkylene); plural group Salt may be identical with or different from one another, each independently represents a group represented by the formula $-A^-(M)_r^+$, wherein the group $A^-$ represents a carboxylate ion ($COO^-$) or a sulfonate ion ($SO_3^-$); the group M represents alkali metal (preferably Li, Na or K), alkaline earth metal (preferably Mg or Ca) or ammonium ($NH_4$); when the group M represents alkali metal or ammonium, r=1; when the group M represents alkaline earth metal, r=0.5, with the proviso that at least one out of the group Rc and the group Rh comprises in its molecular structure a $C_8$ linear moiety,

in the formula (I-4), the group Rc represents an optionally substituted $C_{1-20}$ linear or branched alkyl, an optionally substituted $C_{2-20}$ linear or branched alkenyl, an optionally substituted $C_{1-20}$ linear or branched alkyl carbonyl or an optionally substituted $C_{2-20}$ linear or branched alkenyl carbonyl (or an optionally substituted $C_{1-10}$ linear or branched alkyl, an optionally substituted $C_{2-10}$ linear or branched alkenyl, an optionally substituted $C_{1-10}$ linear or branched alkyl carbonyl or an optionally substituted $C_{2-10}$ linear or branched alkenyl carbonyl, or an optionally substituted $C_{5-20}$ linear or branched alkyl, an optionally substituted $C_{5-20}$ linear or branched alkenyl, an optionally substituted $C_{5-20}$ linear or branched alkyl carbonyl or an optionally substituted $C_{5-20}$ linear or branched alkenyl carbonyl); plural group Rd may be identical with or different from one another, each independently selected from the group consisting of an optionally substituted $C_{1-10}$ linear or branched alkylene, an optionally substituted $C_{2-10}$ linear or branched alkenylene, an optionally substituted $C_{1-10}$ linear or branched alkylene carbonyl, an optionally substituted $C_{2-10}$ linear or branched alkenylene carbonyl, an optionally substituted carbonyl $C_{1-10}$ linear or branched alkylene carbonyl and an optionally substituted carbonyl $C_{2-10}$ linear or branched alkenylene carbonyl (preferably each independently selected from the group consisting of an optionally substituted $C_{1-5}$ linear or branched alkylene and an optionally substituted $C_{1-5}$ linear or branched alkylene carbonyl); the group Y represents N or O, with the proviso that when the group Y represents N, a=1, when the group Y represents O, a=0; the numerical value x'''' represents an integer from 1 to 9 (preferably an integer from 1 to 3, more preferably 1 or 2); plural group $Rp_1$ may be identical with or different from one another, each independently selected from the group consisting of a group represented by the formula

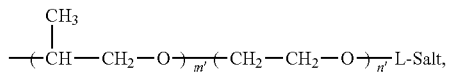

hydrogen, an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl and an optionally substituted $C_{6-50}$ (preferably $C_{6-20}$) aryl, with the proviso that at least one of the groups $Rp_1$ represents a group represented by the formula

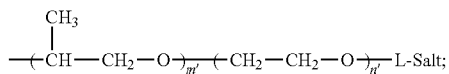

plural group Rp$_2$ may be identical with or different from one another, each independently selected from the group consisting of a group represented by the formula

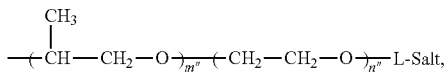

hydrogen, an optionally substituted C$_{1-50}$ (preferably C$_{1-20}$) linear or branched alkyl, an optionally substituted C$_{5-50}$ (preferably C$_{5-10}$ or C$_{5-8}$) monocyclic or polycyclic cycloalkyl (for example, cyclohexyl), an optionally substituted C$_{2-50}$ (preferably C$_{2-20}$) linear or branched alkenyl and an optionally substituted C$_{6-50}$ (preferably C$_{6-20}$) aryl; plural group Rp$_3$ may be identical with or different from one another, each independently selected from the group consisting of a group represented by the formula

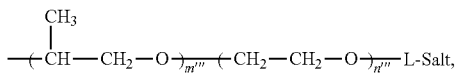

hydrogen, an optionally substituted C$_{1-50}$ (preferably C$_{1-20}$) linear or branched alkyl, an optionally substituted C$_{5-50}$ (preferably C$_{5-10}$ or C$_{5-8}$) monocyclic or polycyclic cycloalkyl (for example, cyclohexyl), an optionally substituted C$_{2-50}$ (preferably C$_{2-20}$) linear or branched alkenyl and an optionally substituted C$_{6-50}$ (preferably C$_{6-20}$) aryl; plural numerical value m' may be identical with or different from one another, each independently represents a value from 0 to 100, preferably a value from 0 to 50, plural numerical value n' may be identical with or different from one another, each independently represents a value from 0 to 100, preferably a value from 0 to 50, plural numerical value m'' may be identical with or different from one another, each independently represents a value from 0 to 100, preferably a value from 0 to 50, plural numerical value n'' may be identical with or different from one another, each independently represents a value from 0 to 100, preferably a value from 0 to 50, plural numerical value m''' may be identical with or different from one another, each independently represents a value from 0 to 100, preferably a value from 0 to 50, plural numerical value n''' may be identical with or different from one another, each independently represents a value from 0 to 100, preferably a value from 0 to 50, with the proviso that the sum of all numerical values m' and all numerical values m'' and all numerical values m''' and all numerical values n' and all numerical values n'' and all numerical values n''' is greater than 0 but not greater than 200 (preferably greater than 0 but not greater than 100); plural group L may be identical with or different from one another, each independently selected from the group consisting of an optionally substituted C$_{1-10}$ linear or branched alkylene and an optionally substituted C$_{2-10}$ linear or branched alkenylene (preferably each independently represents an optionally substituted C$_{1-5}$ linear or branched alkylene); plural group Salt may be identical with or different from one another, each independently represents a group represented by the formula -A$^-$(M)$_r^+$, wherein the group A$^-$ represents a carboxylate ion (COO$^-$) or a sulfonate ion (SO$_3^-$); the group M represents alkali metal (preferably Li, Na or K), alkaline earth metal (preferably Mg or Ca) or ammonium (NH$_4$); when the group M represents alkali metal or ammonium, r=1; when the group M represents alkaline earth metal, r=0.5, with the proviso that at least one out of the group Rc and the group Rh comprises in its molecular structure a C$_8$ linear moiety, by "optionally substituted", it refers to optionally substituted by one or more substituent selected from the group consisting of hydroxyl, a C$_{1-20}$ (preferably C$_{1-10}$) linear or branched alkyl, a C$_{5-10}$ (preferably C$_{5-8}$ or C$_{5-7}$) monocyclic or polycyclic cycloalkyl (for example, cyclohexyl), a C$_{2-20}$ (preferably C$_{2-10}$) linear or branched alkenyl and a C$_{6-20}$ (preferably C$_{6-10}$) aryl.

4. The anionic-cationic-nonionic surfactant according to any preceding aspect, wherein at least a part of the group X$^-$ and the group (M)$_r^+$ presents in the form of (M)$_r^+$X$^-$ and independently from the anionic-cationic-nonionic surfactant, preferably, throughout the molecular structure of the anionic-cationic-nonionic surfactant, assuming that the total number of the group X$^-$ is e1, the total number of the group N$^+$ is e2, the total number of the group A$^-$ is e3, the total number of the group (M)$_r^+$ is e4, if e2=e3, then 0≤e1≤e2, 0≤e4≤e3; or, if e2>e3, then 0<e1≤e2, 0≤e4≤e3; or, if e2<e3, then 0≤e1≤e2, 0<e4≤e3, with the proviso that e1+e3=e2+e4, or e2=e3, e1=0, e4=0.

5. A process for producing an anionic-cationic-nonionic surfactant, which is characterized by including the following steps:

Step (1): reacting one or more multifunctional compound containing nitrogen and carrying one or more functional group selected from the group consisting of —OH, —NH$_2$ and —NH— with one or more alkylene oxide represented by the following formula (Y) in the presence of an alkaline catalyst (preferably alkali metal hydroxide), to obtain an ether product,

(Y)

in the formula (Y), the group Ru' represents a C$_{2-6}$ linear or branched alkylene (preferably —CH$_2$—CH$_2$— or —CH$_2$—CH(CH$_3$)—), Step (2): reacting the ether product with a quaternizing agent represented by the formula (A), whereby obtaining a cationic-nonionic surfactant, wherein the amount of the quaternizing agent is such that at least one N atom in the molecular structure of the ether product is converted into its corresponding quaternary ammonium salt group,

Rh—X'  (A)

in the formula (A), the group Rh represents an optionally substituted C$_{1-50}$ (preferably C$_{1-20}$) linear or branched alkyl, an optionally substituted C$_{5-50}$ (preferably C$_{5-10}$ or C$_{5-8}$) monocyclic or polycyclic cycloalkyl (for example, cyclohexyl), an optionally substituted C$_{2-50}$ (preferably C$_{2-20}$) linear or branched alkenyl or an optionally substituted C$_{6-50}$ (preferably C$_{6-20}$) aryl; the group X' represents a halogen atom (preferably fluorine atom, chlorine atom, bromine atom and iodine atom, more preferably chlorine atom), with the proviso that at least one out of the multifunctional compound and the quaternizing agent comprises in its molecular structure a C$_8$ linear moiety, Step (3): reacting the cationic-nonionic surfactant with one or more compound represented by the following formula (Z) in the presence of an alkaline catalyst (preferably alkali metal hydroxide), whereby obtaining the anionic-cationic-nonionic surfactant,

$$G\text{-}L\text{-}AS \tag{Z}$$

in the formula (Z), the group G represents a halogen atom (preferably fluorine atom, chlorine atom, bromine atom or iodine atom, more preferably chlorine atom) or hydroxyl; the group L represents an optionally substituted $C_{1\text{-}10}$ linear or branched alkylene or an optionally substituted $C_{2\text{-}10}$ linear or branched alkenylene (preferably an optionally substituted $C_{1\text{-}5}$ linear or branched alkylene); the group AS represents a group represented by the formula $\text{-}A^-(M')_r^+$; the group $A^-$ represents a carboxylate ion ($COO^-$) or a sulfonate ion ($SO_3^-$); the group M' represents hydrogen, alkali metal (preferably Li, Na or K), alkaline earth metal (preferably Mg or Ca) or ammonium ($NH_4$); when the group M' represents hydrogen, alkali metal or ammonium, r=1; when the group M' represents alkaline earth metal, r=0.5, optionally, Step (4): at least a part of the quaternary ammonium salt group on the molecular structure of the anionic-cationic-nonionic surfactant obtained from any step of the process is converted into the corresponding quaternary ammonium hydroxide group, and/or, at least a part of the quaternary ammonium hydroxide group on the molecular structure of the anionic-cationic-nonionic surfactant is converted into the corresponding quaternary ammonium salt group, optionally, Step (5): isolating at least a part (preferably all) of the compound $(M')_rX'$ present in a free form from the anionic-cationic-nonionic surfactant obtained from any step of the process, by "optionally substituted", it refers to optionally substituted by one or more substituent selected from the group consisting of hydroxyl, a $C_{1\text{-}20}$ (preferably $C_{1\text{-}10}$) linear or branched alkyl, a $C_{5\text{-}10}$ (preferably $C_{5\text{-}8}$ or $C_{5\text{-}7}$) monocyclic or polycyclic cycloalkyl (for example, cyclohexyl), a $C_{2\text{-}20}$ (preferably $C_{2\text{-}10}$) linear or branched alkenyl and a $C_{6\text{-}20}$ (preferably $C_{640}$) aryl.

6. The process according to any preceding aspect, wherein the multifunctional compound is one or more compound represented by the following formula (X),

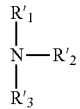

(X)

in the formula (X), the groups $R'_1$ to $R'_3$ may be identical with or different from one another, each independently selected from the group consisting of hydrogen, an optionally substituted $C_{1\text{-}50}$ (preferably $C_{1\text{-}20}$) linear or branched alkyl, an optionally substituted $C_{5\text{-}50}$ (preferably $C_{5\text{-}10}$ or $C_{5\text{-}8}$) monocyclic or polycyclic cycloalkyl (preferably $C_{5\text{-}7}$ monocyclic cycloalkyl, for example, cyclohexyl), an optionally substituted $C_{2\text{-}50}$ (preferably $C_{2\text{-}20}$) linear or branched alkenyl, an optionally substituted $C_{6\text{-}50}$ (preferably $C_{6\text{-}20}$) aryl and a group represented by the formula $\text{-}L_A\text{-}(\text{Func})_{x0}$, with the proviso that at least one out of the groups $R'_1$ to $R'_3$ represents hydrogen or a group represented by the formula $\text{-}L_A\text{-}(\text{Func})_{x0}$, by "optionally substituted" herein, it refers to optionally substituted by one or more substituent selected from the group consisting of oxo, hydroxyl, a group represented by the formula $\text{-}L_A\text{-}(\text{Func})_{x0}$, a $C_{1\text{-}20}$ (preferably $C_{1\text{-}10}$) linear or branched alkyl, a $C_{5\text{-}10}$ (preferably $C_{5\text{-}8}$ or $C_{5\text{-}7}$) monocyclic or polycyclic cycloalkyl (for example, cyclohexyl), a $C_{2\text{-}20}$ (preferably $C_{2\text{-}10}$) linear or branched alkenyl and a $C_{6\text{-}20}$ (preferably $C_{6\text{-}10}$) aryl; the group $L_A$ represents an optionally substituted x0+1 valent $C_{1\text{-}50}$ (preferably $C_{1\text{-}20}$) linear or branched alkyl, an optionally substituted x0+1 valent $C_{5\text{-}50}$ (preferably $C_{5\text{-}10}$ or $C_{5\text{-}8}$) monocyclic or polycyclic cycloalkyl (preferably $C_{5\text{-}7}$ monocyclic cycloalkyl, for example, cyclohexyl), an optionally substituted x0+1 valent $C_{2\text{-}50}$ (preferably $C_{2\text{-}20}$) linear or branched alkenyl, an optionally substituted x0+1 valent $C_{6\text{-}50}$ (preferably $C_{6\text{-}20}$) aryl or an optionally substituted x0+1 valent $C_{3\text{-}50}$ (preferably $C_{3\text{-}20}$) linear or branched heteroalkyl group; the numerical value x0 is an integer from 1 to 10, preferably an integer from 1 to 4, for example, 1, 2 or 3; plural group Func may be identical with or different from one another, each independently selected from the group consisting of —OH, —NH— and —NH$_2$, the linear or branched heteroalkyl represents a group obtained by directly replacing one or more group —CH$_2$— locating inside the molecular structure of a linear or branched alkyl by a corresponding number of replacing group selected from —O—, —S—, —NR'— (wherein the group R' represents an optionally substituted $C_{1\text{-}20}$ (preferably $C_{1\text{-}10}$) linear or branched alkyl, an optionally substituted $C_{5\text{-}10}$ (preferably $C_{5\text{-}8}$ or $C_{5\text{-}7}$) monocyclic or polycyclic cycloalkyl, an optionally substituted $C_{2\text{-}20}$ (preferably $C_{2\text{-}10}$) linear or branched alkenyl or an optionally substituted $C_{6\text{-}20}$ (preferably $C_{6\text{-}10}$) aryl) or

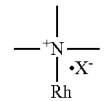

(wherein the group $N^+$ represents a quaternary nitrogen cation; the group R' represents an optionally substituted $C_{1\text{-}20}$ (preferably $C_{1\text{-}10}$) linear or branched alkyl, an optionally substituted $C_{5\text{-}10}$ (preferably $C_{5\text{-}8}$ or $C_{5\text{-}7}$) monocyclic or polycyclic cycloalkyl, an optionally substituted $C_{2\text{-}20}$ (preferably $C_{2\text{-}10}$) linear or branched alkenyl or an optionally substituted $C_{6\text{-}20}$ (preferably $C_{6\text{-}10}$) aryl; the group Rh represents an optionally substituted $C_{1\text{-}50}$ (preferably $C_{1\text{-}20}$) linear or branched alkyl, an optionally substituted $C_{5\text{-}50}$ (preferably $C_{5\text{-}10}$ or $C_{5\text{-}8}$) monocyclic or polycyclic cycloalkyl (for example, cyclohexyl), an optionally substituted $C_{2\text{-}50}$ (preferably $C_{2\text{-}20}$) linear or branched alkenyl or an optionally substituted $C_{6\text{-}50}$ (preferably $C_{6\text{-}20}$) aryl; the group X" represents a halogen ion (preferably fluoride ion, chloride ion, bromide ion or iodide ion, more preferably chloride ion) or hydroxide ion ($OH^-$)), or a group obtained by directly replacing one or more group

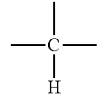

locating inside the molecular structure of a linear or branched alkyl by a corresponding number of replacing group

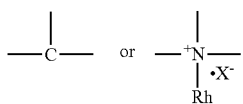

(wherein the group N⁺ represents a quaternary nitrogen cation; the group Rh represents an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl or an optionally substituted $C_{6-50}$ (preferably $C_{6-20}$) aryl; the group X⁻ represents a halogen ion (preferably fluoride ion, chloride ion, bromide ion or iodide ion, more preferably chloride ion) or hydroxide ion (OH⁻)), the multifunctional compound is preferably one or more selected from the group consisting of the compound represented by the following formula (X-1), the compound represented by the following formula (X-2), the compound represented by the following formula (X-3) and the compound represented by the following formula (X-4),

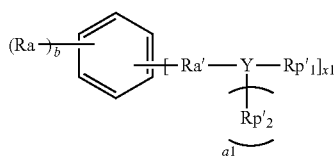 (X-1)

in the formula (X-1), plural group Ra may be identical with or different from one another, each independently selected from the group consisting of hydrogen, an optionally substituted $C_{1-20}$ linear or branched alkyl, an optionally substituted $C_{2-20}$ linear or branched alkenyl and an optionally substituted $C_{6-20}$ aryl; plural group Ra' may be identical with or different from one another, each independently selected from the group consisting of a single bond, an optionally substituted $C_{1-10}$ linear or branched alkylene, an optionally substituted $C_{2-10}$ linear or branched alkenylene, carbonyl, an optionally substituted $C_{1-10}$ linear or branched alkylene carbonyl and an optionally substituted $C_{2-10}$ linear or branched alkenylene carbonyl, preferably each independently selected from the group consisting of a single bond and an optionally substituted $C_{1-6}$ linear or branched alkylene; the numerical value b represents an integer from 1 to 3, preferably 1; plural group Y may be identical with or different from one another, each independently selected from the group consisting of N and O, with the proviso that when the group Y represents N, a1=1, when the group Y represents O, a1=0, and at least one group Y represents N; the numerical value x1 represents an integer from 1 to 5 (preferably an integer from 1 to 4, for example, 1, 2 or 3); plural group Rp'₁ may be identical with or different from one another, each independently selected from the group consisting of hydrogen, an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl and an optionally substituted $C_{6-50}$ (preferably $C_{6-20}$) aryl, with the proviso that at least one of the groups Rp'₁ represents hydrogen; plural group Rp'₂ may be identical with or different from one another, each independently selected from the group consisting of hydrogen, an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl and an optionally substituted $C_{6-50}$ (preferably $C_{6-20}$) aryl,

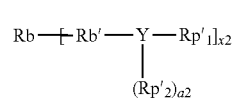 (X-2)

in the formula (X-2), the group Rb represents an optionally substituted $C_{1-49}$ linear or branched alkyl, an optionally substituted $C_{5-49}$ monocyclic or polycyclic cycloalkyl or an optionally substituted $C_{2-49}$ linear or branched alkenyl (preferably an optionally substituted $C_{1-29}$ linear or branched alkyl, an optionally substituted $C_{5-10}$ monocyclic or polycyclic cycloalkyl or an optionally substituted $C_{2-29}$ linear or branched alkenyl, or an optionally substituted $C_{8-29}$ linear or branched alkyl, an optionally substituted $C_{5-8}$ monocyclic or polycyclic cycloalkyl or an optionally substituted $C_{8-29}$ linear or branched alkenyl, or an optionally substituted $C_{8-19}$ linear or branched alkyl, an optionally substituted $C_{5-7}$ monocyclic cycloalkyl (for example, cyclohexyl) or an optionally substituted $C_{8-19}$ linear or branched alkenyl); plural group Rb' may be identical with or different from one another, each independently selected from the group consisting of a single bond and carbonyl; plural group Y may be identical with or different from one another, each independently selected from the group consisting of N and O, with the proviso that when the group Y represents N, a2=1, when the group Y represents O, a2=0, and at least one group Y represents N; the numerical value x2 represents an integer from 1 to 10 (preferably an integer from 1 to 4, for example, 1, 2 or 3); plural group Rp'₁ may be identical with or different from one another, each independently selected from the group consisting of hydrogen, an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl and an optionally substituted $C_{6-50}$ (preferably $C_{6-20}$) aryl, with the proviso that at least one of the groups Rp'₁ represents hydrogen; plural group Rp'₂ may be identical with or different from one another, each independently selected from the group consisting of hydrogen, an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl and an optionally substituted $C_{6-50}$ (preferably $C_{6-20}$) aryl,

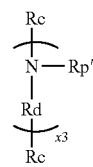 (X-3)

in the formula (X-3), plural group Rc may be identical with or different from one another, each independently selected from the group consisting of an optionally substituted $C_{1-20}$ linear or branched alkyl, an optionally substituted $C_{2-20}$ linear or branched alkenyl, an optionally substituted $C_{1-20}$ linear or branched alkyl carbonyl and an optionally substituted $C_{2-20}$ linear or branched alkenyl carbonyl (or each independently selected from the group consisting of an optionally substituted $C_{1-10}$ linear or branched alkyl, an optionally substituted $C_{2-10}$ linear or branched alkenyl, an optionally substituted $C_{1-10}$ linear or branched alkyl carbonyl and an optionally substituted $C_{2-10}$ linear or branched alkenyl carbonyl, or each independently selected from the group consisting of an optionally substituted $C_{8-20}$ linear or branched alkyl, an optionally substituted $C_{8-20}$ linear or branched alkenyl, an optionally substituted $C_{8-20}$ linear or branched alkyl carbonyl and an optionally substituted $C_{8-20}$ linear or branched alkenyl carbonyl); plural group Rd may be identical with or different from one another, each independently selected from the group consisting of an optionally substituted $C_{1-10}$ linear or branched alkylene, an optionally substituted $C_{2-10}$ linear or branched alkenylene, an optionally substituted $C_{1-10}$ linear or branched alkylene carbonyl, an optionally substituted $C_{2-10}$ linear or branched alkenylene carbonyl, an optionally substituted carbonyl $C_{1-10}$ linear or branched alkylene carbonyl and an optionally substituted carbonyl $C_{2-10}$ linear or branched alkenylene carbonyl (preferably each independently selected from the group consisting of an optionally substituted $C_{1-5}$ linear or branched alkylene and an optionally substituted $C_{1-5}$ linear or branched alkylene carbonyl); the numerical value x3 represents an integer from 1 to 10 (preferably an integer from 1 to 4, for example, 1, 2 or 3); plural group Rp' may be identical with or different from one another, each independently selected from the group consisting of hydrogen, an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl and an optionally substituted $C_{6-50}$ (preferably $C_{6-20}$) aryl, with the proviso that at least one of the groups Rp' represents hydrogen,

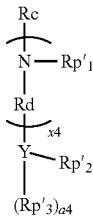 (X-4)

in the formula (X-4), the group Rc represents an optionally substituted $C_{1-20}$ linear or branched alkyl, an optionally substituted $C_{2-20}$ linear or branched alkenyl, an optionally substituted $C_{1-20}$ linear or branched alkyl carbonyl or an optionally substituted $C_{2-20}$ linear or branched alkenyl carbonyl (or an optionally substituted $C_{1-10}$ linear or branched alkyl, an optionally substituted $C_{2-10}$ linear or branched alkenyl, an optionally substituted $C_{1-10}$ linear or branched alkyl carbonyl or an optionally substituted $C_{2-10}$ linear or branched alkenyl carbonyl, or an optionally substituted $C_{5-20}$ linear or branched alkyl, an optionally substituted $C_{5-20}$ linear or branched alkenyl, an optionally substituted $C_{5-20}$ linear or branched alkyl carbonyl or an optionally substituted $C_{5-20}$ linear or branched alkenyl carbonyl); plural group Rd may be identical with or different from one another, each independently selected from the group consisting of an optionally substituted $C_{1-10}$ linear or branched alkylene, an optionally substituted $C_{2-10}$ linear or branched alkenylene, an optionally substituted $C_{1-10}$ linear or branched alkylene carbonyl, an optionally substituted $C_{2-10}$ linear or branched alkenylene carbonyl, an optionally substituted carbonyl $C_{1-10}$ linear or branched alkylene carbonyl and an optionally substituted carbonyl $C_{2-10}$ linear or branched alkenylene carbonyl (preferably each independently selected from the group consisting of an optionally substituted $C_{1-5}$ linear or branched alkylene and an optionally substituted $C_{1-5}$ linear or branched alkylene carbonyl); the group Y represents N or O, with the proviso that when the group Y represents N, a4=1, when the group Y represents O, a4=0; the numerical value x4 represents an integer from 1 to 9 (preferably an integer from 1 to 3, more preferably 1 or 2); plural group Rp'$_1$ may be identical with or different from one another, each independently selected from the group consisting of hydrogen, an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl and an optionally substituted $C_{6-50}$ (preferably $C_{6-20}$) aryl, with the proviso that at least one of the groups Rp'$_1$ represents hydrogen; plural group Rp'$_2$ may be identical with or different from one another, each independently selected from the group consisting of hydrogen, an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl and an optionally substituted $C_{6-50}$ (preferably $C_{6-20}$) aryl; plural group Rp' 3 may be identical with or different from one another, each independently selected from the group consisting of hydrogen, an optionally substituted $C_{1-50}$ (preferably $C_{1-20}$) linear or branched alkyl, an optionally substituted $C_{5-50}$ (preferably $C_{5-10}$ or $C_{5-8}$) monocyclic or polycyclic cycloalkyl (for example, cyclohexyl), an optionally substituted $C_{2-50}$ (preferably $C_{2-20}$) linear or branched alkenyl and an optionally substituted $C_{6-50}$ (preferably $C_{6-20}$) aryl, unless otherwise specified, by "optionally substituted", it refers to optionally substituted by one or more substituent selected from the group consisting of oxo, hydroxyl, a $C_{1-20}$ (preferably $C_{1-10}$) linear or branched alkyl, a $C_{5-10}$ (preferably $C_{5-8}$ or $C_{5-7}$) monocyclic or polycyclic cycloalkyl (for example, cyclohexyl), a $C_{2-20}$ (preferably $C_{2-10}$) linear or branched alkenyl and a $C_{6-20}$ (preferably $C_6$-10) aryl.

7. The process according to any preceding aspect, wherein the ratio by molar of the multifunctional compound to the alkylene oxide is 1:0-200 (preferably 1:0-100), excluding 0; the ratio by molar of the multifunctional compound to the compound represented by the formula (Z) is 1:1-10 (preferably 1:1-3); the reaction conditions in Step (1) include a reaction temperature from the room temperature to 300 degrees Celsius (preferably 100-200 degrees Celsius), a reaction duration from 1 to 20 h (preferably from 1 to 10 h); the reaction conditions in Step (2) include a reaction temperature from 0 to 300 degrees Celsius (preferably 50-150 degrees Celsius), a reaction duration from 1 to 20 h (preferably from 4 to 15 h); the reaction conditions in Step (3) include a reaction temperature from 0 to 300 degrees Celsius (preferably 50-200 degrees Celsius), a reaction duration from 1 to 20 h (preferably from 4 to 10 h).

8. The process according to any preceding aspect, wherein the alkylene oxide comprises at least propylene oxide, and the multifunctional compound is made to firstly react with propylene oxide.

9. A flooding fluid composition for tertiary oil recovery, which is characterized by comprising an anionic-cationic-nonionic surfactant according to any preceding aspect or an anionic-cationic-nonionic surfactant produced in line with the process according to any preceding aspect, and water, wherein the content of the anionic-cationic-nonionic surfactant is 0.001-10 wt %, preferably 0.005-5 wt %, more preferably 0.02-1 wt %, relative to the total weight (as 100 wt %) of the flooding fluid composition for tertiary oil recovery.

10. The flooding fluid composition for tertiary oil recovery according to any preceding aspect, comprising no inorganic alkali.

11. A process for producing a flooding fluid composition for tertiary oil recovery, which is characterized by mixing an anionic-cationic-nonionic surfactant according to any preceding aspect or an anionic-cationic-nonionic surfactant produced in line with the process according to any preceding aspect at least with water, wherein the content of the anionic-cationic-nonionic surfactant is 0.001-10 wt %, preferably 0.005-5 wt %, more preferably 0.02-1 wt %, relative to the total weight (as 100 wt %) of the flooding fluid composition for tertiary oil recovery.

12. A tertiary oil recovery process, which is characterized by including a step of conducting tertiary oil recovery in the presence of an anionic-cationic-nonionic surfactant according to any preceding aspect, an anionic-cationic-nonionic surfactant produced in line with the process according to any preceding aspect, an flooding fluid composition for tertiary oil recovery according to any preceding aspect, or an flooding fluid composition for tertiary oil recovery produced in line with the process according to any preceding aspect, as a flooding fluid.

13. The tertiary oil recovery process according to any preceding aspect, wherein no inorganic alkali is used.

TECHNICAL EFFECTS

The anionic-cationic-nonionic surfactant according to this invention exhibits, as compared with the prior art, significantly improved interfacial activity. For example, at a concentration of as low as 0.01 to 0.05 wt %, the present anionic-cationic-nonionic surfactant can still provide a significantly ultra low interfacial tension of $10^{-3}$-$10^{-4}$ mN/m with crude oil.

The anionic-cationic-nonionic surfactant or flooding fluid composition for tertiary oil recovery according to this invention, even at elevated temperatures, is capable of forming a stable and transparent aqueous solution in water, and preferably, even after stored (especially at elevate temperatures) for a long term, remains stable in terms of chemical composition and interfacial activity.

The anionic-cationic-nonionic surfactant or flooding fluid composition for tertiary oil recovery according to this invention, is not associated with the chromatographic fractionation problem in use, whereby exhibiting excellent stability in use.

The flooding fluid composition for tertiary oil recovery according to this invention, which contains the anionic-cationic-nonionic surfactant of this invention as the surfactant component, exhibits as compared with the prior art improved oil displacement efficiency and oil washing capability (for example, with an oil washing rate of more than 40% for crude oil), and is capable of significantly enhancing oil recovery.

The flooding fluid composition for tertiary oil recovery according to this invention is characterized by a simplified system, containing no inorganic alkali, no harm to the reservoir and oil wells, not corrosive to equipments and pipings, and not leading to difficult demulsification.

SPECIFIC MODE TO CARRY OUT THIS INVENTION

This invention will be described in details hereinafter with reference to the following specific embodiments. However, it should be noted that the protection scope of this invention should not be construed as limited to these specific embodiments, but rather determined by the attached claims.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention.

Further, to the extent that any meaning or definition of a term in this document conflicts with any meaning or definition of the same term in a document incorporated by reference, the meaning or definition assigned to that term in this document shall govern.

In the context of this specification, the term "halo" or the like refers to fluoro, chloro, bromo or iodo.

In the context of this specification, by "linear or branched heteroalkyl", it refers to a group obtained by directly replacing one or more (for example, from 1 to 4, from 1 to 3, from 1 to 2, or 1) group —$CH_2$— locating inside the molecular structure (not including that at the terminal of the main chain or any side chain in the molecular structure) of a linear or branched alkyl by a corresponding number of replacing group selected from —O—, —S—, —NR'— or

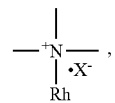

or a group obtained by directly replacing one or more (for example, from 1 to 3, from 1 to 2, or 1) group

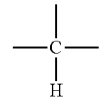

locating inside the molecular structure (not including that at the terminal of the main chain or any side chain in the molecular structure) of a linear or branched alkyl by a corresponding number of replacing group

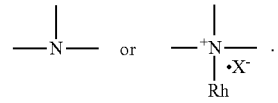

As the replacing group, it is preferably —NR'— or

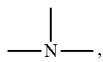, more preferably —NR'—. Herein, the group R' represents an optionally substituted $C_{1-20}$ linear or branched alkyl, an optionally substituted $C_{5-10}$ monocyclic or polycyclic cycloalkyl, an optionally substituted $C_{2-20}$ linear or branched alkenyl or an optionally substituted $C_{6-20}$ aryl. As the $C_{1-20}$ linear or branched alkyl, for example, there may be exemplified a $C_{1-10}$ linear or branched alkyl or a $C_{1-6}$ linear or branched alkyl, specifically methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl. As the group R', it is preferably a $C_{1-20}$ linear or branched alkyl or a $C_{5-7}$ monocyclic cycloalkyl, specifically methyl, ethyl or cyclohexyl. The group $N^+$ represents a quaternary nitrogen cation. The group Rh represents an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl or an optionally substituted $C_{6-50}$ aryl. In the definition of the group Rh, as the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a $C_{2-20}$ linear or branched alkenyl or a $C_{8-20}$ linear or branched alkenyl, specifically octadecenyl, dodecenyl, linolyl, vinyl, propenyl or allyl, and so on. As $C_{6-50}$ aryl, for example, there may be exemplified a $C_{6-20}$ aryl or a $C_{6-10}$ aryl, specifically phenyl or naphthyl. The group $X^-$ represents a halogen ion (including fluoride ion, chloride ion, bromide ion or iodide ion) or hydroxide ion ($OH^-$), wherein preference is given to a halogen ion, more preferably chloride ion. Herein, by optionally substituted, it refers to optionally substituted by one or more (for example, from 1 to 4, from 1 to 3, from 1 to 2 or 1) substituent selected from the group consisting of hydroxyl, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl. It is obvious that, from the standpoint of structure stability, when plural exist, these replacing groups do not directly bond to one another. Further, the carbon atom number of the linear or branched alkyl is reduced accordingly due to the replacement of the group —$CH_2$— or

by the replacing group, however, to simplify the description, the carbon atom number of the linear or branched alkyl before the replacement is still used to refer to the carbon atom number of the resultant linear or branched heteroalkyl. As the linear or branched heteroalkyl, if specifically exemplified, a $C_4$ linear alkyl, for example,

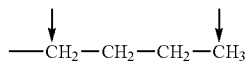

(In this formula, the groups indicated by the arrow marks do not locate inside the molecular structure of the linear alkyl, but rather at the terminal of the main chain) if directly replaced by one replacing group —O—, —$CH_2$—O—$CH_2$—$CH_3$ or $CH_2$—$CH_2$—O—$CH_3$ will be obtained, called as $C_4$ linear heteroalkyl. Or, a $C_4$ branched alkyl, for example,

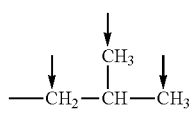

(In this formula, the groups indicated by the arrow marks do not locate inside the molecular structure of the branched alkyl, but rather at the terminal of the main chain and that of the side chain) if directly replaced by one replacing group

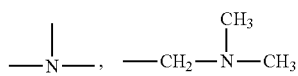

will be obtained, called as $C_4$ branched heteroalkyl. According to this invention, as the linear or branched heteroalkyl, there may be exemplified a $C_{3-50}$ linear or branched heteroalkyl, specifically a $C_{5-50}$ linear or branched heteroalkyl, a $C_{8-30}$ linear or branched heteroalkyl or a $C_{8-20}$ linear or branched heteroalkyl, or a $C_{3-20}$ linear or branched heteroalkyl, a $C_{3-10}$ linear or branched heteroalkyl or a $C_{3-6}$ linear or branched heteroalkyl.

In the context of this specification, if a group is defined or described in the form of "numerical value+valent+group" or the like, it refers to a group obtained by removing a number of hydrogen atom (wherein the number of the hydrogen atom corresponds to the numerical value) from the corresponding basic structure (for example, a chain, a ring or a combination thereof) of the group, preferably refers to a group obtained by removing a number of hydrogen atom (wherein the number of the hydrogen atom corresponds to the numerical value) from a carbon atom (preferably from a saturated carbon atom and/or if the numerical value is two or more, from different carbon atoms) contained in the basic structure. For example, "3 valent linear or branched alkyl "refers to a group obtained by removing 3 (three) hydrogen atoms from a linear or branched alkane (i.e. The corresponding basic structure (chain) of the linear or branched alkyl), while "2 valent linear or branched heteroalkyl "refers to a group obtained by removing 2 (two) hydrogen atoms from a linear or branched heteroalkane (preferably from a carbon atom of the heteroalkane, or further, from two different carbon atoms in the heteroalkane). Obviously, the expression "0 valent+group" represents the basic structure itself, for example, a 0 valent alkyl corresponds to an alkane.

In the context of this specification, by "comprising a $C_8$ linear moiety in the structure", it means that the concerned compound or group throughout its chemical structure, comprises (for example, one or more) a structure segment made by successively connecting 8 carbon atoms in a linear manner. Depending on the nature of the chemical structure or how the chemical structure is substituted, these 8 carbon atoms may each independently present in unsubstituted or substituted form. Further, the $C_8$ linear moiety may locate inside the chemical structure (for example, as the main chain of the chemical structure), or at the terminal of the chemical structure (for example, as a terminal or side chain of the chemical structure), but not limiting thereto. Specifically, if a group $R_1$ (as hereinafter described) comprises in the structure a $C_8$ linear moiety, assuming that the group $R_1$ is an optionally substituted $C_{10}$ linear or branched alkyl, the group $R_1$ may be —$\underline{CH_2—CH_2—CH_2—CH_2—CH_2—CH_2—CH_2—CH_2}$—$CH_2—CH_3$, —$\underline{CH_2—CH_2—CH_2—CH_2—CH_2—CH_2—CH_2—CH(CH_3)}$—$CH_3$, —$\underline{CH_2—CH_2—CH_2—CH_2—CH_2—CH_2—CH(CH_3)—CH(CH_3)}$—$CH_3$, —$\underline{CH_2—CH(OH)—CH_2—CH_2—CH_2—CH(CH_3)—CH(CH_3)}$—$CH_3$, —$\underline{CH_2—CH_2—CH_2—CH_2—CH_2—C(OH)(CH_3)—CH(CH_3)}$—$CH_3$, —$\underline{CH_2—CH_2—C(=O)—CH_2—CH_2—CH(CH_3)—CH(CH_3)}$—$CH_3$ or —$\underline{CH_2—CH(CH_3)—CH_2—C(=O)—CH_2—CH_2—CH(CH_3)}$—$CH_3$ (in these alkyls, each underlined structure segment made by successively connecting 8 carbon atoms in a linear manner corresponding to a $C_8$ linear moiety) or the like, but may not be —$CH(CH_3)—CH_2—CH_2—CH_2—CH(CH_3)—CH(CH_3)—CH_3$ or —$CH(CH_2CH_2CH_2CH_3)—CH(CH_3)—CH(CH_3)—CH_3$ or the like (not comprising a structure segment made by successively connecting 8 carbon atoms in a linear manner). As illustrated by the example, as long as the group $R_1$ in its structure comprises a $C_8$ linear moiety as a part (segment) thereof, there is no specific limitation as to where the $C_8$ linear moiety locates, say as the main chain, at the terminal or as a side chain. Further, it is obvious that it is not necessary for the group $R_1$ is made of only 8 carbon atoms or the $C_8$ linear moiety only presents as —$CH_2—CH_2—CH_2—CH_2—CH_2—CH_2—CH_2—CH_2$—.

Unless otherwise specified, percents, parts or ratios or the like mentioned in this specification are all on a weight basis.

According to this invention, related to is an anionic-cationic-nonionic surfactant, which is a compound as substantially represented by the following formula (I). As the compound, one kind or a mixture of two or more kinds at any ratio therebetween could be used.

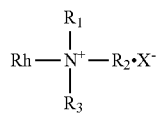
(I)

According to this invention, in the formula (I), the group $N^+$ represents a quaternary nitrogen cation, whereby introducing a quaternary ammonium group into the compound represented by the formula (I).

According to this invention, in the formula (I), the groups $R_1$ to $R_3$ may be identical with or different from one another, each independently selected from the group consisting of an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl, an optionally substituted $C_{6-50}$ aryl and a group represented by the formula -Link-(-Poly-L-Salt)$_x$. Herein, by optionally substituted, it refers to optionally substituted by one or more (for example, from 1 to 4, from 1 to 3, from 1 to 2 or 1) substituent selected from the group consisting of oxo

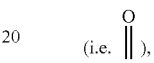

hydroxyl, a group represented by the formula -Link-(-Poly-L-Salt)$_x$, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl.

According to this invention, in the formula (I), it is required that at least one (for example, two at most) out of the groups $R_1$ to $R_3$ represents a group represented by the formula -Link-(-Poly-L-Salt)$_x$.

According to this invention, in the formula (I), the group Rh represents an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl or an optionally substituted $C_{6-50}$ aryl.

According to this invention, in the formula (I), in each definition of the groups $R_1$ to $R_3$ and the group Rh, as the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a $C_{2-20}$ linear or branched alkenyl or a $C_{8-20}$ linear or branched alkenyl, specifically octadecenyl, dodecenyl, linolyl, vinyl, propenyl or allyl, and so on. As the $C_{6-50}$ aryl, for example, there may be exemplified a $C_{6-20}$ aryl or a $C_{6-10}$ aryl, specifically phenyl or naphthyl.

According to this invention, in the formula (I), the group $X^-$ represents a halogen ion (including fluoride ion, chloride ion, bromide ion or iodide ion) or hydroxide ion (OH$^-$), wherein preference is given to a halogen ion, more preferably chloride ion.

According to this invention, in the formula (I), in the group represented by the formula -Link-(Poly-L-Salt)$_x$, the group Link represents an optionally substituted x+1 valent $C_{1-50}$ linear or branched alkyl, an optionally substituted x+1 valent $C_{5-50}$ monocyclic or polycyclic cycloalkyl, an optionally substituted x+1 valent $C_{2-50}$ linear or branched alkenyl, an optionally substituted x+1 valent $C_{6-50}$ aryl or an optionally substituted x+1 valent $C_{3-50}$ linear or branched heteroalkyl. As the optionally substituted x+1 valent $C_{1-50}$ linear or branched alkyl, it is preferably an optionally substituted x+1 valent $C_{1-20}$ linear or branched alkyl. As the optionally substituted x+1 valent $C_{5-50}$ monocyclic or polycyclic cycloalkyl, for example, there may be exemplified an optionally substituted x+1 valent $C_{5-10}$ monocyclic or polycyclic cycloalkyl, an optionally substituted x+1 valent $C_{5-8}$ monocyclic or polycyclic cycloalkyl or an optionally substituted x+1 valent $C_{5-7}$ monocyclic or polycyclic cycloalkyl, especially an optionally substituted x+1 valent $C_{5-7}$ monocyclic cycloalkyl, for example, cyclohexyl. The optionally substituted x+1 valent $C_{2-50}$ linear or branched alkenyl is preferably an optionally substituted x+1 valent $C_{2-20}$ linear or branched alkenyl. The optionally substituted x+1 valent $C_{6-50}$ aryl is preferably an optionally substituted x+1 valent $C_{6-20}$ aryl, for example, phenyl or naphthyl. The optionally substituted x+1 valent $C_{3-50}$ linear or branched heteroalkyl is preferably an optionally substituted x+1 valent $C_{3-20}$ linear or branched heteroalkyl.

According to this invention, in the formula (I), in the group represented by the -Link-(Poly-L-Salt)$_x$, plural group Poly may be identical with or different from one another, each independently represents a group represented by the formula

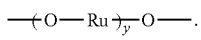

According to this invention, in the formula (I), in the group represented by the formula -Link-(Poly-L-Salt)$_x$, among plural group Poly, plural numerical value y may be identical with or different from one another, each independently represents a value from 0 to 200, preferably a value from 0 to 100. Herein, the numerical value y represents an average number of the unit —O—Ru— in the group represented by the formula

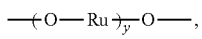

and thus could be a non-integer or an integer. As the numerical value y, for example, there may be exemplified 0, 2.0, 3.0, 3.5, 7.5, 10.0, 15.0, 25.0, 30.2, 35.0, 40.0, 45.5, 50.5, 55.2, 60.0, 75.5, 80.5, 85.0, 90.5 or 95.7, and so on.

According to this invention, in the formula (I), it is required that the sum of all (i.e. x in total) numerical values y (i.e. throughout the molecular structure of the group represented by the formula -Link-(Poly-L-Salt)$_x$ or that of the compound represented by the formula (I), the overall average number of the unit —O—Ru—) is greater than 0, but generally not greater than 200, preferably not greater than 100. In this context, throughout the molecular structure of the group represented by the formula -Link-(Poly-L-Salt)$_x$ or that of the compound represented by the formula (I), it is necessary to contain (a certain amount of) the unit —O—Ru—, so as to provide the compound represented by the formula (I) with a nonionic nature. Herein, throughout the molecular structure of the group represented by the formula -Link-(Poly-L-Salt)$_x$ or that of the compound represented by the formula (I), as the overall average number of the unit —O—Ru—, for example, there may be exemplified 0.1, 0.5, 1.5, 2.0, 3.0, 3.5, 7.5, 10.0, 15.0, 25.0, 30.2, 35.0, 40.0, 45.5, 50.5, 55.2, 60.0, 75.5, 80.5, 85.0, 90.5 or 95.7, and so on.

According to this invention, in the formula (I), among plural group Poly, plural group Ru may be identical with or different from one another, each independently represents a $C_{2-6}$ linear or branched alkylene, preferably —CH$_2$—CH$_2$—, —CH$_2$—CH(CH$_3$)— or a combination thereof, especially —CH$_2$—CH(CH$_3$)— or a combination of —CH$_2$—CH(CH$_3$)— with any other $C_{2-6}$ linear or branched alkylene.

According to this invention, in the formula (I), in the group represented by the formula

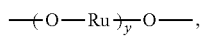

when the group Ru represents two or more out of the $C_{2-6}$ linear or branched alkylene, the (different) units —O—Ru— may bond to one another at any predetermined ratio therebetween so as to form into a random, a (di- or multi-) block or an alternative copolymer segment, with the proviso that the overall average number of these units corresponds to the numeral number y. For example, when the group Ru represents a combination of —CH$_2$—CH$_2$— and —CH$_2$—CH(CH$_3$)—, and y is 2.2, the unit —O—CH$_2$—CH$_2$ and the unit

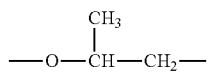

may bond to one another at any predetermined ratio therebetween (wherein for example, the ratio by molar therebetween may be from 1:99 to 99:1) so as to form into a random, a (di- or multi-) block or an alternative copolymer segment, with the proviso that the overall average number of these two units is 2.2.

According to this invention, one or more group Poly exist, and it is preferred that in at least one of the group Poly (preferably in all of the group Poly), at least a part of (or at least a certain amount of) the group Ru represents a $C_{3-6}$ linear or branched alkylene (corresponding to a non-EO unit), wherein preference is given to —CH$_2$—CH(CH$_3$)— (corresponding to a PO unit), whereby making the group Poly to preferably comprise (a certain amount of, with a upper limit value of y) the non-EO unit (for example, the unit

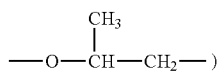

as the essential constituting unit.

According to an embodiment of this invention, in the formula (I), plural group Poly each independently or at least one of the plural group Poly represents a (diblock) ether segment represented by the following formula (I-A). Herein, as illustrated by the formula (I-A), the unit —O—CH$_2$—CH$_2$ and the unit

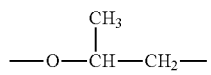

bond to each other so as to form into a (di)block copolymer segment.

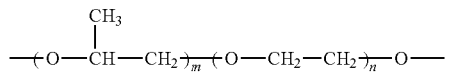
(I-A)

According to the embodiment of this invention, preferably, the ether segment and the group Link bond to each other in a manner represented by the following formula.

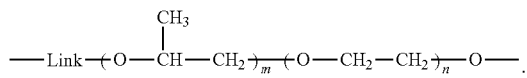

According to the embodiment of this invention, among plural group Poly (or in the group Poly), plural numerical value m may be identical with or different from one another, each independently represents a value from 0 to 100, preferably a value from 0 to 50. Herein, the numerical value m represents an average number of the unit

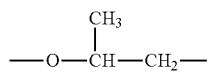

in the formula (I-A), and thus could be a non-integer or an integer. As the numerical value m, for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to the embodiment of this invention, among plural group Poly (or in the group Poly), plural numerical value n may be identical with or different from one another, each independently represents a value from 0 to 100, preferably a value from 0 to 50. Herein, the numerical value n represents an average number of the unit —O—CH$_2$—CH$_2$— in the formula (I-A), and thus could be a non-integer or an integer. As the numerical value n, for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to the embodiment of this invention, in the formula (I) or the group represented by the formula -Link—( Poly-L-Salt)$_x$, preferably, when all (i.e. x in total) of the group Poly each independently represents the (diblock) ether segment represented by the formula (I-A), the sum of all (i.e. x in total) numerical values m (i.e. throughout the molecular structure of the group represented by the formula -Link—( Poly-L-Salt)$_x$ or that of the compound represented by the formula (I), the overall average number of the unit

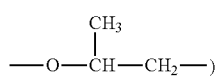)

is greater than 0, but generally not greater than 100, preferably not greater than 50. In this context, throughout the molecular structure of the group represented by the formula -Link—( Poly-L-Salt)$_x$ or that of the compound represented by the formula (I), it is preferable to contain (a certain amount of) the unit

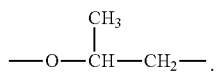

Herein, throughout the molecular structure of the group represented by the formula -Link—( Poly-L-Salt)$_x$ or that of the compound represented by the formula (I), as the overall average number of the unit

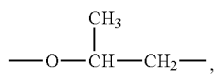, for example, there may be exemplified 0.1, 0.5, 1.2, 2.0, 2.5, 3.0, 3.5, 5.4, 7.5, 10.0, 15.0, 25.0, 30.2, 35.0, 40.0, 45.5 or 50.5, and so on.

According to the embodiment of this invention, in the formula (I) or the group represented by the formula -Link—( Poly-L-Salt)$_x$, preferably, when all (i.e. x in total) of the group Poly each independently represents the (diblock) ether segment represented by the formula (I-A), the sum of all (i.e. x in total) numerical values n (i.e. throughout the molecular structure of the group represented by the formula -Link—( Poly-L-Salt)$_x$ or that of the compound represented by the formula (I), the overall average number of the unit —O—CH$_2$—CH$_2$—) is not greater than 100, preferably not greater than 50. In this context, throughout the molecular structure of the group represented by the formula -Link—( Poly-L-Salt)$_x$ or that of the compound represented by the formula (I), it is optionally to contain (a certain amount of) the unit —O—CH$_2$—CH$_2$. Herein, throughout the molecular structure of the group represented by the formula -Link—( Poly-L-Salt)$_x$ or that of the compound represented by the formula (I), as the overall average number of the unit —O—CH$_2$—CH$_2$—, for example, there may be exemplified 0, 0.1, 0.5, 1.2, 2.0, 2.5, 3.0, 3.5, 5.4, 7.5, 10.0, 15.0, 25.0, 30.2, 35.0, 40.0, 45.5 or 49.5, and so on.

According to the embodiment of this invention, preferably, in the formula (I) or the group represented by the formula -Link—( Poly-L-Salt)$_x$, when all (i.e. x in total) the group Poly each independently represents the (diblock) ether segment represented by the formula (I-A), the sum of all (i.e. x in total) numerical values n (i.e. throughout the molecular structure of the group represented by the formula -Link—( Poly-L-Salt)$_x$ or that of the compound represented by the formula (I), the overall average number of the unit —O—CH$_2$—CH$_2$—) is greater than 0. In this context, throughout the molecular structure of the group represented by the formula -Link—( Poly-L-Salt)$_x$ or that of the compound represented by the formula (I), it is preferred to contain (a certain amount of) the unit —O—CH$_2$—CH$_2$—. Herein, throughout the molecular structure of the group represented by the formula -Link—( Poly-L-Salt)$_x$ or that of the compound represented by the formula (I), as the overall average number of the unit —O—CH$_2$—CH$_2$—, for example, there may be exemplified 0.1, 0.5, 1.2, 2.0, 2.5, 3.0, 3.5, 5.4, 7.5, 10.0, 15.0, 25.0, 30.2, 35.0, 40.0, 45.5 or 50.5, and so on.

According to the embodiment of this invention, preferably, in the formula (I) or the group represented by the formula -Link—(Poly-L-Salt)$_x$, when all (i.e. x in total) the group Poly each independently represents the (diblock) ether segment represented by the formula (I-A), the sum of all (i.e. x in total) numerical values n (i.e. throughout the molecular structure of the group represented by the formula -Link—(Poly-L-Salt)$_x$ or that of the compound represented by the formula (I), the overall average number of the unit —O—CH$_2$—CH$_2$) and all (i.e. x in total)numerical values m (i.e. throughout the molecular structure of the group represented by the formula -Link—(Poly-L-Salt)$_x$ or that of the compound represented by the formula (I), the overall average number of the unit

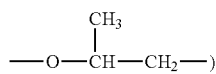

is greater than 0, but generally not greater than 200, preferably not greater than 100. In this context, throughout the molecular structure of the group represented by the formula -Link—(Poly-L-Salt)$_x$ or that of the compound represented by the formula (I), it is preferable to contain (a certain amount of) the unit —O—CH$_2$CH$_2$ and/or

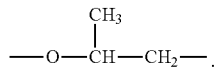

Herein, throughout the molecular structure of the group represented by the formula -Link—(Poly-L-Salt)$_x$ or that of the compound represented by the formula (I), as the overall average number of these units, for example, there may be exemplified 0.1, 0.5, 1.5, 2.0, 3.0, 3.5, 7.5, 10.0, 15.0, 25.0, 30.2, 35.0, 40.0, 45.5, 50.5, 55.2, 60.0, 75.5, 80.5, 85.0, 90.5 or 95.7, and so on.

According to this invention, in the formula (I), in the group represented by the formula -Link—(Poly-L-Salt)$_x$, plural group L may be identical with or different from one another, each independently selected from the group consisting of an optionally substituted C$_{1-10}$ linear or branched alkylene and an optionally substituted C$_{2-10}$ linear or branched alkenylene, preferably each independently represents an optionally substituted C$_{1-5}$ linear or branched alkylene.

According to this invention, in the formula (I), in the group represented by the formula -Link—(Poly-L-Salt)$_x$, plural group Salt may be identical with or different from one another, each independently represents a group represented by the formula -A$^-$(M)$_r^+$, wherein the group A$^-$ represents a carboxylate ion (COO$^-$) or a sulfonate ion (SO$_3^-$), the group M represents alkali metal (preferably Li, Na or K), alkaline earth metal (preferably Mg or Ca) or ammonium (NH$_4$); when the group M represents alkali metal or ammonium, r=1; when the group M represents alkaline earth metal, r=0.5.

According to an embodiment of this invention, in the formula (I), in the group represented by the formula -Link—(Poly-L-Salt)$_x$, depending on the total number of the group Salt, the total number of the group A$^-$ could be one or x, and it is preferred that at least one out of the group A$^-$ represents the carboxylate ion (COO$^-$). In this context, throughout the molecular structure of the compound represented by the formula (I), it is necessary to exist at least one carboxylate ion (COO$^-$).

According to this invention, in the formula (I), in the group represented by the formula -Link—(Poly-L-Salt)$_x$, the numerical value x+1 as a whole represents the valence of the group Link. Herein, the numerical value x is an integer from 1 to 10, preferably an integer from 1 to 4, for example, 1, 2 or 3.

According to this invention, in the formula (I), it is required that at least one out of the groups R$_1$, R$_2$, R$_3$ and Rh comprise in the structure a (one or more) C$_8$ linear moiety, whereby providing the anionic-cationic-nonionic surfactant of this invention with anticipated surface active performances.

According to this invention, in the formula (I), unless otherwise expressively specified, by optionally substituted, it refers to optionally substituted by one or more (for example, from 1 to 5, from 1 to 4, from 1 to 3, from 1 to 2 or 1) substituent selected from the group consisting of oxo

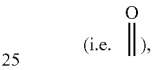

hydroxyl, a C$_{1-20}$ linear or branched alkyl, a C$_{5-10}$ monocyclic or polycyclic cycloalkyl, a C$_{2-20}$ linear or branched alkenyl and a C$_{6-20}$ aryl. As the C$_{1-20}$ linear or branched alkyl, for example, there may be exemplified a C$_{1-10}$ linear or branched alkyl or a C$_{1-6}$ linear or branched alkyl, or methyl or ethyl, and so on. As the C$_{5-10}$ monocyclic or polycyclic cycloalkyl, for example, there may be exemplified a C$_{5-8}$ monocyclic or polycyclic cycloalkyl or a C$_{5-7}$ monocyclic or polycyclic cycloalkyl, especially a C$_{5-7}$ monocyclic cycloalkyl, specifically cyclopentyl or cyclohexyl. As the C$_{2-20}$ linear or branched alkenyl, for example, there may be exemplified a C$_{2-10}$ linear or branched alkenyl, specifically vinyl, propenyl or allyl, and so on. As the C$_{6-20}$ aryl, for example, there may be exemplified a C$_{6-10}$ aryl, specifically phenyl or naphthyl.

According to this invention, in the formula (I), when oxo exists as the substituent, it is preferred that at least one oxo exists on the carbon atom directly bonding to a N atom (if any, for example, that contained in a linear or branched heteroalkyl), so as to make the carbon atom to present in the form of carbonyl (i.e.

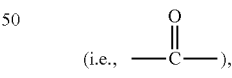

whereby introducing a structure of carbonyl directly bonding to a N atom (for example, imido) into the molecular structure of the compound represented by the formula (I). Further, to provide better hydrolysis resistance or chemical resistance, it is preferred that there is no oxo as the substituent on at least a part (preferably all) of the carbon atoms directly bonding to an O or S atom (if any), and/or, on at least a part of (preferably all) of the terminal carbon atoms (i.e. The carbon atom at a free end of and/or a un-bonded position on the molecular chain), and/or, two carbon atoms directly bonding to each other are not substituted by oxo simultaneously. By doing so, no chemically active or unstable group like an ester or aldehyde group will be introduced into the molecular structure of the compound represented by the formula (I). Specifically, assuming that the group Link represents a 2 valent linear alkyl

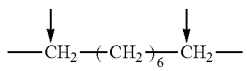

(comprising two terminal carbon atoms as indicated by the arrow marks in the formula) substituted by one oxo, according to the aforesaid rules, this group would be preferably

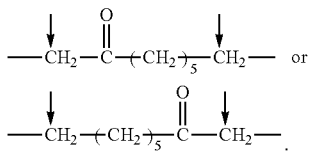

Or, assuming that the group Link is a 2 valent branched heteroalkyl

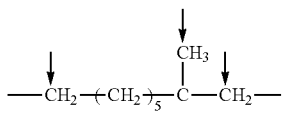

(comprising three terminal carbon atoms as indicated by the arrow marks in the formula, also comprising three carbon atoms directly bonding to a N atom) substituted by one oxo, according to the aforesaid rules, this group would be preferably

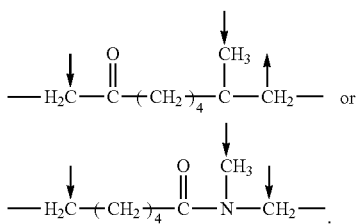

According to this invention, as the anionic-cationic-nonionic surfactant or the compound represented by the formula (I), for example, there may be exemplified a compound as substantially represented by the following formula (I-1), a compound as substantially represented by the following formula (I-2), a compound as substantially represented by the following formula (I-3) or a compound as substantially represented by the following formula (I-4). As these compounds, one kind or a mixture of two or more kinds at any ratio therebetween could be used.

According to the embodiment of this invention, it is required that at least one (for example, 1, 2, 3 or 4, and so on) N atom contained in the molecular structure of these compounds bond to an additional group Rh and an additional group X (not shown in the following formula (I-1), (I-2), (I-3) or (I-4)), whereby presenting as a quaternary ammonium salt/hydroxide group represented by the formula

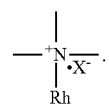

In the formula

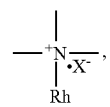

the group $N^+$ represents the quaternary cation form of the at least one N atom, the group Rh represents an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl or an optionally substituted $C_{6-50}$ aryl. In the definition of the group Rh, as the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a $C_{2-20}$ linear or branched alkenyl or a $C_{8-20}$ linear or branched alkenyl, specifically octadecenyl, dodecenyl, linolyl, vinyl, propenyl or allyl, and so on. As the $C_{6-50}$ aryl, for example, there may be exemplified a $C_{6-20}$ aryl or a $C_6$-10 aryl, specifically phenyl or naphthyl. The group $X^-$ represents a halogen ion (including fluoride ion, chloride ion, bromide ion or iodide ion) or hydroxide ion ($OH^-$), wherein preference is given to a halogen ion, more preferably chloride ion. Herein, by optionally substituted, it refers to optionally substituted by one or more (for example, from 1 to 4, from 1 to 3, from 1 to 2 or 1) substituent selected from the group consisting of hydroxyl, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl.

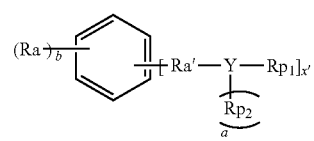

According to this invention, in the formula (I-1), plural group Ra may be identical with or different from one another, each independently selected from the group consisting of hydrogen, an optionally substituted $C_{1-20}$ linear or branched alkyl, an optionally substituted $C_{2-20}$ linear or branched alkenyl and an optionally substituted $C_{6-10}$ aryl, preferably of hydrogen, an optionally substituted $C_{8-20}$ linear or branched alkyl and an optionally substituted $C_{6-10}$ aryl.

According to this invention, in the formula (I-1), plural group Ra' may be identical with or different from one another, each independently selected from the group consisting of a single bond, an optionally substituted $C_{1-10}$ linear or branched alkylene, an optionally substituted $C_{2-10}$ linear or branched alkenylene, carbonyl, an optionally substituted $C_{1-10}$ linear or branched alkylene carbonyl and an optionally substituted $C_{2-10}$ linear or branched alkenylene carbonyl, preferably each independently selected from the group consisting of a single bond and an optionally substituted $C_{1-6}$ linear or branched alkylene.

According to this invention, in the formula (I-1), the numerical value b represents an integer from 1 to 3, preferably 1.

According to this invention, in the formula (I-1), the numerical value x' represents the number of the group

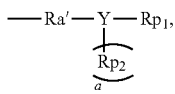

which is an integer from 1 to 5, preferably an integer from 1 to 4, for example, 1, 2 or 3. Obviously, $b+x' \leq 6$.

According to this invention, in the formula (I-1), plural group Y may be identical with or different from one another, each independently selected from the group consisting of N and O, with the proviso that when the group Y represents N, a=1, when the group Y represents O, a=0. Further, at least one of the group Y represents N.

According to this invention, in the formula (I-1), plural (i.e. x' in total) group $Rp_1$ may be identical with or different from one another, each independently selected from the group consisting of a group represented by the formula

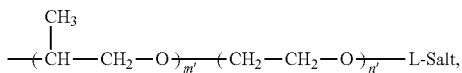

hydrogen, an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl and an optionally substituted $C_{6-50}$ aryl, with the proviso that at least one (for example, one or two) of the groups $Rp_1$ represents a group represented by the formula

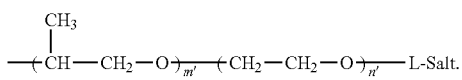

As the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a $C_{2-20}$ linear or branched alkenyl or a $C_{8-20}$ linear or branched alkenyl, specifically octadecenyl, dodecenyl, linolyl, vinyl, propenyl or allyl, and so on. As the $C_{6-50}$ aryl, for example, there may be exemplified a $C_{6-20}$ aryl or a $C_{6-10}$ aryl, specifically phenyl or naphthyl. Herein, by optionally substituted, it refers to optionally substituted by one or more (for example, from 1 to 4, from 1 to 3, from 1 to 2 or 1) substituent selected from the group consisting of hydroxyl, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl.

According to this invention, in the formula (I-1), plural (i.e. x'×a in total) group $Rp_2$ may be identical with or different from one another, each independently selected from the group consisting of a group represented by the formula

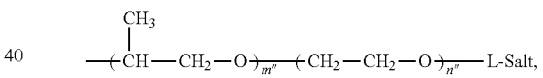

hydrogen, an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl and an optionally substituted $C_{6-50}$ aryl. As the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a $C_{2-20}$ linear or branched alkenyl or a $C_{8-20}$ linear or branched alkenyl, specifically octadecenyl, dodecenyl, linolyl, vinyl, propenyl or allyl, and so on. As the $C_{6-50}$ aryl, for example, there may be exemplified a $C_{6-20}$ aryl or a $C_{6-10}$ aryl, specifically phenyl or naphthyl. Herein, by optionally substituted, it refers to optionally substituted by one or more (for example, from 1 to 4, from 1 to 3, from 1 to 2 or 1) substituent selected from the group consisting of hydroxyl, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl.

According to this invention, in the formula (I-1), plural numerical value m' may be identical with or different from one another, each independently represents a value from 0 to 100, preferably a value from 0 to 50. Herein, the numerical value m' represents an average number of the unit

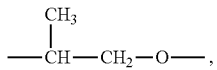

and thus could be a non-integer or an integer. As the numerical value m', for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-1), plural numerical value n' may be identical with or different from one another, each independently represents a value from 0 to 100, preferably a value from 0 to 50. Herein, the numerical value n' represents an average number of the unit —$CH_2$—$CH_2$—O and thus could be a non-integer or an integer. As the numerical value n', for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-1), plural numerical value m" may be identical with or different from one another, each independently represents a value from 0 to 100, preferably a value from 0 to 50. Herein, the numerical value m" represents an average number of the unit

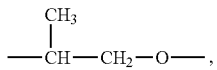

and thus could be a non-integer or an integer. As the numerical value m", for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-1), plural numerical value n" may be identical with or different from one another, each independently represents a value from 0 to 100, preferably a value from 0 to 50. Herein, the numerical value n" represents an average number of the unit —$CH_2$—$CH_2$—O— and thus could be a non-integer or an integer. As the numerical value n", for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-1), it is preferable that the sum of all (i.e. corresponding to x') numerical values m' and all (i.e. corresponding to x'×a) numerical values m" (i.e. throughout the molecular structure of the compound represented by the formula (I-1), the overall average number of the unit

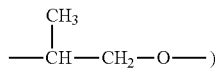

is greater than 0 but generally not greater than 100, preferably greater than 0 but not greater than 50. In this context, throughout the molecular structure of the compound represented by the formula (I-1), it is preferable to contain (a certain amount of) the unit

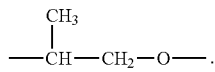

Herein, throughout the molecular structure of the compound represented by the formula (I-1), as the overall average number of the unit

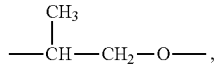

for example, there may be exemplified 0.1, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-1), it is preferable that the sum of all (i.e. corresponding to x') numerical value n' and all (i.e. corresponding to x'×a) numerical value n" (i.e. throughout the molecular structure of the compound represented by the formula (I-1), the overall average number of the unit —$CH_2$—$CH_2$—O—) is not greater than 100, preferably not greater than 50. As the overall average number of the unit —$CH_2$—$CH_2$—O—, for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to an embodiment of this invention, preferably, in the formula (I-1), the sum of all (i.e. corresponding to x') numerical value n' and all (i.e. corresponding to x'×a) numerical values n" (i.e. throughout the molecular structure of the compound represented by the formula (I-1), the overall average number of the unit —$CH_2$—$CH_2$—O—) is greater than 0. In this context, throughout the molecular structure of the compound represented by the formula (I-1), it is preferred to contain (a certain amount of) the unit —$CH_2$—$CH_2$—O—. Herein, throughout the molecular structure of the compound represented by the formula (I-1), as the overall average number of the unit —$CH_2$—$CH_2$—O— for example, there may be exemplified 0.1, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-1), the sum of all (i.e. corresponding to x') numerical value n' and all (i.e. corresponding to x'×a) numerical values n" (i.e. throughout the molecular structure of the compound represented by the formula (I-1), the overall average number of the unit —$CH_2$—$CH_2$—O—) plus the sum of all (i.e. corresponding to x') numerical values m' and all (i.e. corresponding to x'×a) numerical values m" (i.e. throughout the molecular structure of the compound represented by the formula (I-1), the overall average number of the unit

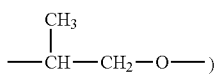

is greater than 0 but generally not greater than 200, preferably not greater than 100. In this context, throughout the molecular structure of the compound represented by the formula (I-1), it is necessary to contain (a certain amount of) the unit —O—CH$_2$—CH$_2$— and/or

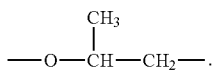

Herein, throughout the molecular structure of the compound represented by the formula (I-1), as the overall average number of these units, for example, there may be exemplified 0.1, 0.5, 1.5, 2.0, 3.0, 3.5, 7.5, 10.0, 15.0, 25.0, 30.2, 35.0, 40.0, 45.5, 50.5, 55.2, 60.0, 75.5, 80.5, 85.0, 90.5 or 95.7, and so on.

According to this invention, in the formula (I-1), plural group L may be identical with or different from one another, each independently selected from the group consisting of an optionally substituted $C_{1-10}$ linear or branched alkylene and an optionally substituted $C_{2-10}$ linear or branched alkenylene, preferably each independently represents an optionally substituted $C_{1-5}$ linear or branched alkylene.

According to this invention, in the formula (I-1), plural group Salt may be identical with or different from one another, each independently represents a group represented by the formula -A$^-$(M)$_r^+$, wherein the group A$^-$ represents a carboxylate ion (COO$^-$) or a sulfonate ion (SO$_3^-$), the group M represents alkali metal (preferably Li, Na or K), alkaline earth metal (preferably Mg or Ca) or ammonium (NH$_4$). When the group M represents alkali metal or ammonium, r=1; when the group M represents alkaline earth metal, r=0.5.

According to this invention, in the formula (I-1), it is required that at least one (for example, 1, 2 or 3) out of the groups Ra and Rh (covering all groups Ra and all groups Rh contained in the compound represented by the formula (I-1), obviously further comprising the group Rh in the aforesaid quaternary ammonium salt/hydroxide group) comprise in its molecular structure (one or more) $C_8$ linear moiety, whereby providing the compound represented by the formula (I-1) with anticipated surface active performances.

According to an embodiment of this invention, in the formula (I-1), depending on the total number of the group Salt, the group A$^-$ could be one or more in number, wherein at least one out of the group A$^-$ represents the carboxylate ion (COO$^-$). In this context, throughout the molecular structure of the compound represented by the formula (I-1), it is preferable to exist at least one carboxylate ion (COO$^-$).

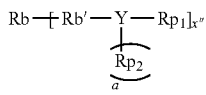

According to this invention, in the formula (I-2), the group Rb represents an optionally substituted $C_{1-49}$ linear or branched alkyl, an optionally substituted $C_{5-49}$ monocyclic or polycyclic cycloalkyl or an optionally substituted $C_{2-49}$ linear or branched alkenyl, preferably an optionally substituted $C_{1-29}$ linear or branched alkyl, an optionally substituted $C_{5-10}$ monocyclic or polycyclic cycloalkyl or an optionally substituted $C_{2-29}$ linear or branched alkenyl, or represents an optionally substituted $C_{8-29}$ linear or branched alkyl, an optionally substituted $C_{5-8}$ monocyclic or polycyclic cycloalkyl or an optionally substituted $C_{8-29}$ linear or branched alkenyl, preferably an optionally substituted $C_{8-19}$ linear or branched alkyl, an optionally substituted $C_{5-7}$ monocyclic cycloalkyl (for example, cyclohexyl) or an optionally substituted $C_{8-19}$ linear or branched alkenyl.

According to this invention, in the formula (I-2), plural group Rb' may be identical with or different from one another, each independently selected from the group consisting of a single bond and carbonyl.

According to this invention, in the formula (I-2), plural group Y may be identical with or different from one another, each independently selected from the group consisting of N and O, with the proviso that when the group Y represents N, a=1, when the group Y represents O, a=0. Further, at least one of the group Y represents N.

According to this invention, in the formula (I-2), the numerical value x" represents the number of the group

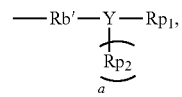

which is an integer from 1 to 10, preferably an integer from 1 to 4, for example, 1, 2 or 3.

According to this invention, in the formula (I-2), plural (i.e. x" in total) group Rp$_1$ may be identical with or different from one another, each independently selected from the group consisting of a group represented by the formula

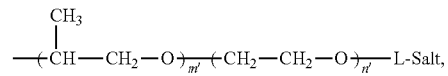

hydrogen, an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl and an optionally substituted $C_{6-50}$ aryl, with the proviso that at least one (for example, one or two) of the groups Rp$_1$ represents a group represented by the formula

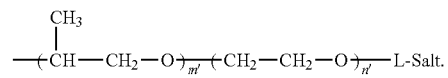

As the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a C$_{2-20}$ linear or branched alkenyl or a C$_{8-20}$ linear or branched alkenyl, specifically octadecenyl, dodecenyl, linolyl, vinyl, propenyl or allyl, and so on. As the C$_{6-50}$ aryl, for example, there may be exemplified a C$_{6-20}$ aryl or a C$_{6-10}$ aryl, specifically phenyl or naphthyl. Herein, by optionally substituted, it refers to optionally substituted by one or more (for example, from 1 to 4, from 1 to 3, from 1 to 2 or 1) substituent selected from the group consisting of hydroxyl, a C$_{1-20}$ linear or branched alkyl, a C$_{5-10}$ monocyclic or polycyclic cycloalkyl, a C$_{2-20}$ linear or branched alkenyl and a C$_{6-20}$ aryl. As the C$_{1-20}$ linear or branched alkyl, for example, there may be exemplified a C$_{1-10}$ linear or branched alkyl or a C$_{1-6}$ linear or branched alkyl, or methyl or ethyl, and so on. As the C$_{5-10}$ monocyclic or polycyclic cycloalkyl, for example, there may be exemplified a C$_{5-8}$ monocyclic or polycyclic cycloalkyl or a C$_{5-7}$ monocyclic or polycyclic cycloalkyl, especially a C$_{5-7}$ monocyclic cycloalkyl, specifically cyclopentyl or cyclohexyl. As the C$_{2-20}$ linear or branched alkenyl, for example, there may be exemplified a C$_{2-10}$ linear or branched alkenyl, specifically vinyl, propenyl or allyl, and so on. As the C$_{6-20}$ aryl, for example, there may be exemplified a C$_{6-10}$ aryl, specifically phenyl or naphthyl.

According to this invention, in the formula (I-2), plural (i.e. x"×a in total) group Rp$_2$ may be identical with or different from one another, each independently selected from the group consisting of a group represented by the formula

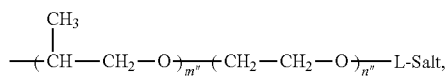

hydrogen, an optionally substituted C$_{1-50}$ linear or branched alkyl, an optionally substituted C$_{5-50}$ monocyclic or polycyclic cycloalkyl, an optionally substituted C$_{2-50}$ linear or branched alkenyl and an optionally substituted C$_{6-50}$ aryl. As the C$_{1-50}$ linear or branched alkyl, for example, there may be exemplified a C$_{1-20}$ linear or branched alkyl or a C$_{8-20}$ linear or branched alkyl, specifically octadecyl, lauryl, octyl, hexadecyl, hexyl, methyl or ethyl, and so on. As the C$_{5-50}$ monocyclic or polycyclic cycloalkyl, for example, there may be exemplified a C$_{5-10}$ monocyclic or polycyclic cycloalkyl, a C$_{5-8}$ monocyclic or polycyclic cycloalkyl or a C$_{5-7}$ monocyclic or polycyclic cycloalkyl, especially a C$_{5-7}$ monocyclic cycloalkyl, specifically cyclopentyl or cyclohexyl. As the C$_{2-50}$ linear or branched alkenyl, for example, there may be exemplified a C$_{2-20}$ linear or branched alkenyl or a C$_{8-20}$ linear or branched alkenyl, specifically octadecenyl, dodecenyl, linolyl, vinyl, propenyl or allyl, and so on. As the C$_{6-50}$ aryl, for example, there may be exemplified a C$_{6-20}$ aryl or a C$_{6-10}$ aryl, specifically phenyl or naphthyl. Herein, by optionally substituted, it refers to optionally substituted by one or more (for example, from 1 to 4, from 1 to 3, from 1 to 2 or 1) substituent selected from the group consisting of hydroxyl, a C$_{1-20}$ linear or branched alkyl, a C$_{5-10}$ monocyclic or polycyclic cycloalkyl, a C$_{2-20}$ linear or branched alkenyl and a C$_{6-20}$ aryl. As the C$_{1-20}$ linear or branched alkyl, for example, there may be exemplified a C$_{1-10}$ linear or branched alkyl or a C$_{1-6}$ linear or branched alkyl, or methyl or ethyl, and so on. As the C$_{5-10}$ monocyclic or polycyclic cycloalkyl, for example, there may be exemplified a C$_{5-8}$ monocyclic or polycyclic cycloalkyl or a C$_{5-7}$ monocyclic or polycyclic cycloalkyl, especially a C$_{5-7}$ monocyclic cycloalkyl, specifically cyclopentyl or cyclohexyl. As the C$_{2-20}$ linear or branched alkenyl, for example, there may be exemplified a C$_{2-10}$ linear or branched alkenyl, specifically vinyl, propenyl or allyl, and so on. As the C$_{6-20}$ aryl, for example, there may be exemplified a C$_{6-10}$ aryl, specifically phenyl or naphthyl.

According to this invention, in the formula (I-2), plural numerical value m' may be identical with or different from one another, each independently represents a value from 0 to 100, preferably a value from 0 to 50. Herein, the numerical value m' represents an average number of the unit

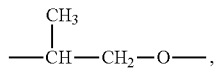

and thus could be a non-integer or an integer. As the numerical value m', for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-2), plural numerical value n' may be identical with or different from one another, each independently represents a value from 0 to 100, preferably a value from 0 to 50. Herein, the numerical value n' represents an average number of the unit —CH$_2$—CH$_2$—O— and thus could be a non-integer or an integer. As the numerical value n', for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-2), plural numerical value m" may be identical with or different from one another, each independently represents a value from 0 to 100, preferably a value from 0 to 50. Herein, the numerical value m" represents an average number of the unit

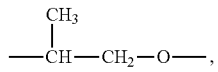

and thus could be a non-integer or an integer. As the numerical value m", for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-2), plural numerical value n" may be identical with or different from one another, each independently represents a value from 0 to 100, preferably a value from 0 to 50. Herein, the numerical value n" represents an average number of the unit —CH$_2$—CH$_2$—O— and thus could be a non-integer or an integer. As the numerical value n", for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-2), it is preferable that the sum of all (i.e. corresponding to x") numerical values m' and all (i.e. corresponding to x"×a) numerical values m" (i.e. throughout the molecular structure of the compound represented by the formula (I-2), the overall average number of the unit

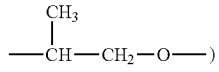

is greater than 0 but generally not greater than 100, preferably greater than 0 but not greater than 50. In this context, throughout the molecular structure of the compound represented by the formula (I-2), it is preferably to contain (a certain amount of) the unit

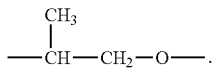

Herein, throughout the molecular structure of the compound represented by the formula (I-2), as the overall average number of the unit

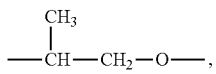

for example, there may be exemplified 0.1, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-2), it is preferable that the sum of all (i.e. corresponding to x") numerical values n' and all (i.e. corresponding to x"×a) numerical values n" (i.e. throughout the molecular structure of the compound represented by the formula (I-2), the overall average number of the unit $—CH_2—CH_2—O—$) is not greater than 100, preferably not greater than 50. As the overall average number of the unit $—CH_2—CH_2—O—$, for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to an embodiment of this invention, preferably, in the formula (I-2), the sum of all (i.e. corresponding to x") numerical values n' and all (i.e. corresponding to x"×a) numerical values n" (i.e. throughout the molecular structure of the compound represented by the formula (I-2), the overall average number of the unit $—CH_2—CH_2—O—$) is greater than 0. In this context, throughout the molecular structure of the compound represented by the formula (I-2), it is preferred to contain (a certain amount of) the unit $—CH_2—CH_2—O—$. Herein, throughout the molecular structure of the compound represented by the formula (I-2), as the overall average number of the unit $—CH_2—CH_2—O—$, for example, there may be exemplified 0.1, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-2), the sum of all (i.e. corresponding to x") numerical value n' and all (i.e. corresponding to x"×a) numerical values n" (i.e. throughout the molecular structure of the compound represented by the formula (I-2), the overall average number of the unit $—CH_2—CH_2—O—$) plus sum of all (i.e. corresponding to x") numerical values m' and all (i.e. corresponding to x"×a) numerical values m" (i.e. throughout the molecular structure of the compound represented by the formula (I-2), the overall average number of the unit

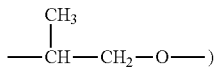

is greater than 0 but generally not greater than 200, preferably not greater than 100. In this context, throughout the molecular structure of the compound represented by the formula (I-2), it is necessary to contain (a certain amount of) the unit $—CH_2—CH_2—O—$ and/or

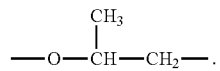

Herein, throughout the molecular structure of the compound represented by the formula (I-2), as the overall average number of these units, for example, there may be exemplified 0.1, 0.5, 1.5, 2.0, 3.0, 3.5, 7.5, 10.0, 15.0, 25.0, 30.2, 35.0, 40.0, 45.5, 50.5, 55.2, 60.0, 75.5, 80.5, 85.0, 90.5 or 95.7, and so on.

According to this invention, in the formula (I-2), plural group L may be identical with or different from one another, each independently selected from the group consisting of an optionally substituted $C_{1-10}$ linear or branched alkylene and an optionally substituted $C_{2-10}$ linear or branched alkenylene, preferably each independently represents an optionally substituted $C_{1-5}$ linear or branched alkylene.

According to this invention, in the formula (I-2), plural group Salt may be identical with or different from one another, each independently represents a group represented by the formula $-A^-(M)_r^+$, wherein the group $A^-$ represents a carboxylate ion ($COO^-$) or a sulfonate ion ($SO_3^-$), the group M represents alkali metal (preferably Li, Na or K), alkaline earth metal (preferably Mg or Ca) or ammonium ($NH_4$). When the group M represents alkali metal or ammonium, r=1; when the group M represents alkaline earth metal, r=0.5.

According to an embodiment of this invention, in the formula (I-2), depending on the total number of the group Salt, the group $A^-$ could be one or more in number, wherein at least one out of the group $A^-$ represents the carboxylate ion ($COO^-$). In this context, throughout the molecular structure of the compound represented by the formula (I-2), it is preferable to exist at least one carboxylate ion ($COO^-$).

According to this invention, in the formula (I-2), it is required that at least one (for example, 1, 2 or 3) out of the groups Rb and Rh (covering all groups Rb and all groups Rh contained in the compound represented by the formula (I-2), obviously further comprising the group Rh in the aforesaid quaternary ammonium salt/hydroxide group) comprise in its molecular structure (one or more) $C_8$ linear moiety, whereby providing the compound represented by the formula (I-2) with anticipated surface active performances.

(I-3)

According to this invention, in the formula (I-3), plural group Rc may be identical with or different from one another, each independently selected from the group consisting of an optionally substituted $C_{1-20}$ linear or branched alkyl, an optionally substituted $C_{2-20}$ linear or branched alkenyl, an optionally substituted $C_{1-20}$ linear or branched alkyl carbonyl and an optionally substituted $C_{2-20}$ linear or branched alkenyl carbonyl, or each independently selected from the group consisting of an optionally substituted $C_{1-10}$ linear or branched alkyl, an optionally substituted $C_{2-10}$ linear or branched alkenyl, an optionally substituted $C_{1-10}$ linear or branched alkyl carbonyl and an optionally substituted $C_{2-10}$ linear or branched alkenyl carbonyl, or each independently selected from the group consisting of an optionally substituted $C_{8-20}$ linear or branched alkyl, an optionally substituted $C_{8-20}$ linear or branched alkenyl, an optionally substituted $C_{8-20}$ linear or branched alkyl carbonyl and an optionally substituted $C_{8-20}$ linear or branched alkenyl carbonyl.

According to this invention, in the formula (I-3), plural group Rd may be identical with or different from one another, each independently selected from the group consisting of an optionally substituted $C_{1-10}$ linear or branched alkylene, an optionally substituted $C_{2-10}$ linear or branched alkenylene, an optionally substituted $C_{1-10}$ linear or branched alkylene carbonyl, an optionally substituted $C_{2-10}$ linear or branched alkenylene carbonyl, an optionally substituted carbonyl $C_{1-10}$ linear or branched alkylene carbonyl and an optionally substituted carbonyl $C_{2-10}$ linear or branched alkenylene carbonyl, preferably each independently selected from the group consisting of an optionally substituted $C_{1-5}$ linear or branched alkylene and an optionally substituted $C_{1-5}$ linear or branched alkylene carbonyl.

According to this invention, in the formula (I-3), the numerical value x' represents the number of the unit

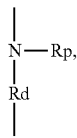

which is an integer from 1 to 10, preferably an integer from 1 to 4, for example, 1, 2 or 3.

According to this invention, in the formula (I-3), plural (i.e. x' in total) group Rp may be identical with or different from one another, each independently selected from the group consisting of a group represented by the formula

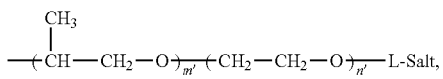

hydrogen, an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl and an optionally substituted $C_{6-50}$ aryl, with the proviso that at least one (for example, one or two) of the groups Rp represents a group represented by the formula

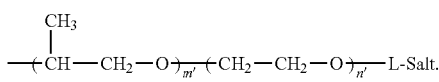

As the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a $C_{2-20}$ linear or branched alkenyl or a $C_{8-20}$ linear or branched alkenyl, specifically octadecenyl, dodecenyl, linolyl, vinyl, propenyl or allyl, and so on. As the $C_{6-50}$ aryl, for example, there may be exemplified a $C_{6-20}$ aryl or a $C_{6-10}$ aryl, specifically phenyl or naphthyl. Herein, by optionally substituted, it refers to optionally substituted by one or more (for example, from 1 to 4, from 1 to 3, from 1 to 2 or 1) substituent selected from the group consisting of hydroxyl, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl.

According to this invention, in the formula (I-3), plural numerical value m' may be identical with or different from one another, each independently represents a value from 0 to 100, preferably a value from 0 to 50. Herein, the numerical value m' represents an average number of the unit

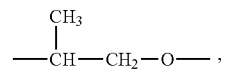

and thus could be a non-integer or an integer. As the numerical value m', for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-3), plural numerical value n' may be identical with or different from one another, each independently represents a value from 0 to 100, preferably a value from 0 to 50. Herein, the numerical value n' represents an average number of the unit —$CH_2$—$CH_2$—O— and thus could be a non-integer or an integer. As the numerical value n', for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-3), it is preferred that the sum of all (i.e. corresponding to x''') numerical values m' (i.e. throughout the molecular structure of the compound represented by the formula (I-3), the overall average number of the unit

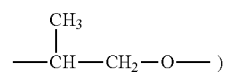

is greater than 0 but generally not greater than 100, preferably not greater than 50. In this context, throughout the molecular structure of the compound represented by the formula (I-3), it is preferable to contain (a certain amount of) the unit

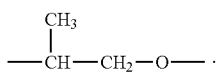

Herein, throughout the molecular structure of the compound represented by the formula (I-3), as the overall average number of the unit

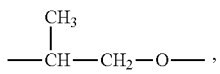

for example, there may be exemplified 0.1, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-3), it is preferred that the sum of all (i.e. corresponding to x''') numerical values n' (i.e. throughout the molecular structure of the compound represented by the formula (I-3), the overall average number of the unit —$CH_2$—$CH_2$—O—) is not greater than 100, preferably not greater than 50. As the overall average number of the unit —$CH_2$—$CH_2$—O—, for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to an embodiment of this invention, preferably, in the formula (I-3), the sum of all (i.e. corresponding to x''') numerical values n' (i.e. throughout the molecular structure of the compound represented by the formula (I-3), the overall average number of the unit —$CH_2$—$CH_2$—O—) is greater than 0. In this context, throughout the molecular structure of the compound represented by the formula (I-3), it is preferred to contain (a certain amount of) the unit —$CH_2$—$CH_2$—O—. Herein, throughout the molecular structure of the compound represented by the formula (I-3), as the overall average number of the unit —$CH_2$—$CH_2$—O—, for example, there may be exemplified 0.1, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-3), the sum of all (i.e. corresponding to x''') numerical value n' (i.e. throughout the molecular structure of the compound represented by the formula (I-3), the overall average number of the unit —$CH_2$—$CH_2$—O—) plus the sum of all (i.e. corresponding to x''') numerical values m' (i.e. throughout the molecular structure of the compound represented by the formula (I-3), the overall average number of the unit

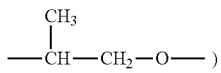

is greater than 0 but generally not greater than 200, preferably not greater than 100. In this context, throughout the molecular structure of the compound represented by the formula (I-3), it is necessary to contain (a certain amount of) the unit —$CH_2$—$CH_2$—O— and/or

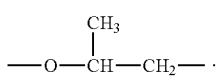

Herein, throughout the molecular structure of the compound represented by the formula (I-3), as the overall average number of these units, for example, there may be exemplified 0.1, 0.5, 1.5, 2.0, 3.0, 3.5, 7.5, 10.0, 15.0, 25.0, 30.2, 35.0, 40.0, 45.5, 50.5, 55.2, 60.0, 75.5, 80.5, 85.0, 90.5 or 95.7, and so on.

According to this invention, in the formula (I-3), plural group L may be identical with or different from one another, each independently selected from the group consisting of an optionally substituted $C_{1-10}$ linear or branched alkylene and an optionally substituted $C_{2-10}$ linear or branched alkenylene, preferably each independently represents an optionally substituted $C_{1-5}$ linear or branched alkylene.

According to this invention, in the formula (I-3), plural group Salt may be identical with or different from one another, each independently represents a group represented by the formula -$A^-(M)_r^+$, wherein the group $A^-$ represents a carboxylate ion ($COO^-$) or a sulfonate ion ($SO_3^-$), the group M represents alkali metal (preferably Li, Na or K), alkaline earth metal (preferably Mg or Ca) or ammonium ($NH_4$). When the group M represents alkali metal or ammonium, r=1; when the group M represents alkaline earth metal, r=0.5.

According to an embodiment of this invention, in the formula (I-3), depending on the total number of the group Salt, the group $A^-$ could be one or more in number, wherein at least one out of the group $A^-$ represents the carboxylate ion ($COO^-$). In this context, throughout the molecular structure of the compound represented by the formula (I-3), it is preferred to exist at least one carboxylate ion ($COO^-$).

According to this invention, in the formula (I-3), it is required that at least one (for example, 1, 2 or 3) out of the groups Rc and Rh (covering all groups Rc and all groups Rh contained in the compound represented by the formula (I-3), obviously further comprising the group Rh in the aforesaid quaternary ammonium salt/hydroxide group) comprise in its molecular structure (one or more) $C_8$ linear moiety, whereby providing the compound represented by the formula (I-3) with anticipated surface active performances.

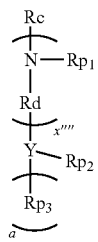

(I-4)

According to this invention, in the formula (I-4), the group Rc represents an optionally substituted $C_{1-20}$ linear or branched alkyl, an optionally substituted $C_{2-20}$ linear or branched alkenyl, an optionally substituted $C_{1-20}$ linear or branched alkyl carbonyl or an optionally substituted $C_{2-20}$ linear or branched alkenyl carbonyl, or an optionally substituted $C_{1-10}$ linear or branched alkyl, an optionally substituted $C_{2-10}$ linear or branched alkenyl, an optionally substituted $C_{1-10}$ linear or branched alkyl carbonyl or an optionally substituted $C_{2-10}$ linear or branched alkenyl carbonyl, or an optionally substituted $C_{5-20}$ linear or branched alkyl, an optionally substituted $C_{5-20}$ linear or branched alkenyl, an optionally substituted $C_{5-20}$ linear or branched alkyl carbonyl or an optionally substituted $C_{5-20}$ linear or branched alkenyl carbonyl.

According to this invention, in the formula (I-4), plural group Rd may be identical with or different from one another, each independently selected from the group consisting of an optionally substituted $C_{1-10}$ linear or branched alkylene, an optionally substituted $C_{2-10}$ linear or branched alkenylene, an optionally substituted $C_{1-10}$ linear or branched alkylene carbonyl, an optionally substituted $C_{2-10}$ linear or branched alkenylene carbonyl, an optionally substituted carbonyl $C_{1-10}$ linear or branched alkylene carbonyl and an optionally substituted carbonyl $C_{2-10}$ linear or branched alkenylene carbonyl, preferably each independently selected from the group consisting of an optionally substituted $C_{1-5}$ linear or branched alkylene and an optionally substituted $C_{1-5}$ linear or branched alkylene carbonyl.

According to this invention, in the formula (I-4), the group Y represents N or O, with the proviso that when the group Y represents N, a=1, when the group Y represents O, a=0.

According to this invention, in the formula (I-4), the numerical value x' represents the number of the unit

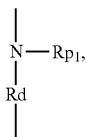

which is an integer from 1 to 9, preferably an integer from 1 to 3, more preferably 1 or 2.

According to this invention, in the formula (I-4), plural (i.e. x'''' in total) group $Rp_1$ may be identical with or different from one another, each independently selected from the group consisting of a group represented by the formula

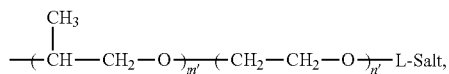

hydrogen, an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl and an optionally substituted $C_{6-50}$ aryl, with the proviso that at least one (for example, one or two) of the groups $Rp_1$ represents a group represented by the formula

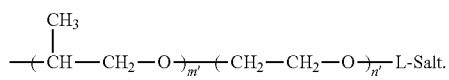

As the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a $C_{2-20}$ linear or branched alkenyl or a $C_{8-20}$ linear or branched alkenyl, specifically octadecenyl, dodecenyl, linolyl, vinyl, propenyl or allyl, and so on. As the $C_{6-50}$ aryl, for example, there may be exemplified a $C_{6-20}$ aryl or a $C_{6-10}$ aryl, specifically phenyl or naphthyl. Herein, by optionally substituted, it refers to optionally substituted by one or more (for example, from 1 to 4, from 1 to 3, from 1 to 2 or 1) substituent selected from the group consisting of hydroxyl, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl.

According to this invention, in the formula (I-4), the group $Rp_2$ may be selected from the group consisting of a group represented by the formula

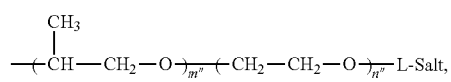

hydrogen, an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl and an optionally substituted $C_{6-50}$ aryl. As the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a $C_{2-20}$ linear or branched alkenyl or a $C_{8-20}$ linear or branched alkenyl, specifically octadecenyl, dodecenyl, linolyl, vinyl, propenyl or allyl, and so on. As the $C_{6-50}$ aryl, for example, there may be exemplified a $C_{6-20}$ aryl or a $C_{6-10}$ aryl, specifically phenyl or naphthyl. Herein, by optionally substituted, it refers to optionally substituted by one or more (for example, from 1 to 4, from 1 to 3, from 1 to 2 or 1) substituent selected from the group consisting of hydroxyl, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl.

According to this invention, in the formula (I-4), plural (i.e. a in total) group $Rp_3$ may be identical with or different from one another, each independently selected from the group consisting of a group represented by the formula

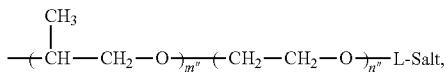

hydrogen, an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl and an optionally substituted $C_{6-50}$ aryl. As the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a $C_{2-20}$ linear or branched alkenyl or a $C_{8-20}$ linear or branched alkenyl, specifically octadecenyl, dodecenyl, linolyl, vinyl, propenyl or allyl, and so on. As the $C_{6-50}$ aryl, for example, there may be exemplified a $C_{6-20}$ aryl or a $C_{6-10}$ aryl, specifically phenyl or naphthyl. Herein, by optionally substituted, it refers to optionally substituted by one or more (for example, from 1 to 4, from 1 to 3, from 1 to 2 or 1) substituent selected from the group consisting of hydroxyl, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl.

According to this invention, in the formula (I-4), plural numerical value m' may be identical with or different from one another, each independently represents a value from 0 to 100, preferably a value from 0 to 50. Herein, the numerical value m' represents an average number of the unit

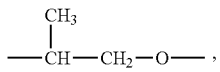

and thus could be a non-integer or an integer. As the numerical value m', for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-4), plural numerical value n' may be identical with or different from one another, each independently represents a value from 0 to 100, preferably a value from 0 to 50. Herein, the numerical value n' represents an average number of the unit $—CH_2—CH_2—O—$ and thus could be a non-integer or an integer. As the numerical value n', for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-4), plural numerical value m" may be identical with or different from one another, each independently represents a value from 0 to 100, preferably a value from 0 to 50. Herein, the numerical value m" represents an average number of the unit

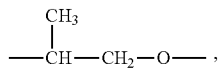

and thus could be a non-integer or an integer. As the numerical value m", for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-4), plural numerical value n" may be identical with or different from one another, each independently represents a value from 0 to 100, preferably a value from 0 to 50. Herein, the numerical value n" represents an average number of the unit $—CH_2—CH_2—O—$, and thus could be a non-integer or an integer. As the numerical value n", for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-4), plural numerical value m'" may be identical with or different from one another, each independently represents a value from 0 to 100, preferably a value from 0 to 50. Herein, the numerical value m'" represents an average number of the unit

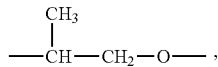

and thus could be a non-integer or an integer. As the numerical value m'", for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-4), plural numerical value n'" may be identical with or different from one another, each independently represents a value from 0 to 100, preferably a value from 0 to 50. Herein, the numerical value n'" represents an average number of the unit $—CH_2—CH_2—O—$, and thus could be a non-integer or an integer. As the numerical value n'", for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-4), it is preferred that the sum of all (i.e. corresponding to x"") numerical values m', all (i.e. corresponding to 1) numerical value m" and all (i.e. corresponding to a) numerical values m'" (i.e. throughout the molecular structure of the compound represented by the formula (I-4), the overall average number of the unit

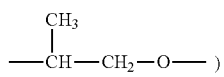

is greater than 0 but generally not greater than 100, preferably not greater than 50. In this context, throughout the molecular structure of the compound represented by the formula (I-4), it is preferable to contain (a certain amount of) the unit

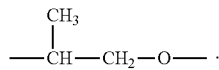

Herein, throughout the molecular structure of the compound represented by the formula (I-4), as the overall average number of the unit

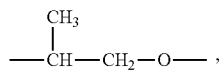

for example, there may be exemplified 0.1, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-4), it is preferred that the sum of all (i.e. corresponding to x'''') numerical values n', all (i.e. corresponding to 1) numerical values n'' and all (i.e. corresponding to a) numerical values n''' (i.e. throughout the molecular structure of the compound represented by the formula (I-4), the overall average number of the unit —$CH_2$—$CH_2$—O—) is not greater than 100, preferably not greater than 50. As the overall average number of the unit —$CH_2$—$CH_2$—O—, for example, there may be exemplified 0, 0.5, 1.2, 2.0, 2.5, 3.0, 3.5, 5.4, 7.5, 10.0, 15.0, 25.0, 30.2, 35.0, 40.0, 45.5 or 50.5, and so on.

According to an embodiment of this invention, preferably, in the formula (I-4), the sum of all (i.e. corresponding to x'''') numerical values n', all (i.e. corresponding to 1) numerical values n'' and all (i.e. corresponding to a) numerical values n''' (i.e. throughout the molecular structure of the compound represented by the formula (I-4), the overall average number of the unit —$CH_2$—$CH_2$—O—) is greater than 0. In this context, throughout the molecular structure of the compound represented by the formula (I-4), it is preferred to contain (a certain amount of) the unit —$CH_2$—$CH_2$—O—. Herein, throughout the molecular structure of the compound represented by the formula (I-4), as the overall average number of the unit —$CH_2$—$CH_2$—O—, for example, there may be exemplified 0.1, 0.5, 1.2, 2.0, 2.5, 3.0, 3.5, 5.4, 7.5, 10.0, 15.0, 25.0, 30.2, 35.0, 40.0, 45.5 or 50.5, and so on.

According to this invention, in the formula (I-4), the sum of all (i.e. corresponding to x''') numerical values n', all (i.e. corresponding to 1) numerical values n'' and all (i.e. corresponding to a) numerical values n''' (i.e. throughout the molecular structure of the compound represented by the formula (I-4), the overall average number of the unit —$CH_2$—$CH_2$—O—) plus the sum of all (i.e. corresponding to x'''')numerical values m', all (i.e. corresponding to 1) numerical value m'' and all (i.e. corresponding to a) numerical values m''' (i.e. throughout the molecular structure of the compound represented by the formula (I-4), the overall average number of the unit

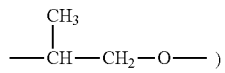

is greater than 0 but generally not greater than 200, preferably not greater than 100. In this context, throughout the molecular structure of the compound represented by the formula (I-4), it is preferable to contain (a certain amount of) the unit —$CH_2$—$CH_2$—O— and/or

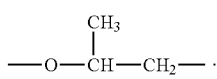

Herein, throughout the molecular structure of the compound represented by the formula (I-4), as the overall average number of these units, for example, there may be exemplified 0.1, 0.5, 1.5, 2.0, 3.0, 3.5, 7.5, 10.0, 15.0, 25.0, 30.2, 35.0, 40.0, 45.5, 50.5, 55.2, 60.0, 75.5, 80.5, 85.0, 90.5 or 95.7, and so on.

According to this invention, in the formula (I-4), plural group L may be identical with or different from one another, each independently selected from the group consisting of an optionally substituted $C_{1-10}$ linear or branched alkylene and an optionally substituted $C_{2-10}$ linear or branched alkenylene, preferably an optionally substituted $C_{1-5}$ linear or branched alkylene.

According to this invention, in the formula (I-4), plural group Salt may be identical with or different from one another, each independently represents a group represented by the formula -$A^-(M)_r^+$, wherein the group $A^-$ represents a carboxylate ion ($COO^-$) or a sulfonate ion ($SO_3^-$), the group M represents alkali metal (preferably Li, Na or K), alkaline earth metal (preferably Mg or Ca) or ammonium ($NH_4$). when the group M represents alkali metal or ammonium, r=1; when the group M represents alkaline earth metal, r=0.5.

According to an embodiment of this invention, in the formula (I-4), depending on the total number of the group Salt, the group $A^-$ could be one or more in number, wherein at least one out of the group $A^-$ represents the carboxylate ion ($COO^-$). In this context, throughout the molecular structure of the compound represented by the formula (I-4), it is preferable to exist at least one carboxylate ion ($COO^-$).

According to this invention, in the formula (I-4), it is required that at least one (for example, 1, 2 or 3) out of the groups Rc and Rh (covering all groups Rc and all groups Rh contained in the compound represented by the formula (I-4), obviously further comprising the group Rh in the aforesaid quaternary ammonium salt/hydroxide group) comprise in its molecular structure (one or more) $C_8$ linear moiety, whereby providing the compound represented by the formula (I-4) with anticipated surface active performances.

According to this invention, in the formula (I-1), the formula (I-2), the formula (I-3) and the formula (I-4), unless otherwise expressively specified, by optionally substituted, it refers to optionally substituted by one or more (for example, from 1 to 5, from 1 to 4, from 1 to 3, from 1 to 2 or 1) substituent selected from the group consisting of hydroxyl, a $C_{1-20}$ linear or branched alkyl, a $C_5$-10 monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_5$-10 monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_6$-10 aryl, specifically phenyl or naphthyl.

According to this invention, each of the aforesaid anionic-cationic-nonionic surfactants of this invention is as illustrated by the corresponding formula in each case, expressively indicating that in each molecular structure thereof, there necessarily exist the ionic groups $(M)_r^+$ and $X^-$ (sometimes expressed as (M)r and X respectively) at the same time. However, it is known that these two ionic groups are highly reactive to each other, and therefore, if both co-exist in the same system, for example, in the same molecular structure, tend to react with each other to generate an inorganic compound represented by the formula $(M)_r^+X^-$ (sometimes expressed as $(M)_rX$). The inorganic compound may sometimes present in free form independently (even for example, precipitating or isolating as a separate phase) from the anionic-cationic-nonionic surfactant of this invention, whereby at least a part (sometimes all) of these groups (i.e. The groups $(M)_r^+$ and $X^-$) will not constitute a part of the molecular structure of the anionic-cationic-nonionic surfactant of this invention any more as illustrated by these formulae. In this case, the anionic-cationic-nonionic surfactant of this invention actually (or at least a part thereof) takes the form of betaine (for example, by eliminating all/a part of the group $(M)_r^+$ or $X^-$). Herein, the groups $A^-$ and $N^+$ contained in the molecular structure of this anionic-cationic-nonionic surfactant will pair with each other as counterions. In this context, throughout the molecular structure of the anionic-cationic-nonionic surfactant of this invention, assuming that the total number of the group $X^-$ is e1, the total number of the group $N^+$ is e2, the total number of the group $A^-$ is e3, the total number of the group $(M)_r^+$ is e4, if e2=e3, then $0 \le e1 \le e2$, $0 \le e4 \le e3$; or, if e2>e3, then $0<e1 \le e2$, $0 \le e4 \le e3$; or, if e2<e3, then $0 \le e1 \le e2$, $0<e4 \le e3$, with the proviso that e1+e3=e2+e4. Or, it is preferable that e2=e3, e1=0, e4=0. For this reason, depending on to what extent the inorganic compound is generated, especially the ratio by number of the group $(M)_r^+$ to the group $X^-$ throughout the molecular structure of the anionic-cationic-nonionic surfactant of this invention, or if there exist reaction conditions favorable for generation of the inorganic compound, the anionic-cationic-nonionic surfactant of this invention in its molecular structure may sometimes not contain the group $(M)_r^+$ and the group $X^-$ at the same time, and sometimes even not contain any of the group $(M)_r^+$ and the group X. Generation or no generation of the inorganic compound, to what extent it is generated, or in what form this inorganic compound takes, will not substantially or significantly change the performances of the anionic-cationic-nonionic surfactant of this invention (for example, the interfacial activity and the stability thereof), therefore this specification does not intend to specify this inorganic compound in any way. In view of this, in the context of this specification, for a more accurate description or definition of the anionic-cationic-nonionic surfactant of this invention, an expression "as substantially represented by the formula" or the like is introduced. Herein, by "as substantially represented by the formula" (for example, as substantially represented by the formula (I), as substantially represented by the formula (I-1), as substantially represented by the formula (I-2), as substantially represented by the formula (I-3) or as substantially represented by the formula (I-4) as aforesaid) or the like, means that the anionic-cationic-nonionic surfactant of this invention may, as expressively illustrated by the formula, contain both the group $(M)_r^+$ and the group $X^-$, or as hereinbefore explained, be deprived of at least a part (even all) of the group $(M)_r^+$ and/or the group $X^-$, even contain no the group $(M)_r^+$ and/or the group $X^-$. To a person skilled in the art, all these forms represent different embodiments of the anionic-cationic-nonionic surfactant of this invention, and are necessarily covered by the present invention.

According to this invention, the aforesaid anionic-cationic-nonionic surfactants could be produced for example in line with a process comprising the following Step (1) to Step (5).

Step (1): reacting one or more multifunctional compound containing nitrogen and carrying one or more functional group selected from the group consisting of —OH, —$NH_2$ and —NH— with one or more alkylene oxide represented by the following formula (Y) in the presence of an alkaline catalyst, to obtain an ether product.

According to this invention, in Step (1), as the multifunctional compound, any compound carrying one or more (for example, from 1 to 10, preferably from 1 to 4, for example, 2, 3 or 4) functional group selected from the group consisting of —OH, —$NH_2$ and —NH— could be used, without any specific limitation thereto. The functional group has an active hydrogen, which is capable of initiating the ring open (polymerization) reaction of an alkylene oxide like ethylene oxide, whereby introducing a (poly)ether segment into the molecular structure of the multifunctional compound. As the multifunctional compound, one kind or a mixture of two or more kinds at any ratio therebetween could be used. Further, the multifunctional compound may be commercially available, or could be produced in a conventional manner.

According to this invention, in Step (1), the multifunctional compound necessarily comprises a nitrogen atom. The nitrogen atom may originate from a primary amine group, a tertiary amine group or a secondary amine group contained in the multifunctional compound.

According to this invention, in Step (1), as the multifunctional compound, there is specifically exemplified a compound represented by the following formula (X). As the compound represented by the formula (X), one kind or a mixture of two or more kinds at any ratio therebetween could be used.

(X)

According to this invention, in the formula (X), the group $R'_1$ to $R'_3$ may be identical with or different from one another, each independently selected from the group consisting of hydrogen, an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl, an optionally substituted $C_{6-50}$ aryl and a group represented by the formula -$L_A$-(Func)$_{x0}$. Herein, by optionally substituted, it refers to optionally substituted by one or more (for example, from 1 to 4, from 1 to 3, from 1 to 2 or 1) substituent selected from the group consisting of oxo (i.e. ).

hydroxyl, a group represented by the formula -L$_A$-(Func)$_{x0}$, a C$_{1-20}$ linear or branched alkyl, a C$_{5-10}$ monocyclic or polycyclic cycloalkyl, a C$_{2-20}$ linear or branched alkenyl and a C$_{6-20}$ aryl. As the C$_{1-20}$ linear or branched alkyl, for example, there may be exemplified a C$_{1-10}$ linear or branched alkyl or a C$_{1-6}$ linear or branched alkyl, or methyl or ethyl, and so on. As the C$_{5-10}$ monocyclic or polycyclic cycloalkyl, for example, there may be exemplified a C$_{5-8}$ monocyclic or polycyclic cycloalkyl or a C$_{5-7}$ monocyclic or polycyclic cycloalkyl, especially a C$_{5-7}$ monocyclic cycloalkyl, specifically cyclopentyl or cyclohexyl. As the C$_{2-20}$ linear or branched alkenyl, for example, there may be exemplified a C$_{2-10}$ linear or branched alkenyl, specifically vinyl, propenyl or allyl, and so on. As the C$_{6-20}$ aryl, for example, there may be exemplified a C$_{6-10}$ aryl, specifically phenyl or naphthyl.

According to this invention, in the formula (X), it is required that at least one (for example, two at most) out of the groups R'$_1$ to R'$_3$ represents hydrogen or a group represented by the formula -L$_A$-(Func)$_{x0}$.

According to this invention, in the formula (X), in each definition of the groups R'$_1$ to R'$_3$, as the C$_{1-50}$ linear or branched alkyl, for example, there may be exemplified a C$_{1-20}$ linear or branched alkyl or a C$_{8-20}$ linear or branched alkyl, specifically octadecyl, lauryl, octyl, hexadecyl, hexyl, methyl or ethyl, and so on. As the C$_{5-50}$ monocyclic or polycyclic cycloalkyl, for example, there may be exemplified a C$_{5-10}$ monocyclic or polycyclic cycloalkyl, a C$_{5-8}$ monocyclic or polycyclic cycloalkyl or a C$_{5-7}$ monocyclic or polycyclic cycloalkyl, especially a C$_{5-7}$ monocyclic cycloalkyl, specifically cyclopentyl or cyclohexyl. As the C$_{2-50}$ linear or branched alkenyl, for example, there may be exemplified a C$_{2-20}$ linear or branched alkenyl or a C$_{8-20}$ linear or branched alkenyl, specifically octadecenyl, dodecenyl, linolyl, vinyl, propenyl or allyl, and so on. As the C$_{6-50}$ aryl, for example, there may be exemplified a C$_{6-20}$ aryl or a C$_{6-10}$ aryl, specifically phenyl or naphthyl.

According to this invention, in the formula (X), in the group represented by the formula -L$_A$-(Func)$_{x0}$, the group L$_A$ represents an optionally substituted x0+1 valent C$_{1-50}$ linear or branched alkyl, an optionally substituted x0+1 valent C$_{5-50}$ monocyclic or polycyclic cycloalkyl, an optionally substituted x0+1 valent C$_{2-50}$ linear or branched alkenyl, an optionally substituted x0+1 valent C$_{6-50}$ aryl or an optionally substituted x0+1 valent C$_{3-50}$ linear or branched heteroalkyl. As the optionally substituted x0+1 valent C$_{1-50}$ linear or branched alkyl, it is preferably an optionally substituted x0+1 valent C$_{1-20}$ linear or branched alkyl. As the optionally substituted x0+1 valent C$_{5-50}$ monocyclic or polycyclic cycloalkyl, for example, there may be exemplified an optionally substituted x0+1 valent C$_{5-10}$ monocyclic or polycyclic cycloalkyl, an optionally substituted x0+1 valent C$_{5-8}$ monocyclic or polycyclic cycloalkyl or an optionally substituted x0+1 valent C$_{5-7}$ monocyclic or polycyclic cycloalkyl, especially an optionally substituted x0+1 valent C$_{5-7}$ monocyclic cycloalkyl, for example, cyclohexyl. The optionally substituted x0+1 valent C$_{2-50}$ linear or branched alkenyl is preferably an optionally substituted x0+1 valent C$_{2-20}$ linear or branched alkenyl. The optionally substituted x0+1 valent C$_{6-50}$ aryl is preferably an optionally substituted x0+1 valent C$_{6-20}$ aryl, for example, phenyl or naphthyl. The optionally substituted x0+1 valent C$_{3-50}$ linear or branched heteroalkyl is preferably an optionally substituted x0+1 valent C$_{3-20}$ linear or branched heteroalkyl.

According to this invention, in the formula (X), plural group Func may be identical with or different from one another, each independently selected from the group consisting of —OH, —NH— and —NH$_2$, preferably each independently selected from the group consisting of —OH and —NH$_2$.

According to this invention, in the formula (X), the numerical value x0+1 (x0 plus 1) generally represents the valence of the group L$_A$, wherein the numerical value x0 is an integer from 1 to 10, preferably an integer from 1 to 4, for example, 1, 2 or 3. However, it is reasonable to a person skilled in the art that when the group Func represents —NH—, the group L$_A$ is to be interrupted by this —NH— at any (acceptable) position. Herein, the numerical value x0 (or at least a part thereof, depending on the total number of —NH—) represents how many times this interruption occurs (hereinafter referred to as interruption number), and accordingly, does not necessarily represent the valence of the group L$_A$ any more. In this context, the valence of the group L$_A$ could be as low as 1, for example, in the case that all (i.e. x0 in total) of the group Func represent —NH—. When plural —NH— exist, the group L$_A$ is to be interrupted by these groups —NH— respectively at any (acceptable) position for a corresponding number of times. By interruption, it means that the group —NH— enters inside the molecular structure of the group L$_A$ rather than locates at a terminal of the main chain or any side chain in the molecular structure thereof. It is preferred that any two or more of these groups —NH— do not directly bond to one another. Specifically, assuming that the group Func is —NH—, x0 is 1 (with an interruption number of 1), while the group L$_A$ represents a 1 valent (not 2 valent any more) C$_8$ linear alkyl

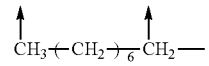

(the terminals of the main chain in the molecular structure being indicated by the arrow marks in the formula), the group L$_A$ could be

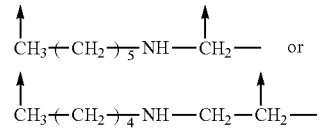

or the like.

According to this invention, in the formula (X), unless otherwise specified, by optionally substituted, it refers to optionally substituted by one or more (for example, from 1 to 5, from 1 to 4, from 1 to 3, from 1 to 2 or 1) substituent selected from the group consisting of oxo, hydroxyl, a C$_{1-20}$ linear or branched alkyl, a C$_{5-10}$ monocyclic or polycyclic cycloalkyl, a C$_{2-20}$ linear or branched alkenyl and a C$_{6-20}$ aryl. As the C$_{1-20}$ linear or branched alkyl, for example, there may be exemplified a C$_{1-10}$ linear or branched alkyl or a C$_{1-6}$ linear or branched alkyl, or methyl or ethyl, and so on. As the C$_{5-10}$ monocyclic or polycyclic cycloalkyl, for example, there may be exemplified a C$_{5-8}$ monocyclic or polycyclic cycloalkyl or a C$_{5-7}$ monocyclic or polycyclic cycloalkyl, especially a C$_{5-7}$ monocyclic cycloalkyl, specifically cyclopentyl or cyclohexyl. As the C$_{2-20}$ linear or branched alkenyl, for example, there may be exemplified a C$_{2-10}$ linear or branched alkenyl, specifically vinyl, propenyl or allyl, and so on. As the C$_{6-20}$ aryl, for example, there may be exemplified a C$_{6-10}$ aryl, specifically phenyl or naphthyl.

According to an embodiment of this invention (referred to as Embodiment A), in the formula (X), when oxo exists as the substituent on a group (for example, the group $L_A$), it is preferred that at least one oxo exists on the carbon atom directly bonding to a N atom (if any, for example, a N atom possibly originated from a linear or branched heteroalkyl), so as to make the carbon atom to present in the form of carbonyl (i.e.

(i.e. 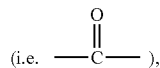 ), whereby introducing a moiety (for example, imido) of carbonyl directly bonding to a N atom into the group. Further, to provide better hydrolysis resistance or chemical resistance, it is preferred that there is no oxo as the substituent on at least a part (preferably all) of the carbon atoms directly bonding to an O or S atom (if any), and/or, on at least a part of (preferably all) of terminal carbon atoms (i.e. The carbon atom at a free end and/or a un-bonded position of the molecular chain) (excluding any terminal carbon atom directly bonding to the group Func in the group say the group $L_A$ when the group Func represents —NH— or —NH$_2$, see the Embodiment B hereinafter), and/or, two carbon atoms directly bonding to each other are not substituted by oxo simultaneously. By doing so, no chemically active or unstable group like an ester or aldehyde group or the like will be introduced into the group. Specifically, assuming that the group $L_A$ represents a 2 valent linear alkyl

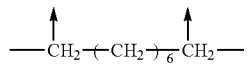

(comprising two terminal carbon atoms as indicated by the arrow marks in the formula) substituted by one oxo, according to these rules, this group may be preferably

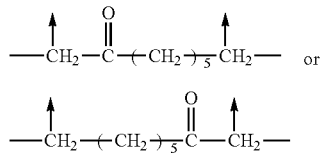

or the like. Or, assuming that the group $L_A$ represents a 2 valent branched heteroalkyl

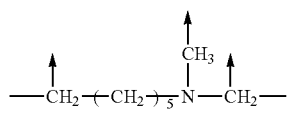

(comprising three terminal carbon atoms as indicated by the arrow marks in the formula, also comprising three carbon atoms directly bonding to a N atom) substituted by one oxo, according to these rules, this group may be preferably

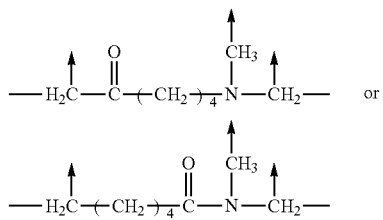

or the like.

According to an embodiment of this invention (referred to as Embodiment B), when the group Func represents —NH— or —NH$_2$, in the formula (X), when oxo exists as the substituent, it is preferred that at least one oxo is positioned at the carbon atom directly bonding to the group Func, or in other words, at least one out of all carbon atoms directly bonding to the group Func has oxo thereon as the substituent, whereby introducing into the group $L_A$ a moiety (for example, amido) formed by directly bonding carbonyl to a N atom. Specifically, assuming that the group $L_A$ represents a 2 valent linear alkyl

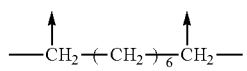

substituted by one oxo, the group Func represents —NH$_2$, then the group represented by the formula -$L_A$-(Func)$_{x0}$, in addition to the

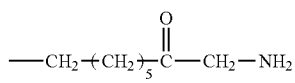

preferred by Embodiment A, could be further

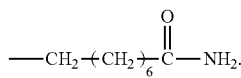

According to this invention, it is required that at least one out of the multifunctional compound and the hereinafter described quaternizing agent (represented by the formula (A)) comprises necessarily in its molecular structure a (one or more) $C_8$ linear moiety (hereinafter sometimes referred to as Requirement (1)). In this context, according to Requirement (1), it is further required that at least one out of the amine compound represented by the formula (X) and the quaternizing agent represented by the formula (A) comprises necessarily in its molecular structure a (one or more) $C_8$ linear moiety. Specifically, according to Requirement (1), at least one (for example, 1, 2 or 3) out of the groups R'$_1$, R'$_2$, R'$_3$ (originated from the amine compound represented by the formula (X)) and the group Rh (as hereinafter described, originated from the quaternizing agent) comprises necessarily in its molecular structure a (one or more) $C_8$ linear moiety.

According to this invention, in Step (1), as the amine compound represented by the formula (X), there may be specifically exemplified a compound represented by the following formula (X-1), a compound represented by the following formula (X-2), a compound represented by the following formula (X-3) and a compound represented by the following formula (X-4). As the compound, one kind or a mixture of two or more kinds at any ratio therebetween could be used.

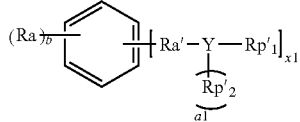

(X-1)

According to this invention, in the formula (X-1), plural group Ra may be identical with or different from one another, each independently selected from the group consisting of hydrogen, an optionally substituted $C_{1-20}$ linear or branched alkyl, an optionally substituted $C_{2-20}$ linear or branched alkenyl and an optionally substituted $C_{6-10}$ aryl, preferably an optionally substituted $C_{8-20}$ linear or branched alkyl and an optionally substituted $C_{6-10}$ aryl.

According to this invention, in the formula (X-1), plural group Ra' may be identical with or different from one another, each independently selected from the group consisting of a single bond, an optionally substituted $C_{1-10}$ linear or branched alkylene, an optionally substituted $C_{2-10}$ linear or branched alkenylene, carbonyl, an optionally substituted $C_{1-10}$ linear or branched alkylene carbonyl and an optionally substituted $C_{2-10}$ linear or branched alkenylene carbonyl, preferably each independently selected from the group consisting of a single bond and an optionally substituted $C_{1-6}$ linear or branched alkylene.

According to this invention, in the formula (X-1), the numerical value b represents an integer from 1 to 3, preferably 1.

According to this invention, in the formula (X-1), the numerical value x1 represents the number of the group

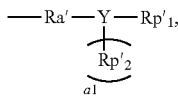

which is an integer from 1 to 5, preferably an integer from 1 to 4, for example, 1, 2 or 3. Obviously, b+x1≤6.

According to this invention, in the formula (X-1), plural group Y may be identical with or different from one another, each independently selected from the group consisting of N and O, with the proviso that when the group Y represents N, a1=1, when the group Y represents O, a1=0. Further, at least one group Y represents N.

According to this invention, in the formula (X-1), plural (x1 in total) group Rp'1 may be identical with or different from one another, each independently selected from the group consisting of hydrogen, an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl and an optionally substituted $C_{6-50}$ aryl, with the proviso that at least one group Rp'1 represents hydrogen. As the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a $C_{2-20}$ linear or branched alkenyl or a $C_{8-20}$ linear or branched alkenyl, specifically octadecenyl, dodecenyl, linolyl, vinyl, propenyl or allyl, and so on. As the $C_{6-50}$ aryl, for example, there may be exemplified a $C_{6-20}$ aryl or a $C_{6-10}$ aryl, specifically phenyl or naphthyl. Herein, by optionally substituted, it refers to optionally substituted by one or more (for example, from 1 to 4, from 1 to 3, from 1 to 2 or 1) substituent selected from the group consisting of hydroxyl, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl.

According to this invention, in the formula (X-1), plural (i.e. x1×a1 in total) group Rp'2 may be identical with or different from one another, each independently selected from the group consisting of hydrogen, an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl and an optionally substituted $C_{6-50}$ aryl. As the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a $C_{2-20}$ linear or branched alkenyl or a $C_{8-20}$ linear or branched alkenyl, specifically octadecenyl, dodecenyl, linolyl, vinyl, propenyl or allyl, and so on. As the $C_{6-50}$ aryl, for example, there may be exemplified a $C_{6-20}$ aryl or a $C_{6-10}$ aryl, specifically phenyl or naphthyl. Herein, by optionally substituted, it refers to optionally substituted by one or more (for example, from 1 to 4, from 1 to 3, from 1 to 2 or 1) substituent selected from the group consisting of hydroxyl, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl.

According to this invention, in the formula (X-1), according to the aforesaid Requirement (1), it is required that at least one (for example, 1, 2 or 3) out of the groups Ra and Rh (covering all groups Ra contained in the compound represented by the formula (X-1) and all groups Rh contained in the hereinafter described quaternizing agent represented by the formula (A)) comprise necessarily in its molecular structure one or more of the $C_8$ linear moiety.

(X-2)

According to this invention, in the formula (X-2), the group Rb represents an optionally substituted $C_{1-49}$ linear or branched alkyl, an optionally substituted $C_{5-49}$ monocyclic or polycyclic cycloalkyl or an optionally substituted $C_{2-49}$ linear or branched alkenyl, preferably an optionally substituted $C_{1-29}$ linear or branched alkyl, an optionally substituted $C_{5-10}$ monocyclic or polycyclic cycloalkyl or an optionally substituted $C_{2-29}$ linear or branched alkenyl, or represents an optionally substituted $C_{8-29}$ linear or branched alkyl, an optionally substituted $C_{5-8}$ monocyclic or polycyclic cycloalkyl or an optionally substituted $C_{8-29}$ linear or branched alkenyl, or represents an optionally substituted $C_{8-19}$ linear or branched alkyl, an optionally substituted $C_{5-7}$ monocyclic cycloalkyl (for example, cyclohexyl) or an optionally substituted $C_{8-19}$ linear or branched alkenyl.

According to this invention, in the formula (X-2), plural group Rb' may be identical with or different from one another, each independently selected from the group consisting of a single bond and carbonyl.

According to this invention, in the formula (X-2), plural group Y may be identical with or different from one another, each independently selected from the group consisting of N and O, with the proviso that when the group Y represents N, a2=1, when the group Y represents O, a2=0. Further, at least one group Y represents N.

According to this invention, in the formula (X-2), the numerical value x2 represents the number of the group

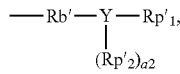

which is an integer from 1 to 10, preferably an integer from 1 to 4, for example, 1, 2 or 3.

According to this invention, in the formula (X-2), plural (i.e. x2 in total) group Rp'$_1$ may be identical with or different from one another, each independently selected from the group consisting of hydrogen, an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl and an optionally substituted $C_{6-50}$ aryl, with the proviso that at least one group Rp'$_1$ represents hydrogen. As the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a $C_{2-20}$ linear or branched alkenyl or a $C_{8-20}$ linear or branched alkenyl, specifically octadecenyl, dodecenyl, linolyl, vinyl, propenyl or allyl, and so on. As the $C_{6-50}$ aryl, for example, there may be exemplified a $C_{6-20}$ aryl or a $C_{6-10}$ aryl, specifically phenyl or naphthyl. Herein, by optionally substituted, it refers to optionally substituted by one or more (for example, from 1 to 4, from 1 to 3, from 1 to 2 or 1) substituent selected from the group consisting of hydroxyl, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl.

According to this invention, in the formula (X-2), plural (i.e. x2×a2 in total) group Rp'$_2$ may be identical with or different from one another, each independently selected from the group consisting of hydrogen, an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl and an optionally substituted $C_{6-50}$ aryl. As the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a $C_{2-20}$ linear or branched alkenyl or a $C_{8-20}$ linear or branched alkenyl, specifically octadecenyl, dodecenyl, linolyl, vinyl, propenyl or allyl, and so on. As the $C_{6-50}$ aryl, for example, there may be exemplified a $C_{6-20}$ aryl or a $C_{6-10}$ aryl, specifically phenyl or naphthyl. Herein, by optionally substituted, it refers to optionally substituted by one or more (for example, from 1 to 4, from 1 to 3, from 1 to 2 or 1) substituent selected from the group consisting of hydroxyl, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl.

According to this invention, in the formula (X-2), according to the aforesaid Requirement (1), it is required that at least one (for example, 1, 2 or 3) out of the groups Rb and Rh (covering all groups Rb contained in the compound represented by the formula (X-2) and all groups Rh contained in the hereinafter described quaternizing agent represented by the formula (A)) comprise necessarily in its molecular structure one or more of the $C_8$ linear moiety.

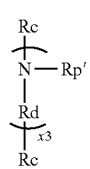

(X-3)

According to this invention, in the formula (X-3), plural group Rc may be identical with or different from one another, each independently selected from the group consisting of an optionally substituted $C_{1-20}$ linear or branched alkyl, an optionally substituted $C_{2-20}$ linear or branched alkenyl, an optionally substituted $C_{1-20}$ linear or branched alkyl carbonyl and an optionally substituted $C_{2-20}$ linear or branched alkenyl carbonyl, or each independently selected from the group consisting of an optionally substituted $C_{1-10}$ linear or branched alkyl, an optionally substituted $C_{2-10}$ linear or branched alkenyl, an optionally substituted $C_{1-10}$ linear or branched alkyl carbonyl and an optionally substituted $C_{2-10}$ linear or branched alkenyl carbonyl, or each independently selected from the group consisting of an optionally substituted $C_{5-20}$ linear or branched alkyl, an optionally substituted $C_{5-20}$ linear or branched alkenyl, an optionally substituted $C_{5-20}$ linear or branched alkyl carbonyl and an optionally substituted $C_{5-20}$ linear or branched alkenyl carbonyl.

According to this invention, in the formula (X-3), plural group Rd may be identical with or different from one another, each independently selected from the group consisting of an optionally substituted $C_{1-10}$ linear or branched alkylene, an optionally substituted $C_{2-10}$ linear or branched alkenylene, an optionally substituted $C_{1-10}$ linear or branched alkylene carbonyl, an optionally substituted $C_{2-10}$ linear or branched alkenylene carbonyl, an optionally substituted carbonyl $C_{1-10}$ linear or branched alkylene carbonyl and an optionally substituted carbonyl $C_{2-10}$ linear or branched alkenylene carbonyl, preferably each independently selected from the group consisting of an optionally substituted $C_{1-5}$ linear or branched alkylene and an optionally substituted $C_{1-5}$ linear or branched alkylene carbonyl.

According to this invention, in the formula (X-3), the numerical value x3 represents the number of the unit

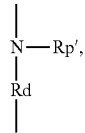

which is an integer from 1 to 10, preferably an integer from 1 to 4, for example, 1, 2 or 3.

According to this invention, in the formula (X-3), plural (i.e. x3 in total) group Rp' may be identical with or different from one another, each independently selected from the group consisting of hydrogen, an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl and an optionally substituted $C_{6-50}$ aryl, with the proviso that at least one group Rp' represents hydrogen. As the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a $C_{2-20}$ linear or branched alkenyl or a $C_{8-20}$ linear or branched alkenyl, specifically octadecenyl, dodecenyl, linolyl, vinyl, propenyl or allyl, and so on. As the $C_{6-50}$ aryl, for example, there may be exemplified a $C_{6-20}$ aryl or a $C_{6-10}$ aryl, specifically phenyl or naphthyl. Herein, by optionally substituted, it refers to optionally substituted by one or more (for example, from 1 to 4, from 1 to 3, from 1 to 2 or 1) substituent selected from the group consisting of hydroxyl, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl.

According to this invention, in the formula (X-3), according to the aforesaid Requirement (1), it is required that at least one (for example, 1, 2 or 3) out of the groups Rc and Rh (covering all groups Rc contained in the compound represented by the formula (X-3) and all groups Rh contained in the hereinafter described quaternizing agent represented by the formula (A)) comprise necessarily in its molecular structure one or more of the $C_8$ linear moiety.

(X-4)

According to this invention, in the formula (X-4), the group Rc represents an optionally substituted $C_{1-20}$ linear or branched alkyl, an optionally substituted $C_{2-20}$ linear or branched alkenyl, an optionally substituted $C_{1-20}$ linear or branched alkyl carbonyl or an optionally substituted $C_{2-20}$ linear or branched alkenyl carbonyl, or each independently represents an optionally substituted $C_{1-10}$ linear or branched alkyl, an optionally substituted $C_{2-10}$ linear or branched alkenyl, an optionally substituted $C_{1-10}$ linear or branched alkyl carbonyl or an optionally substituted $C_{2-10}$ linear or branched alkenyl carbonyl, or each independently represents an optionally substituted $C_{5-20}$ linear or branched alkyl, an optionally substituted $C_{5-20}$ linear or branched alkenyl, an optionally substituted $C_{5-20}$ linear or branched alkyl carbonyl or an optionally substituted $C_{5-20}$ linear or branched alkenyl carbonyl.

According to this invention, in the formula (X-4), plural group Rd may be identical with or different from one another, each independently selected from the group consisting of an optionally substituted $C_{1-10}$ linear or branched alkylene, an optionally substituted $C_{2-10}$ linear or branched alkenylene, an optionally substituted $C_{1-10}$ linear or branched alkylene carbonyl, an optionally substituted $C_{2-10}$ linear or branched alkenylene carbonyl, an optionally substituted carbonyl $C_{1-10}$ linear or branched alkylene carbonyl and an optionally substituted carbonyl $C_{2-10}$ linear or branched alkenylene carbonyl, preferably each independently selected from the group consisting of an optionally substituted $C_{1-5}$ linear or branched alkylene and an optionally substituted $C_{1-5}$ linear or branched alkylene carbonyl.

According to this invention, in the formula (X-4), the group Y represents N or O, with the proviso that when the group Y represents N, a4=1, when the group Y represents O, a4=0.

According to this invention, in the formula (X-4), the numerical value x4 represents the number of the unit

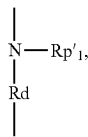

which is an integer from 1 to 9, preferably an integer from 1 to 3, more preferably 1 or 2.

According to this invention, in the formula (X-4), plural (i.e. x4 in total) group $Rp'_1$ may be identical with or different from one another, each independently selected from the group consisting of hydrogen, an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl and an optionally substituted $C_{6-50}$ aryl, with the proviso that at least one group $Rp'_1$ represents hydrogen. As the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a $C_{2-20}$ linear or branched alkenyl or a $C_{8-20}$ linear or branched alkenyl, specifically octadecenyl, dodecenyl, linolyl, vinyl, propenyl or allyl, and so on. As the $C_{6-50}$ aryl, for example, there may be exemplified a $C_{6-20}$ aryl or a $C_{6}$-10 aryl, specifically phenyl or naphthyl. Herein, by optionally substituted, it refers to optionally substituted by one or more (for example, from 1 to 4, from 1 to 3, from 1 to 2 or 1) substituent selected from the group consisting of hydroxyl, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl.

According to this invention, in the formula (X-4), the group $Rp'_2$ may be selected from the group consisting of hydrogen, an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl and an optionally substituted $C_{6-50}$ aryl. As the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a $C_{2-20}$ linear or branched alkenyl or a $C_{8-20}$ linear or branched alkenyl, specifically octadecenyl, dodecenyl, linolyl, vinyl, propenyl or allyl, and so on. As the $C_{6-50}$ aryl, for example, there may be exemplified a $C_{6-20}$ aryl or a $C_{6-10}$ aryl, specifically phenyl or naphthyl. Herein, by optionally substituted, it refers to optionally substituted by one or more (for example, from 1 to 4, from 1 to 3, from 1 to 2 or 1) substituent selected from the group consisting of hydroxyl, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl.

According to this invention, in the formula (X-4), plural (i.e. a4 in total) group $Rp'_3$ may be identical with or different from one another, each independently selected from the group consisting of hydrogen, an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl and an optionally substituted $C_{6-50}$ aryl. As the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a $C_{2-20}$ linear or branched alkenyl or a $C_{8-20}$ linear or branched alkenyl, specifically octadecenyl, dodecenyl, linolyl, vinyl, propenyl or allyl, and so on. As the $C_{6-50}$ aryl, for example, there may be exemplified a $C_{6-20}$ aryl or a $C_6$-10 aryl, specifically phenyl or naphthyl. Herein, by optionally substituted, it refers to optionally substituted by one or more (for example, from 1 to 4, from 1 to 3, from 1 to 2 or 1) substituent selected from the group consisting of hydroxyl, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_6$-10 aryl, specifically phenyl or naphthyl.

According to this invention, in the formula (X-4), according to the aforesaid Requirement (1), it is required that at least one (for example, 1, 2 or 3) out of the groups Rc and Rh (covering all groups Rc contained in the compound represented by the formula (X-4) and all groups Rh contained in the hereinafter described quaternizing agent represented by the formula (A)) comprise necessarily in its molecular structure one or more of the $C_8$ linear moiety.

According to this invention, in the formulae (X-1), (X-2), (X-3) and (X-4), unless otherwise specified, by optionally substituted, it refers to optionally substituted by one or more (for example, from 1 to 5, from 1 to 4, from 1 to 3, from 1 to 2 or 1) substituent selected from the group consisting of oxo, hydroxyl, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_6$-10 aryl, specifically phenyl or naphthyl.

According to this invention, the aforesaid multifunctional compound, the amine compound represented by the formula (X), the compound represented by the formula (X-1), the compound represented by the formula (X-2), the compound represented by the formula (X-3) or the compound represented by the formula (X-4), could be commercially available or produced in any conventional manner. For example, the compound represented by the formula (X-2) (wherein, Y=N, Rb' is carbonyl, the group Rp'$_1$ and the group Rp'$_2$ are hydrogen), i.e.

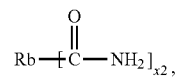

could be produced by reacting a compound represented by the following formula (X-2-1) with an amidating agent (for example, diisopropanol amine) in the presence of an alkaline catalyst (referred to as amidating step).

wherein, the group Rb and the numerical value x2 are as defined in the formula (X-2), the group $R_{ac}$ is H or a $C_{1-4}$ linear or branched alkyl.

According to this invention, the amidating step could be conducted in any conventional manner, wherein the reaction temperature could be generally 100-200 degrees Celsius, the reaction duration could be generally 1-10 h, the reaction pressure could be the normal pressure or any pressure suitable for this reaction.

According to this invention, in the amidating step, as the alkaline catalyst, any alkaline catalyst conventionally used in this field for a similar purpose may be used as such, wherein preference is given to alkali metal hydroxide, especially NaOH or KOH. As the alkaline catalyst, one kind or a mixture of two or more kinds at any ratio therebetween could be used. As the amount of the alkaline catalyst to be used, any amount conventionally used in this field may be mentioned, but could be generally determined such that the alkaline catalyst accounts for 0.2-20 wt %, preferably 0.5-15 wt % of the total weight of the compound represented by the formula (X-2-1) and the amidating agent.

According to this invention, in the amidating step, the ratio by molar of the compound represented by the formula (X-2-1) to the amidating agent could be generally 1:1-15, 1:1-10, 1:1-8, 1:1-5 or 1:2-4, but not limiting thereto, which could be any ratio by molar sufficient to convert all (i.e. x2 in total) of the group —$COOR_{ac}$ into its corresponding amido.

According to this invention, upon completion of the amidating step, by any known separation method (for example, vacuum suction), any unreacted amidating agent is removed from the reaction product mixture, so as to obtain a compound represented by the formula (X-2) (wherein, Y=N, Rb' is carbonyl, the group Rp'$_1$ and the group Rp'$_2$ are hydrogen), without needing any further purification or separation.

According to this invention, in the formula (Y), the group Ru' represents a $C_{2-6}$ linear or branched alkylene, wherein preference is given to —$CH_2$—$CH_2$— and/or —$CH_2$—CH($CH_3$)—, more preferably a combination of —$CH_2$—$CH_2$— and —$CH_2$—CH($CH_3$)—.

According to this invention, in Step (1), as the alkylene oxide represented by the formula (Y), for example, there may be exemplified ethylene oxide, propylene oxide, butylene oxide, hexene oxide, and so on. As these alkylene oxides, one kind or a mixture of two or more kinds at any ratio therebetween could be used, for example, a combination of propylene oxide and ethylene oxide.

According to this invention, one or more of the alkylene oxide represented by the formula (Y) is used, preferably, the alkylene oxide comprises at least propylene oxide. Propylene oxide could if needed be used in combination with any other alkylene oxide represented by the formula (Y) (especially ethylene oxide). In this combination, the ratio by molar of propylene oxide to said other alkylene oxide represented by the formula (Y) (especially ethylene oxide), for example, could be 1:0.1-10, but not limiting thereto.

According to this invention, in Step (1), as the alkaline catalyst, any alkaline catalyst conventionally used in this field for a similar purpose may be used as such, wherein preference is given to alkali metal hydroxide, especially KOH. As the alkaline catalyst, one kind or a mixture of two or more kinds at any ratio therebetween could be used.

According to this invention, in Step (1), as the amount of the alkaline catalyst to be used, any amount conventionally used in this field may be mentioned, but could be generally determined such that the ratio by molar of the multifunctional compound (e.g. The amine compound represented by the formula (X)) to the alkaline catalyst is 1:1-10, preferably 1:1-5.

According to this invention, in Step (1), the ratio by molar of the multifunctional compound (e.g. The amine compound represented by the formula (X)) to the alkylene oxide could be generally 1:0-200, preferably 1:0-100, excluding 0, more preferably 1:0.1-50.

According to this invention, in Step (1), the reaction temperature could be generally from the room temperature to 300 degrees Celsius, preferably 100-200 degrees Celsius, the reaction duration could be generally 1-20 h, preferably from 1 to 10 h, while the reaction pressure could be any pressure suitable for this reaction, for example, the normal pressure.

According to a preferred embodiment of this invention, in Step (1), as the alkylene oxide represented by the formula (Y), if two or more thereof are used in combination (preferably comprising at least propylene oxide), the multifunctional compound (for example, the amine compound represented by the formula (X)) is made to firstly react with (at least a partial amount of or a whole amount of) propylene oxide, then (preferably at least after partial or total completion of the reaction with propylene oxide) with any other alkylene oxide (for example, ethylene oxide).

According to this invention, upon completion of Step (1), the thus obtained reaction product mixture could be used as such as the ether product for the succeeding Step (2), without any separation or purification thereto, or after merely separating therefrom (for example, by washing with water) the alkaline catalyst.

Step (2): reacting the ether product and a quaternizing agent represented by the following formula (A), whereby obtaining a cationic-nonionic surfactant.

Rh—X'  (A)

According to this invention, in the formula (A), the group Rh represents an optionally substituted $C_{1-50}$ linear or branched alkyl, an optionally substituted $C_{5-50}$ monocyclic or polycyclic cycloalkyl, an optionally substituted $C_{2-50}$ linear or branched alkenyl or an optionally substituted $C_{6-50}$ aryl. As the $C_{1-50}$ linear or branched alkyl, for example, there may be exemplified a $C_{1-20}$ linear or branched alkyl or a $C_{8-20}$ linear or branched alkyl, specifically octadecyl, lauryl, octyl, hexadecyl, hexyl, methyl or ethyl, and so on. As the $C_{5-50}$ monocyclic or polycyclic cycloalkyl, for example, there may be exemplified a $C_{5-10}$ monocyclic or polycyclic cycloalkyl, a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-50}$ linear or branched alkenyl, for example, there may be exemplified a $C_{2-20}$ linear or branched alkenyl or a $C_{8-20}$ linear or branched alkenyl, specifically octadecenyl, dodecenyl, linolyl, vinyl, propenyl or allyl, and so on. As the $C_{6-50}$ aryl, for example, there may be exemplified a $C_{6-20}$ aryl or a $C_{6-10}$ aryl, specifically phenyl or naphthyl. Herein, by optionally substituted, it refers to optionally substituted by one or more (for example, from 1 to 4, from 1 to 3, from 1 to 2 or 1) substituent selected from the group consisting of hydroxyl, a $C_{1-20}$ linear or branched alkyl, a $C_{5-10}$ monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_{5-10}$ monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl.

According to this invention, in the formula (A), the group X' represents a halogen atom, including fluorine atom, chlorine atom, bromine atom and iodine atom, wherein preference is given to chlorine atom.

According to this invention, in Step (2), the ratio by molar of the multifunctional compound (for example, the amine compound represented by the formula (X)) to the quaternizing agent represented by the formula (A) could be generally 1:0.1-200, preferably 1:0.1-50, but not limiting thereto, as long as the quaternizing agent is used with an amount needed to convert at least one N atom in the molecular structure of the ether product into its corresponding quaternary ammonium salt group.

According to this invention, in Step (2), the reaction temperature could be generally 0-300 degrees Celsius, preferably 50-150 degrees Celsius, the reaction duration could be generally 1-20 h, preferably from 4 to 15 h, while the reaction pressure could be any pressure suitable for this reaction, for example, the normal pressure.

According to this invention, Step (2) could be conducted in the presence of or in the absence of a catalyst. As the catalyst, any catalyst conventionally used in this field for a similar purpose may be used as such, specifically KI. As the amount of the catalyst to be used, any amount conventionally used in this field may be mentioned, e.g. 0.5-3.0 wt %, especially 1.0-2.0 wt %.

According to this invention, upon completion of Step (2), any separation method conventionally used in this field could be used to treat the reaction product mixture obtained from Step (2), whereby isolating the cationic-nonionic surfactant. As the separation method, for example, there may be exemplified extraction under an alkali condition.

Step (3): reacting the cationic-nonionic surfactant with one or more compound(s) represented by the following formula (Z) in the presence of an alkaline catalyst, whereby obtaining the anionic-cationic-nonionic surfactant of this invention (including the compound as substantially represented by the formula (I), the compound as substantially represented by the formula (I-1), the compound as substantially represented by the formula (I-2), the compound as substantially represented by the formula (I-3) or the compound as substantially represented by the formula (I-4)).

According to this invention, in Step (3), as the alkaline catalyst, any alkaline catalyst conventionally used in this field for a similar purpose may be used as such, wherein preference is given to alkali metal hydroxide, especially NaOH or KOH. As the alkaline catalyst, one kind or a mixture of two or more kinds at any ratio therebetween could be used.

According to this invention, in Step (3), as the amount of the alkaline catalyst to be used, any amount conventionally used in this field may be mentioned, but could be generally determined such that the ratio by molar of the multifunctional compound (e.g. The amine compound represented by the formula (X)) to the alkaline catalyst is 1:1-10, preferably 1:1-5.

$$G-L-AS \quad (Z)$$

According to this invention, in the formula (Z), the group G represents a halogen atom or hydroxyl, preferably a halogen atom. As the halogen atom, for example, there may be exemplified fluorine atom, chlorine atom, bromine atom and iodine atom, preferably chlorine atom.

According to this invention, in the formula (Z), the group L represents an optionally substituted $C_{1-10}$ linear or branched alkylene or an optionally substituted $C_{2-10}$ linear or branched alkenylene, preferably an optionally substituted $C_{1-5}$ linear or branched alkylene.

According to this invention, in the formula (Z), the group AS represents a group represented by the formula $-A^-(M')_r^+$, wherein the group $A^-$ represents a carboxylate ion ($COO^-$) or a sulfonate ion ($SO_3^-$), the group M' represents hydrogen, alkali metal (preferably Li, Na or K), alkaline earth metal (preferably Mg or Ca) or ammonium ($NH_4$), preferably alkali metal (preferably Li, Na or K) or alkaline earth metal (preferably Mg or Ca).

According to this invention, when the group M' represents hydrogen, alkali metal or ammonium, r=1; when the group M' represents alkaline earth metal, r=0.5.

According to an embodiment of this invention, in the formula (Z), when the group $A^-$ represents the carboxylate ion ($COO^-$), the group G represents the halogen atom, and when the group $A^-$ represents the sulfonate ion ($SO_3^-$), the group G represents the halogen atom or hydroxyl.

According to an embodiment of this invention, one or more compounds represented by the formula (Z) will be used, wherein for at least one compound represented by the formula (Z), the group $A^-$ represents a carboxylate ion ($COO^-$). In this context, to conduct Step (3), it is preferred that at least a compound represented by the formula (Z) bearing a carboxylate ion ($COO^-$) group be used.

According to this invention, in the formula (Z), by optionally substituted, it refers to optionally substituted by one or more (for example, from 1 to 5, from 1 to 4, from 1 to 3, from 1 to 2 or 1) substituent selected from the group consisting of hydroxyl, a $C_{1-20}$ linear or branched alkyl, a $C_5$-10 monocyclic or polycyclic cycloalkyl, a $C_{2-20}$ linear or branched alkenyl and a $C_{6-20}$ aryl. As the $C_{1-20}$ linear or branched alkyl, for example, there may be exemplified a $C_{1-10}$ linear or branched alkyl or a $C_{1-6}$ linear or branched alkyl, or methyl or ethyl, and so on. As the $C_5$-10 monocyclic or polycyclic cycloalkyl, for example, there may be exemplified a $C_{5-8}$ monocyclic or polycyclic cycloalkyl or a $C_{5-7}$ monocyclic or polycyclic cycloalkyl, especially a $C_{5-7}$ monocyclic cycloalkyl, specifically cyclopentyl or cyclohexyl. As the $C_{2-20}$ linear or branched alkenyl, for example, there may be exemplified a $C_{2-10}$ linear or branched alkenyl, specifically vinyl, propenyl or allyl, and so on. As the $C_{6-20}$ aryl, for example, there may be exemplified a $C_{6-10}$ aryl, specifically phenyl or naphthyl.

According to this invention, in Step (3), the ratio by molar of the multifunctional compound (for example, the amine compound represented by the formula (X)) to the compound represented by the formula (Z) is generally 1:1-10, preferably 1:1-3.

According to this invention, in Step (3), the reaction temperature could be generally from 0 to 300 degrees Celsius, preferably 50-200 degrees Celsius, the reaction duration could be generally 1-20 h, preferably from 4 to 10 h, while the reaction pressure could be any pressure suitable for this reaction, for example, the normal pressure.

According to this invention, upon completion of Step (3), the reaction product mixture obtained from Step (3) could be treated by any conventionally known separation method, whereby isolating the surfactant. As the separation method, for example, there may be exemplified a method wherein firstly, into the reaction product mixture obtained from Step (3), an aqueous acidic solution (for example, an aqueous solution of HCl, an aqueous solution of $H_2SO_4$, an aqueous solution of phosphoric acid, an aqueous solution of $NaHSO_4$, or an aqueous solution of $KHSO_4$) is introduced till a pH value from 1 to 3 is reached, then an oil-aqueous phase separation is conducted, whereby obtaining the anionic-cationic-nonionic surfactant of this invention as the oil phase.

According to this invention, upon completion of Step (3), if needed, the thus obtained anionic-cationic-nonionic surfactant could be further made into contact with a neutralizing agent, whereby any free acid (for example, a free carboxylic acid or a free sulfonic acid) group on the surfactant being converted into its corresponding salt (hereinafter referred to as neutralizing step). As the neutralizing agent, for example, there may be exemplified alkali metal (preferably Li, Na or K) hydroxides, alkaline earth metal (preferably Mg or Ca) hydroxides or aqueous ammonia. As the neutralizing agent, one kind or a mixture of two or more kinds at any ratio therebetween could be used. As the way to conduct the neutralizing step, for example, there may be exemplified a method wherein into the anionic-cationic-nonionic surfactant, a predetermined amount of the neutralizing agent in the form of an aqueous solution or an aqueous suspension is introduced till a pH value of 7-9 or 8-10 is reached, then water is removed therefrom (for example, by evaporation under heat or vacuum), but not limiting thereto.

Step (4): if needed, at least a part (or all) of the quaternary ammonium salt group on the molecular structure of the anionic-cationic-nonionic surfactant obtained from any step (including Step (3) and the neutralizing step, and Step (5) as hereinafter described, and so on) of the process of this invention is converted into the corresponding quaternary ammonium hydroxide group, and/or, at least a part (or all) of the quaternary ammonium hydroxide group on the molecular structure of the thus obtained anionic-cationic-nonionic surfactant is converted into the corresponding quaternary ammonium salt group.

According to this invention, Step (4) is an optional step, not an indispensable step.

According to this invention, Step (4) could be conducted in any conventional manner, for example, by electrolyzation or ion exchanging, without any specific limitation thereto.

Step (5): from the anionic-cationic-nonionic surfactant obtained from any step (including Step (3), Step (4) and the neutralizing step) of the process of this invention, at least a part (preferably all) of the compound $(M')_rX'$ (corresponding to the aforesaid inorganic compound represented by the formula $(M)_r^+X^-$) present in a free form is isolated. Herein, the group $(M')r$ is derived from the compound represented by the formula (Z), the group X' is derived from the quaternizing agent represented by the formula (A). The compound $(M')_rX'$ is mainly generated during say Step (3) or Step (4) due to the contacting of the ionic groups $(M')_r^+$ and the ionic groups which are highly chemically reactive to each other. By the isolation, as aforesaid, an anionic-cationic-nonionic surfactant of this invention that substantially all or at least a part thereof presents in the form of betaine is obtained. Obviously, it is also acceptable to not isolate this compound $(M')_rX'$ (i.e. remaining same in the anionic-cationic-nonionic surfactant as a free salt), whereby rendering same as a constituting component of the anionic-cationic-nonionic surfactant of this invention (as a mixed-in component or harmless impurity). All of the obtained anionic-cationic-nonionic surfactants as aforesaid, no matter being or being not subject to the isolation, are all referred to as anionic-cationic-nonionic surfactant of this invention without distinction, and all covered by the present protection scope.

According to this invention, Step (5) is an optional step, not an indispensable step, and not identified as a step for purifying the anionic-cationic-nonionic surfactant of this invention.

According to this invention, as a method for isolating the compound $(M')_rX'$, for example, there is exemplified a method wherein the anionic-cationic-nonionic surfactant obtained from any step (including Step (3), Step (4) and the neutralizing step, and so on) of the process of this invention is dissolved in a massive amount of absolute ethanol, and then the compound is removed by filtration, but not limiting thereto. Due to good solubility of the compound $(M')_rX'$ in water, at least a part thereof may have been isolated and removed by dissolving in water during the production (for example, in Step (3)) of the anionic-cationic-nonionic surfactant of this invention. Since the presence or absence of the compound $(M')_rX'$ or the amount thereof does not substantially change the performances (for example, the interfacial activity and the stability) of the anionic-cationic-nonionic surfactant produced by this invention, this invention does not intend to specify the amount of the compound $(M')_rX'$ or in what form it presents in the anionic-cationic-nonionic surfactant produced by the present process, and for a similar reason, and for this reason, it is not absolutely necessary to remove the compound $(M')_rX'$ from any of the anionic-cationic-nonionic surfactants obtained by this invention as aforesaid.

According to this invention, the anionic-cationic-nonionic surfactant (including the compound as substantially represented by the formula (I), the compound as substantially represented by the formula (I-1), the compound as substantially represented by the formula (I-2), the compound as substantially represented by the formula (I-3) or the compound as substantially represented by the formula (I-4)) could be presented, produced or used in the form of one single kind of compound or a mixture of two or more kinds or a mixture with the aforesaid compound $(M')_rX'$. All these forms are covered by this invention and identified as being effective and desirable in this invention. In this context, according to this invention, it is not absolutely necessary to further purify the thus produced anionic-cationic-nonionic surfactant, or to further isolate one or more specific compound from the thus produced anionic-cationic-nonionic surfactant (if as a mixture). Nevertheless, as the purification or isolation method, there may be exemplified column chromatography or preparative chromatography.

According to this invention, in the anionic-cationic-nonionic surfactant of this invention, different molecules of the anionic-cationic-nonionic surfactant may each independently present, or associate with each other due to the interaction between cations and anions, or even chemically react with each other (for example, by eliminating the compound represented by the formula $(M)_r^+X^-$ or $(M')_rX'$) to form a new compound, without any specific limitation thereto. These forms are all covered by this invention, not limited by any literal wording.

In the anionic-cationic-nonionic surfactant according to this invention, there exists a strong electrostatic attraction between the opposite anionic charges and cationic charges, which significantly increases the amount of the surfactant molecule adsorbed at the interface and significantly reduces the critical micelle concentration, exhibits a much higher interfacial activity as compared with one single type of surfactant. At the same time, thanks to the significantly higher interfacial activity of the present anionic-cationic-nonionic surfactant, an aqueous solution thereof exhibits significantly lowered interfacial tension for crude oil, whereby facilitating reduction of the cohesive force inside crude oil, which facilitates outflow of crude oil and greatly enhances the oil displacement efficiency. On the other hand, the present anionic-cationic-nonionic surfactant can change the surface wettability of crude oil. Specifically, the cationic moiety in the anionic-cationic-nonionic surfactant desorbs the negatively charged groups adsorbed on a solid surface by reacting with same, whereby changing the oil wettable surface into a neutral or water wettable surface, decreasing the adhesion work of crude oil to the solid surface, which will facilitate stripping of crude oil. At the same time, the present anionic-cationic-nonionic surfactant solubilizes crude oil, which helps to wash down any crude oil attached to strata rock or sand, whereby enhancing the oil recovery. In this context, the anionic-cationic-nonionic surfactant according to this invention is particularly suitable for producing a flooding fluid composition for tertiary oil recovery (a flooding fluid).

According to an embodiment of this invention, further related to is a flooding fluid composition for tertiary oil recovery, which comprises the anionic-cationic-nonionic surfactant of this invention as aforesaid and water.

According to this invention, in the flooding fluid composition for tertiary oil recovery, on the basis of the total weight of the flooding fluid composition for tertiary oil recovery (as 100 wt %), the anionic-cationic-nonionic surfactant of this invention accounts for 0.001-10 wt %, preferably 0.005-5 wt %, more preferably 0.02-1 wt %.

According to this invention, the flooding fluid composition for tertiary oil recovery could further (if needed) comprise an additive conventionally used in this field for this purpose, including but not limiting to, a cationic water-soluble polymer, an anionic water-soluble polymer, or a fatty alcohol ether (as the solvent), and so on. As the additive, one kind or a mixture of two or more kinds at any ratio therebetween could be used, at an amount conventionally used in this field.

According to this invention, as the cationic water-soluble polymer, for example, there may be exemplified polyacrylamide. The polyacrylamide may have a number averaged molecular weight of generally from 10000000 to 40000000, preferably from 10000000 to 30000000, at an amount of 0.05-5.0 wt %, preferably 0.1-0.5 wt %, on the basis of the total weight of the flooding fluid composition for tertiary oil recovery, but not limiting thereto.

According to this invention, the flooding fluid composition for tertiary oil recovery exhibits a high oil displacement efficiency and a high oil washing capability even in the absence of an inorganic alkali as a component. In this context, according to a preferred embodiment of this invention, the present flooding fluid composition for tertiary oil recovery contains no (or is not intentionally added with) inorganic alkali as a component. As the inorganic alkali, for example, there may be exemplified any inorganic alkaline compound conventionally used in this field for or with a flooding fluid composition for tertiary oil recovery, especially alkali metal carbonates, for example, sodium carbonate, sodium bicarbonate, and so on.

According to this invention, the flooding fluid composition for tertiary oil recovery could be produced in line with the following process.

According to this invention, the process for producing the flooding fluid composition for tertiary oil recovery includes a step of mixing the anionic-cationic-nonionic surfactant of this invention as aforesaid with water (and if needed, the aforesaid additive) say till homogeneous. Herein, the amount of the anionic-cationic-nonionic surfactant and that of the additive are as aforesaid defined.

According to this invention, the anionic-cationic-nonionic surfactant or the flooding fluid composition for tertiary oil recovery could be used in a tertiary oil recovery process, and exhibits significantly improved oil displacement efficiency and oil washing capability (for example, with an oil washing rate of more than 40% for crude oil) as compared with the prior art, whereby significantly enhancing crude oil recovery. In this context, this invention further relates to a tertiary oil recovery process, including a step of conducting tertiary oil recovery in the presence of as a flooding fluid, the anionic-cationic-nonionic surfactant of this invention as aforesaid or the flooding fluid composition for tertiary oil recovery of this invention as aforesaid.

According to a preferred embodiment of this invention, when conducting the tertiary oil recovery process, no inorganic alkali will be used or be intentionally involved. In this context, the tertiary oil recovery process of this invention shows no harm to the reservoir and oil wells, not corrosive to equipments and pipings, and causes no demulsification difficulty.

According to this invention, the anionic-cationic-nonionic surfactant or flooding fluid composition for tertiary oil recovery is well soluble in water, and even at elevated temperatures, is capable of forming a stable and clear/transparent aqueous solution with water, without formation of precipitation, whereby exhibiting excellent stability in chemical composition and interfacial activity. Further, the aqueous solution remains clear and transparent even after stored (even at elevate temperatures) for a long term, whereby exhibiting an excellent long term stability in chemical composition. Further, it is preferred according to this invention that the anionic-cationic-nonionic surfactant, the flooding fluid composition for tertiary oil recovery or an aqueous solution thereof, even after stored (especially at elevate temperatures) for a long term, remains substantially stable with its interfacial activity, whereby exhibiting an excellent long term stability in terms of interfacial activity.

According to this invention, the anionic-cationic-nonionic surfactant is (substantially) not associated with a chromatographic fractionation problem (i.e. not suffering from the component fractionation problem) in use, whereby exhibiting an excellent stability in terms of chemical composition and interfacial activity in use.

EXAMPLE

The present invention is further specifically illustrated by referring to the following examples and comparative examples, but not limiting to same.

Example 1

20 mol dodecyl aniline and 2 mol chloromethane were introduced into a reactor, heated to a temperature of 80 degrees Celsius, reacted for 5 h, and then was purified by chromatography to obtain (4-dodecyl phenyl) methyl amine. 1 mol (4-dodecyl phenyl) methyl amine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 1 mol propylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1.1 mol chloromethane as the quaternizing agent. The reaction system was heated to a temperature of 80 degrees Celsius and then reacted for 3-10 h, depressurized to remove excessive chloromethane as the quaternizing agent and ethanol as the solvent to obtain a quaternized product (i.e. hereinafter cationic-nonionic surfactant). 1 mol of the quaternized product, 10 L benzene as the solvent and 1.1 mol KOH were introduced into a reactor, heated to a temperature of 80 degrees Celsius, continuously stirred, water generated from the reaction system was distilled away under azeotropy until the quaternized product was converted into the corresponding potassium salt, then there was added 1.1 mol sodium chloroacetate as the carboxylating agent, reacted for 5 h, and then the resultant was adjusted with HCl to an acidic pH value, washed with a 15% NaCl aqueous solution twice, converted with a NaOH aqueous solution into the corresponding sodium salt, then the resultant was dissolved in a massive amount of absolute ethanol, removing by filtration any inorganic salt in the resultant, removing the solvent ethanol by distillation under vacuum to obtain an anionic-cationic-nonionic surfactant, the chemical structure of which was listed in Table 1 as 1-1, and the 1H NMR spectrum of which was listed in Table 5.

Example 2

20 mol 4-nonylaniline and 2 mol chloromethane were introduced into a reactor, heated to a temperature of 80 degrees Celsius, reacted for 5 h, and then was purified by chromatography to obtain (4-nonylphenyl) methyl amine. 1 mol (4-nonylphenyl) methyl amine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 1 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1.1 mol chloromethane as the quaternizing agent. The reaction system was heated to a temperature of 80 degrees Celsius and then reacted for 3-10 h, depressurized to remove excessive chloromethane as the quaternizing agent and ethanol as the solvent to obtain a quaternized product. Then 1 mol of the quaternized product and 10 L benzene as the solvent and 1.1 mol KOH were introduced into a reactor, heated to a temperature of 80 degrees Celsius, continuously stirred, water generated from the reaction system was distilled away under azeotropy until the quaternized product was converted into the corresponding potassium alkoxide, 1.1 mol sodium chloroacetate as the carboxylating agent were introduced into the reactor, reacted for 5 h, and then, the resultant was adjusted with HCl to an acidic pH value, washed with a 15% NaBr aqueous solution twice, converted with aqueous ammonia into the corresponding ammonium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 1 as 1-2, and the 1H NMR spectrum of which was listed in Table 5.

Example 3

20 mol 9-octadecenyl amine and 2 mol allyl chloride were introduced into a reactor, heated to a temperature of 80 degrees Celsius, reacted for 5 h, and then was purified by chromatography to obtain (9-octadecenyl) allyl amine. 1 mol (9-octadecenyl) allyl amine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 49 mol propylene oxide was introduced into the reactor, reacted for 5 h, and then with the help of nitrogen gas at the pressure of 0.8 MPa 37 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1.1 mol allyl chloride as the quaternizing agent. The reaction system was heated to a temperature of 80 degrees Celsius and then reacted for 3-10 h, depressurized to remove excessive allyl chloride as the quaternizing agent and ethanol as the solvent to obtain a quaternized product. Then 1 mol of the quaternized product, 10 L benzene as the solvent and 1.1 mol KOH were introduced into a reactor, heated to a temperature of 80 degrees Celsius, continuously stirred, water generated from the reaction system was distilled away under azeotropy until the quaternized product was converted into the corresponding potassium alkoxide. 1.1 mol sodium chloroacetate as the carboxylating agent was introduced into the reactor, reacted for 5 h, and then, the resultant was adjusted with HCl to an acidic pH value, washed with a 15% NaI aqueous solution twice, converted with a KOH aqueous solution into the corresponding potassium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 1 as 1-3, and the 1H NMR spectrum of which was listed in Table 5.

Example 4

20 mol isotridecyl aniline and 2 mol benzyl chloride were introduced into a reactor, heated to a temperature of 80 degrees Celsius, reacted for 5 h, and then was purified by chromatography to obtain isotridecyl benzyl amine. 1 mol isotridecyl benzyl amine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 39 mol propylene oxide was introduced into the reactor, reacted for 5 h, and then with the help of nitrogen gas at the pressure of 0.8 MPa 41 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1.1 mol benzyl chloride as the quaternizing agent. The reaction system was heated to a temperature of 80 degrees Celsius and then reacted for 3-10 h, depressurized to remove excessive benzyl chloride as the quaternizing agent and ethanol as the solvent to obtain a quaternized product. Then 1 mol of the quaternized product, 10 L benzene as the solvent and 1.1 mol KOH were introduced into a reactor, heated to a temperature of 80 degrees Celsius, continuously stirred, water generated from the reaction system was distilled away under azeotropy until the quaternized product was converted into the corresponding potassium alkoxide. 1.1 mol sodium chloroacetate as the carboxylating agent was introduced into the reactor, reacted for 5 h, and then, the resultant was adjusted with HCl to an acidic pH value, washed with a 15% NaCl aqueous solution twice, converted with a CaOH aqueous solution into the corresponding calcium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 1 as 1-4, and the 1H NMR spectrum of which was listed in Table 5.

Example 5

20 mol dinonylbenzyl amine and 2 mol 2-chloropropane were introduced into a reactor, heated to a temperature of 80 degrees Celsius, reacted for 5 h, and then was purified by chromatography to obtain iso(dinonylbenzyl) isopropyl amine. 1 mol iso(dinonylbenzyl) isopropyl amine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 1 mol propylene oxide was introduced into the reactor, reacted for 5 h, and then with the help of nitrogen gas at the pressure of 0.8 MPa 39 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1.1 mol 2-chloropropane as the quaternizing agent. The reaction system was heated to a temperature of 80 degrees Celsius and then reacted for 3-10 h, depressurized to remove excessive 2-chloropropane as the quaternizing agent and ethanol as the solvent to obtain a quaternized product. Then 1 mol of the quaternized product, 10 L benzene as the solvent and 1.1 mol KOH were introduced into a reactor, heated to a temperature of 80 degrees Celsius, continuously stirred, water generated from the reaction system was distilled away under azeotropy until the quaternized product was converted into the corresponding potassium alkoxide. 1.1 mol sodium chloroacetate as the carboxylating agent was introduced into the reactor, reacted for 5 h, and then, the resultant was adjusted with HCl to an acidic pH value, washed with a 15% NaBr aqueous solution twice, converted with a MgOH aqueous solution into the corresponding magnesium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 1 as 1-5, and the 1H NMR spectrum of which was listed in Table 5.

Example 6

20 mol dodecyl benzyl amine and 2 mol chloroethane were introduced into a reactor, heated to a temperature of 80 degrees Celsius, reacted for 5 h, and then was purified by chromatography to obtain (dodecyl benzyl) ethyl amine. 1 mol (dodecyl benzyl) ethyl amine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 21 mol ethylene oxide was introduced into the reactor, reacted for 5 h, and then with the help of nitrogen gas at the pressure of 0.8 MPa 17 mol propylene oxide was introduced into the reactor, reacted for 5 h to obtain an ether product. The whole amount of the ether product was dissolved in absolute ethanol and formulated into a 40% solution and then added to a reactor, with the help of nitrogen gas at the pressure of 0.8 MPa, there was added 1.1 mol chloroethane as the quaternizing agent. The reaction system was heated to a temperature of 80 degrees Celsius and then reacted for 3-10 h, depressurized to remove excessive chloroethane as the quaternizing agent and ethanol as the solvent to obtain a quaternized product. Then 1 mol of the quaternized product, 10 L benzene as the solvent and 1.1 mol KOH were introduced into a reactor, heated to a temperature of 80 degrees Celsius, continuously stirred, water generated from the reaction system was distilled away under azeotropy until the quaternized product was converted into the corresponding potassium alkoxide. 1.1 mol sodium chloroacetate as the carboxylating agent was introduced into the reactor, reacted for 5 h, and then, the resultant was adjusted with HCl to an acidic pH value, washed with a 15% NaI aqueous solution twice, converted with a KOH aqueous solution into the corresponding potassium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 1 as 1-6, and the 1H NMR spectrum of which was listed in Table 5.

Example 7

1 mol methyl dodecyl-3-amino benzoate, 2 mol isopropanolamine and 0.1 mol KOH were introduced into a reactor, heated to a temperature of 180 degrees Celsius, reacted for 5 h, and then was purified by chromatography to obtain dodecyl-3-amino benzoyl isopropanolamine. 1 mol dodecyl-3-amino benzoyl isopropanolamine and 0.1 mol KOH were added to a reactor, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 11 mol propylene oxide was introduced into the reactor, reacted for 5 h, and then with the help of nitrogen gas at the pressure of 0.8 MPa 27 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1.1 mol allyl chloride as the quaternizing agent. The reaction system was heated to a temperature of 80 degrees Celsius and then reacted for 3-10 h, depressurized to remove excessive allyl chloride as the quaternizing agent and ethanol as the solvent to obtain a quaternized product. Then 1 mol of the quaternized product, 10 L benzene as the solvent and 1.1 mol KOH were introduced into a reactor, heated to a temperature of 80 degrees Celsius, continuously stirred, water generated from the reaction system was distilled away under azeotropy until the quaternized product was converted into the corresponding potassium alkoxide. 1.1 mol sodium chloroacetate as the carboxylating agent was introduced into the reactor, reacted for 5 h, and then, the resultant was adjusted with HCl to an acidic pH value, washed with a 15% NaBr aqueous solution twice, converted with aqueous ammonia into the corresponding ammonium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 1 as 1-7, and the 1H NMR spectrum of which was listed in Table 5.

Example 8

10 mol 5-eicosanyl m-phenylenediamine and 20 mol benzyl chloride were introduced into a reactor, heated to a temperature of 80 degrees Celsius, reacted for 5 h, and then was purified by chromatography to obtain N, N'-dibenzyl-5-eicosanyl m-phenylenediamine. 1 mol N, N'-dibenzyl-5-eicosanyl m-phenylenediamine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 2 mol propylene oxide was introduced into the reactor, reacted for 5 h, and then with the help of nitrogen gas at the pressure of 0.8 MPa 48 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 2.2 mol benzyl chloride as the quaternizing agent. The reaction system was heated to a temperature of 80 degrees Celsius and then reacted for 3-10 h, depressurized to remove excessive benzyl chloride as the quaternizing agent and ethanol as the solvent to obtain a quaternized product. Then 1 mol of the quaternized product, 10 L benzene as the solvent and 2.2 mol KOH were introduced into a reactor, heated to a temperature of 80 degrees Celsius, continuously stirred, water generated from the reaction system was distilled away under azeotropy until the quaternized product was converted into the corresponding potassium alkoxide. 2.2 mol chloromethyl sodium sulfonate as the sulfonating agent was introduced into the reactor, reacted for 5 h, and then, the resultant was adjusted with HCl to an acidic pH value, washed with a 15% NaI aqueous solution twice, converted with a KOH aqueous solution into the corresponding potassium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 1 as 1-8, and the 1H NMR spectrum of which was listed in Table 5.

Example 9

20 mol dodecyl amine and 2 mol chloromethane were introduced into a reactor, heated to a temperature of 80 degrees Celsius, reacted for 5 h, and then was purified by chromatography to obtain dodecyl methyl amine. 1 mol dodecyl methyl amine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 1 mol propylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1.1 mol chloromethane as the quaternizing agent. The reaction system was heated to a temperature of 80 degrees Celsius and then reacted for 3-10 h, depressurized to remove excessive chloromethane as the quaternizing agent and ethanol as the solvent to obtain a quaternized product. Then 1 mol of the quaternized product, 10 L benzene as the solvent and 1.1 mol KOH were introduced into a reactor, heated to a temperature of 80 degrees Celsius, continuously stirred, water generated from the reaction system was distilled away under azeotropy until the quaternized product was converted into the corresponding potassium alkoxide. 1.1 mol sodium chloroacetate as the carboxylating agent was introduced into the reactor, reacted for 5 h, and then, the resultant was adjusted with HCl to an acidic pH value, washed with a 15% NaCl aqueous solution twice, converted with a NaOH aqueous solution into the corresponding sodium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 2 as 2-1, and the 1H NMR spectrum of which was listed in Table 6.

Example 10

20 mol oleyl amine and 2 mol chloromethane were introduced into a reactor, heated to a temperature of 80 degrees Celsius, reacted for 5 h, and then was purified by chromatography to obtain 9-octadecenyl methyl amine. 1 mol 9-octadecenyl methyl amine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 1 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1.1 mol chloromethane as the quaternizing agent. The reaction system was heated to a temperature of 80 degrees Celsius and then reacted for 3-10 h, depressurized to remove excessive chloromethane as the quaternizing agent and ethanol as the solvent to obtain a quaternized product. Then 1 mol of the quaternized product, 10 L benzene as the solvent and 1.1 mol KOH were introduced into a reactor, heated to a temperature of 80 degrees Celsius, continuously stirred, water generated from the reaction system was distilled away under azeotropy until the quaternized product was converted into the corresponding potassium alkoxide. 1.1 mol sodium chloroacetate as the carboxylating agent was introduced into the reactor, reacted for 5 h, and then, the resultant was adjusted with HCl to an acidic pH value, washed with a 15% NaBr aqueous solution twice, converted with aqueous ammonia into the corresponding ammonium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 2 as 2-2, and the 1H NMR spectrum of which was listed in Table 6.

Example 11

20 mol rosinyl amine and 2 mol 1-chlorooctane were introduced into a reactor, heated to a temperature of 80 degrees Celsius, reacted for 5 h, and then was purified by chromatography to obtain rosinyl octyl amine. 1 mol rosinyl octyl amine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 49 mol propylene oxide was introduced into the reactor, reacted for 5 h, and then with the help of nitrogen gas at the pressure of 0.8 MPa 37 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1 mol 1-chlorooctane as the quaternizing agent. The reaction system was heated to a temperature of 80 degrees Celsius and then reacted for 3-10 h, depressurized to remove excessive ethanol as the solvent to obtain a quaternized product. Then 1 mol of the quaternized product, 10 L benzene as the solvent and 1.1 mol KOH were introduced into a reactor, heated to a temperature of 80 degrees Celsius, continuously stirred, water generated from the reaction system was distilled away under azeotropy until the quaternized product was converted into the corresponding potassium alkoxide. 1.1 mol sodium chloroacetate as the carboxylating agent was introduced into the reactor, reacted for 5 h, and then, the resultant was adjusted with HCl to an acidic pH value, washed with a 15% NaBr aqueous solution twice, converted with a MgOH aqueous solution into the corresponding magnesium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 2 as 2-3, and the 1H NMR spectrum of which was listed in Table 6.

Example 12

20 mol isotridecyl amine and 2 mol allyl chloride were introduced into a reactor, heated to a temperature of 80 degrees Celsius, reacted for 5 h, and then was purified by chromatography to obtain isotridecyl allyl amine. 1 mol isotridecyl allyl amine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 25 mol propylene oxide was introduced into the reactor, reacted for 5 h, and then with the help of nitrogen gas at the pressure of 0.8 MPa 17 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1.1 mol allyl chloride as the quaternizing agent. The reaction system was heated to a temperature of 80 degrees Celsius and then reacted for 3-10 h, depressurized to remove excessive allyl chloride as the quaternizing agent and ethanol as the solvent to obtain a quaternized product. Then 1 mol of the quaternized product, 10 L benzene as the solvent and 1.1 mol KOH were introduced into a reactor, heated to a temperature of 80 degrees Celsius, continuously stirred, water generated from the reaction system was distilled away under azeotropy until the quaternized product was converted into the corresponding potassium alkoxide. 1.1 mol sodium chloroacetate as the carboxylating agent was introduced into the reactor, reacted for 5 h, and then, the resultant was adjusted with HCl to an acidic pH value, washed with a 15% NaI aqueous solution twice, converted with a CaOH aqueous solution into the corresponding calcium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 2 as 2-4, and the 1H NMR spectrum of which was listed in Table 6.

Example 13

5 mol lysine methyl ester and 10 mol monoethanolamine were introduced into a reactor, heated to a temperature of 180 degrees Celsius, reacted for 5 h, and then was purified by chromatography to obtain lysine monoethanol amide. 5 mol lysine monoethanol amide and 10 mol 1-chlorooctane were introduced into a reactor, heated to a temperature of 80 degrees Celsius, reacted for 5 h, and then was purified by chromatography to obtain N,N'-dioctyl lysine monoethanol amide. 1 mol N,N'-dioctyl lysine monoethanol amide and KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 39 mol ethylene oxide was introduced into the reactor, reacted for 5 h, and then with the help of nitrogen gas at the pressure of 0.8 MPa 15 mol propylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 2 mol 1-chlorooctane as the quaternizing agent. The reaction system was heated to a temperature of 80 degrees Celsius and then reacted for 3-10 h, depressurized to remove ethanol as the solvent to obtain a quaternized product. Then 1 mol of the quaternized product, 10 L benzene as the solvent and 3.3 mol KOH were introduced into a reactor, heated to a temperature of 80 degrees Celsius, continuously stirred, water generated from the reaction system was distilled away under azeotropy until the quaternized product was converted into the corresponding potassium alkoxide. 3.3 mol sodium chloroacetate as the carboxylating agent was introduced into the reactor, reacted for 5 h, and then, the resultant was adjusted with HCl to an acidic pH value, washed with a 15% NaBr aqueous solution twice, converted with a MgOH aqueous solution into the corresponding magnesium salt. The resultant was dissolved in a massive amount of absolute ethanol, removing by filtration any inorganic salt in the resultant, the solvent was removed by vacuum distillation to obtain an anionic-cationic surfactant, the chemical structure of which was listed in Table 2 as 2-5, and the 1H NMR spectrum of which was listed in Table 6.

Example 14

20 mol octadecylamine and 2 mol benzyl chloride were introduced into a reactor, heated to a temperature of 80 degrees Celsius, reacted for 5 h, and then was purified by chromatography to obtain octadecyl benzyl amine. 1 mol octadecyl benzyl amine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 25 mol propylene oxide was introduced into the reactor, reacted for 5 h, and then with the help of nitrogen gas at the pressure of 0.8 MPa 17 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1.1 mol benzyl chloride as the quaternizing agent. The reaction system was heated to a temperature of 80 degrees Celsius and then reacted for 3-10 h, depressurized to remove excessive ethanol as the solvent to obtain a quaternized product. Then 1 mol of the quaternized product, 10 L benzene as the solvent and 1.1 mol KOH were introduced into a reactor, heated to a temperature of 80 degrees Celsius, continuously stirred, water generated from the reaction system was distilled away under azeotropy until the quaternized product was converted into the corresponding potassium alkoxide. 1.1 mol sodium chloroacetate as the carboxylating agent was introduced into the reactor, reacted for 5 h, and then, the resultant was adjusted with HCl to an acidic pH value, washed with a 15% NaI aqueous solution twice, converted with NaOH into the corresponding sodium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 2 as 2-6, and the 1H NMR spectrum of which was listed in Table 6.

Example 15

1 mol laurylamine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 39 mol ethylene oxide was introduced into the reactor, reacted for 5 h, and then with the help of nitrogen gas at the pressure of 0.8 MPa 1 mol propylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1.1 mol chlorocyclohexane as the quaternizing agent. The reaction system was heated to a temperature of 80 degrees Celsius and then reacted for 3-10 h, depressurized to remove excessive chlorocyclohexane as the quaternizing agent and ethanol as the solvent to obtain a quaternized product. Then 1 mol of the quaternized product, 10 L benzene as the solvent and 2.2 mol KOH were introduced into a reactor, heated to a temperature of 80 degrees Celsius, continuously stirred, water generated from the reaction system was distilled away under azeotropy until the quaternized product was converted into the corresponding potassium alkoxide. 2.2 mol sodium chloroacetate as the carboxylating agent was introduced into the reactor, reacted for 5 h, and then, the resultant was adjusted with HCl to an acidic pH value, washed with a 15% NaCl aqueous solution twice, converted with a NaOH aqueous solution into the corresponding sodium salt. The resultant was dissolved in a massive amount of absolute ethanol, removing by filtration any inorganic salt in the resultant, the solvent was removed by vacuum distillation to obtain an anionic-cationic-non-ionic surfactant, the chemical structure of which was listed in Table 2 as 2-7, and the 1H NMR spectrum of which was listed in Table 6.

Example 16

1 mol palmityl amine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 1 mol propylene oxide was introduced into the reactor, reacted for 5 h, and then with the help of nitrogen gas at the pressure of 0.8 MPa 39 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1.1 mol allyl chloride as the quaternizing agent. The reaction system was heated to a temperature of 80 degrees Celsius and then reacted for 3-10 h, depressurized to remove excessive allyl chloride as the quaternizing agent and ethanol as the solvent to obtain a quaternized product. Then 1 mol of the quaternized product, 10 L benzene as the solvent and 2.2 mol KOH were introduced into a reactor, heated to a temperature of 80 degrees Celsius, continuously stirred, water generated from the reaction system was distilled away under azeotropy until the quaternized product was converted into the corresponding potassium alkoxide. 2.2 mol chloromethyl sodium sulfonate as the sulfonating agent was introduced into the reactor, reacted for 5 h, and then, the resultant was adjusted with HCl to an acidic pH value, washed with a 15% NaCl aqueous solution twice, converted with a CaOH aqueous solution into the corresponding calcium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 2 as 2-8, and the 1H NMR spectrum of which was listed in Table 6.

Example 17

10 mol 1-chlorododecane and 5 mol ammonia were introduced into a reactor, heated to a temperature of 80 degrees Celsius, reacted for 5 h, and then was purified by chromatography to obtain di (dodecyl) amine, then 1 mol di (dodecyl) amine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 14 mol propylene oxide was introduced into the reactor, reacted for 5 h, and then with the help of nitrogen gas at the pressure of 0.8 MPa 9 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1.1 mol chloromethane as the quaternizing agent. The reaction system was heated to a temperature of 80 degrees Celsius and then reacted for 3-10 h, depressurized to remove excessive chloromethane as the quaternizing agent and ethanol as the solvent to obtain a quaternized product. Then 1 mol of the quaternized product, 10 L benzene as the solvent and 1.1 mol KOH were introduced into a reactor, heated to a temperature of 80 degrees Celsius, continuously stirred, water generated from the reaction system was distilled away under azeotropy until the quaternized product was converted into the corresponding potassium alkoxide. 1.1 mol sodium chloroacetate as the carboxylating agent was introduced into the reactor, reacted for 5 h, and then, the resultant was adjusted with HCl to an acidic pH value, washed with a 15% NaI aqueous solution twice, converted with a NaOH aqueous solution into the corresponding sodium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 3 as 3-1, and the 1H NMR spectrum of which was listed in Table 7.

Example 18

2 mol 1-chlorooctadecane and 20 mol diethanol amine were introduced into a reactor, heated to a temperature of 80 degrees Celsius, reacted for 5 h, and then, was purified by chromatography to obtain octadecyl di(hydroxyethyl) amine, then 1 mol octadecyl di(hydroxyethyl) amine and 0.1 mol KOH were added to a reactor and heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 4 mol ethylene oxide was introduced into the reactor, reacted for 5 h, and then with the help of nitrogen gas at the pressure of 0.8 MPa 22 mol propylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1 mol 1-chlorododecane as the quaternizing agent. The reaction system was heated to a temperature of 80 degrees Celsius and then reacted for 3-10 h, depressurized to remove excessive ethanol as the solvent to obtain a quaternized product. Then 1 mol of the quaternized product, 10 L benzene as the solvent and 2.2 mol KOH were introduced into a reactor, heated to a temperature of 80 degrees Celsius, continuously stirred, water generated from the reaction system was distilled away under azeotropy until the quaternized product was converted into the corresponding potassium alkoxide. 2.2 mol sodium chloroacetate as the carboxylating agent was introduced into the reactor, reacted for 5 h, and then, the resultant was adjusted with HCl to an acidic pH value, washed with a 15% NaCl aqueous solution twice, converted with a KOH aqueous solution into the corresponding potassium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 3 as 3-2, and the 1H NMR spectrum of which was listed in Table 7.

Example 19

20 mol oleyl amine and 2 mol 1-chlorododecane were introduced into a reactor, heated to a temperature of 80 degrees Celsius, reacted for 5 h, and then was purified by chromatography to obtain 1-(9-octadecenyl) dodecyl amine, then 1 mol 1-(9-octadecenyl) dodecyl amine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 17 mol propylene oxide was introduced into the reactor, reacted for 5 h, and then with the help of nitrogen gas at the pressure of 0.8 MPa 38 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1.1 mol chlorocyclohexane as the quaternizing agent. The reaction system was heated to a temperature of 80 degrees Celsius and then reacted for 3-10 h, depressurized to remove excessive chlorocyclohexane as the quaternizing agent and ethanol as the solvent to obtain a quaternized product. Then 1 mol of the quaternized product, 10 L benzene as the solvent and 1.1 mol KOH were introduced into a reactor, heated to a temperature of 80 degrees Celsius, continuously stirred, water generated from the reaction system was distilled away under azeotropy until the quaternized product was converted into the corresponding potassium alkoxide. 1.1 mol sodium chloroacetate as the carboxylating agent was introduced into the reactor, reacted for 5 h, and then, the resultant was adjusted with HCl to an acidic pH value, washed with a 15% NaBr aqueous solution twice, converted with a CaOH aqueous solution into the corresponding calcium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 3 as 3-3, and the 1H NMR spectrum of which was listed in Table 7.

Example 20

2 mol 1-chloro-9-octadecene and 20 mol diethanol amine were introduced into a reactor, heated to a temperature of 80 degrees Celsius, reacted for 5 h, and then, was purified by chromatography to obtain (9-octadecenyl) di(hydroxyethyl) amine, then 1 mol (9-octadecenyl) di(hydroxyethyl) amine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 16 mol ethylene oxide was introduced into the reactor, reacted for 5 h, and then with the help of nitrogen gas at the pressure of 0.8 MPa 49 mol propylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1 mol 1-chlorododecane as the quaternizing agent. The reaction system was heated to a temperature of 80 degrees Celsius and then reacted for 3-10 h, depressurized to remove excessive ethanol as the solvent to obtain a quaternized product. Then 1 mol of the quaternized product, 10 L benzene as the solvent and 2.2 mol KOH were introduced into a reactor, heated to a temperature of 80 degrees Celsius, continuously stirred, water generated from the reaction system was distilled away under azeotropy until the quaternized product was converted into the corresponding potassium alkoxide. 2.2 mol sodium chloroacetate as the carboxylating agent was introduced into the reactor, reacted for 5 h, and then, the resultant was adjusted with HCl to an acidic pH value, washed with a 15% NaCl aqueous solution twice, converted with a KOH aqueous solution into the corresponding potassium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 3 as 3-4, and the 1H NMR spectrum of which was listed in Table 7.

Example 21

11 mol methyl oleate and 100 mol ethylenediamine were introduced into a reactor, heated to a temperature of 180 degrees Celsius, reacted for 5 h, and then was purified by chromatography to obtain oleoyl ethylenediamine, then 10 mol oleoyl ethylenediamine and 1 mol 1-chlorododecane were introduced into a reactor, heated to a temperature of 80 degrees Celsius, reacted for 5 h, and then was purified by chromatography to obtain 1-oleoyl-4-lauryl ethylenediamine. 1 mol 1-oleoyl-4-lauryl ethylenediamine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 2 mol propylene oxide was introduced into the reactor, reacted for 5 h, and then with the help of nitrogen gas at the pressure of 0.8 MPa 39 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1.1 mol chlorocyclohexane as the quaternizing agent. The reaction system was heated to a temperature of 80 degrees Celsius and then reacted for 3-10 h, depressurized to remove excessive chlorocyclohexane as the quaternizing agent and ethanol as the solvent to obtain a quaternized product. Then 1 mol of the quaternized product, 10 L benzene as the solvent and 1.1 mol KOH were introduced into a reactor, heated to a temperature of 80 degrees Celsius, continuously stirred, water generated from the reaction system was distilled away under azeotropy until the quaternized product was converted into the corresponding potassium alkoxide. 1.1 mol sodium chloroacetate as the carboxylating agent was introduced into the reactor, reacted for 5 h, and then, the resultant was adjusted with HCl to an acidic pH value, washed with a 15% NaCl aqueous solution twice, converted with a NaOH aqueous solution into the corresponding sodium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 3 as 3-5, and the 1H NMR spectrum of which was listed in Table 7.

Example 22

15 mol methyl laurate and 150 mol ethylenediamine were introduced into a reactor, heated to a temperature of 180 degrees Celsius, reacted for 5 h, and then, was purified by chromatography to obtain 1-lauroyl ethylenediamine, then 12 mol 1-lauroyl ethylenediamine and 1 mol 1-chlorododecyl were introduced into a reactor, heated to a temperature of 80 degrees Celsius, reacted for 5 h, and then, was purified by chromatography to obtain 1-lauroyl-4-dodecyl ethylenediamine. 1 mol 1-lauroyl-4-dodecyl ethylenediamine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 16 mol propylene oxide was introduced into the reactor, reacted for 5 h, and then with the help of nitrogen gas at the pressure of 0.8 MPa 22 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1.1 mol chloroethane as the quaternizing agent. The reaction system was heated to a temperature of 80 degrees Celsius and then reacted for 3-10 h, depressurized to remove excessive chloroethane as the quaternizing agent and ethanol as the solvent to obtain a quaternized product. Then 1 mol of the quaternized product, 10 L benzene as the solvent and 1.1 mol KOH were introduced into a reactor, heated to a temperature of 80 degrees Celsius, continuously stirred, water generated from the reaction system was distilled away under azeotropy until the quaternized product was converted into the corresponding potassium alkoxide. 1.1 mol sodium chloroacetate as the carboxylating agent was introduced into the reactor, reacted for 5 h, and then, the resultant was adjusted with HCl to an acidic pH value, washed with a 15% NaI aqueous solution twice, converted with a KOH aqueous solution into the corresponding potassium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 3 as 3-6, and the 1H NMR spectrum of which was listed in Table 7.

Example 23

20 mol methyl laurate and 200 mol diethylenetriamine were introduced into a reactor, heated to a temperature of 180 degrees Celsius, reacted for 5 h, and then, was purified by chromatography to obtain 1-lauroyl diethylenetriamine, then 2 mol methyl laurate and 10 mol 1-lauroyl diethylenetriamine were introduced into a reactor, heated to a temperature of 180 degrees Celsius, reacted for 5 h, and then, was purified by chromatography to obtain 1, 7-dilauroyl diethylenetriamine. 1 mol 1, 7-dilauroyl diethylenetriamine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 16 mol propylene oxide was introduced into the reactor, reacted for 5 h, and then with the help of nitrogen gas at the pressure of 0.8 MPa 37 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 1.1 mol chloroethane as the quaternizing agent. The reaction system was heated to a temperature of 80 degrees Celsius and then reacted for 3-10 h, depressurized to remove excessive chloroethane as the quaternizing agent and ethanol as the solvent to obtain a quaternized product. Then 1 mol of the quaternized product, 10 L benzene as the solvent and 1.1 mol KOH were introduced into a reactor, heated to a temperature of 80 degrees Celsius, continuously stirred, water generated from the reaction system was distilled away under azeotropy until the quaternized product was converted into the corresponding potassium alkoxide. 1.1 mol sodium chloroacetate as the carboxylating agent was introduced into the reactor, reacted for 5 h, and then, the resultant was adjusted with HCl to an acidic pH value, washed with a 15% NaBr aqueous solution twice, converted with aqueous ammonia into the corresponding ammonium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 3 as 3-7, and the 1H NMR spectrum of which was listed in Table 7.

Example 24

30 mol 1-chlorododecane and 300 mol triethylene tetramine were introduced into a reactor, heated to a temperature of 80 degrees Celsius, reacted for 5 h, and then, was purified by chromatography to obtain 1-lauryl triethylene tetramine, then 2 mol methyl laurate and 20 mol 1-lauryl triethylene tetramine were introduced into a reactor, heated to a temperature of 180 degrees Celsius, reacted for 5 h, and then, was purified by chromatography to obtain 1-lauroyl-10-lauryl triethylene tetramine. 1 mol 1-lauroyl-10-lauryl triethylene tetramine and KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 31 mol propylene oxide was introduced into the reactor, reacted for 5 h, and then with the help of nitrogen gas at the pressure of 0.8 MPa 9 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 3.3 mol allyl chloride as the quaternizing agent. The reaction system was heated to a temperature of 80 degrees Celsius and then reacted for 3-10 h, depressurized to remove excessive allyl chloride as the quaternizing agent and ethanol as the solvent to obtain a quaternized product. Then 1 mol of the quaternized product, 10 L benzene as the solvent and 3.3 mol KOH were introduced into a reactor, heated to a temperature of 80 degrees Celsius, continuously stirred, water generated from the reaction system was distilled away under azeotropy until the quaternized product was converted into the corresponding potassium alkoxide. 3.3 mol 2-chloroethyl sodium sulfonate as the sulfonating agent was introduced into the reactor, reacted for 5 h, and then, the resultant was adjusted with HCl to an acidic pH value, washed with a 15% NaI aqueous solution twice, converted with a CaOH aqueous solution into the corresponding calcium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 3 as 3-8, and the 1H NMR spectrum of which was listed in Table 7.

Example 25

2 mol 1-chlorododecane and 20 mol ethylenediamine were introduced into a reactor, heated to a temperature of 80 degrees Celsius, reacted for 5 h, and then, was purified by chromatography to obtain 1-lauryl ethylenediamine. Then 1 mol 1-lauryl ethylenediamine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 23 mol propylene oxide was introduced into the reactor, reacted for 5 h, and then with the help of nitrogen gas at the pressure of 0.8 MPa 19 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 3.3 mol chloroethane as the quaternizing agent. The reaction system was heated to a temperature of 80 degrees Celsius and then reacted for 3-10 h, depressurized to remove excessive chloroethane as the quaternizing agent and ethanol as the solvent to obtain a quaternized product. Then 1 mol of the quaternized product, 10 L benzene as the solvent and 3.3 mol KOH were introduced into a reactor, heated to a temperature of 80 degrees Celsius, continuously stirred, water generated from the reaction system was distilled away under azeotropy until the quaternized product was converted into the corresponding potassium alkoxide. 3.3 mol sodium chloroacetate as the carboxylating agent was introduced into the reactor, reacted for 5 h, and then, the resultant was adjusted with HCl to an acidic pH value, washed with a 15% NaCl aqueous solution twice, converted with a NaOH aqueous solution into the corresponding sodium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 4 as 4-1, and the 1H NMR spectrum of which was listed in Table 8.

Example 26

2 mol 1-chloro-9-octadecene and 20 mol ethylenediamine were introduced into a reactor, heated to a temperature of 80 degrees Celsius, reacted for 5 h, and then, was purified by chromatography to obtain (9-octadecenyl) ethylenediamine. Then 1 mol (9-octadecenyl) ethylenediamine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 11 mol propylene oxide was introduced into the reactor, reacted for 5 h, and then with the help of nitrogen gas at the pressure of 0.8 MPa 9 mol ethylene oxide was introduced into the reactor, reacted for 5 h to obtain an ether product. The whole amount of the ether product was dissolved in absolute ethanol and formulated into a 40% solution and then added to a reactor, with the help of nitrogen gas at the pressure of 0.8 MPa, there was added 2.2 mol allyl chloride as the quaternizing agent. The reaction system was heated to a temperature of 80 degrees Celsius and then reacted for 3-10 h, depressurized to remove excessive allyl chloride as the quaternizing agent and ethanol as the solvent to obtain a quaternized product. Then 1 mol of the quaternized product, 10 L benzene as the solvent and 3.3 mol KOH were introduced into a reactor, heated to a temperature of 80 degrees Celsius, continuously stirred, water generated from the reaction system was distilled away under azeotropy until the quaternized product was converted into the corresponding potassium alkoxide. 3.3 mol sodium chloroacetate as the carboxylating agent was introduced into the reactor, reacted for 5 h, and then, the resultant was adjusted with HCl to an acidic pH value, washed with a 15% NaI aqueous solution twice, converted with a KOH aqueous solution into the corresponding potassium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 4 as 4-2, and the 1H NMR spectrum of which was listed in Table 8.

Example 27

2 mol methyl laurate and 20 mol ethylenediamine were introduced into a reactor, heated to a temperature of 180 degrees Celsius, reacted for 5 h, and then, was purified by chromatography to obtain lauroyl ethylenediamine. Then 1 mol lauroyl ethylenediamine were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 1 mol propylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 2.2 mol benzyl chloride as the quaternizing agent. The reaction system was heated to a temperature of 80 degrees Celsius and then reacted for 3-10 h, depressurized to remove excessive benzyl chloride as the quaternizing agent and ethanol as the solvent to obtain a quaternized product. Then 1 mol of the quaternized product, 10 L benzene as the solvent and 2.2 mol KOH were introduced into a reactor, heated to a temperature of 80 degrees Celsius, continuously stirred, water generated from the reaction system was distilled away under azeotropy until the quaternized product was converted into the corresponding potassium alkoxide. 2.2 mol sodium chloroacetate as the carboxylating agent was introduced into the reactor, reacted for 5 h, and then, the resultant was adjusted with HCl to an acidic pH value, washed with a 15% NaBr aqueous solution twice, converted with aqueous ammonia into the corresponding ammonium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 4 as 4-3, and the 1H NMR spectrum of which was listed in Table 8.

Example 28

2 mol methyl oleate and 20 mol ethylenediamine were introduced into a reactor, heated to a temperature of 80 degrees Celsius, reacted for 5 h, and then, was purified by chromatography to obtain 1-oleoyl ethylenediamine. Then 1 mol 1-oleoyl ethylenediamine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 47 mol propylene oxide was introduced into the reactor, reacted for 5 h, and then with the help of nitrogen gas at the pressure of 0.8 MPa 32 mol ethylene oxide was introduced into the reactor, reacted for 5 h to obtain an ether product. The whole amount of the ether product was dissolved in absolute ethanol and formulated into a 40% solution and then added to a reactor, with the help of nitrogen gas at the pressure of 0.8 MPa, there was added 1.1 mol chlorocyclohexane as the quaternizing agent. The reaction system was heated to a temperature of 80 degrees Celsius and then reacted for 3-10 h, depressurized to remove excessive chlorocyclohexane as the quaternizing agent and ethanol as the solvent to obtain a quaternized product. Then 1 mol of the quaternized product, 2010 L benzene as the solvent and 2.2 mol KOH were introduced into a reactor, heated to a temperature of 80 degrees Celsius, continuously stirred, water generated from the reaction system was distilled away under azeotropy until the quaternized product was converted into the corresponding potassium alkoxide. 2.2 mol sodium chloroacetate as the carboxylating agent was introduced into the reactor, reacted for 5 h, and then, the resultant was adjusted with HCl to an acidic pH value, washed with a 15% NaI aqueous solution twice, converted with a NaOH aqueous solution into the corresponding sodium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 4 as 4-4, and the 1H NMR spectrum of which was listed in Table 8.

Example 29

2 mol 1-chlorododecane and 20 mol monoethanolamine were introduced into a reactor, heated to a temperature of 180 degrees Celsius, reacted for 5 h, and then, was purified by chromatography to obtain N-lauryl monoethanolamine. Then 1 mol N-lauryl monoethanolamine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 41 mol propylene oxide was introduced into the reactor, reacted for 5 h, and then with the help of nitrogen gas at the pressure of 0.8 MPa 21 mol ethylene oxide was introduced into the reactor, reacted for 5 h to obtain an ether product. The whole amount of the ether product was dissolved in absolute ethanol and formulated into a 40% solution and then added to a reactor, with the help of nitrogen gas at the pressure of 0.8 MPa, there was added 2.2 mol allyl chloride as the quaternizing agent. The reaction system was heated to a temperature of 80 degrees Celsius and then reacted for 3-10 h, depressurized to remove excessive allyl chloride as the quaternizing agent and ethanol as the solvent to obtain a quaternized product. Then 1 mol of the quaternized product, 20 L benzene as the solvent and 2.2 mol KOH were introduced into a reactor, heated to a temperature of 80 degrees Celsius, continuously stirred, water generated from the reaction system was distilled away under azeotropy until the quaternized product was converted into the corresponding potassium alkoxide. 2.2 mol sodium chloroacetate as the carboxylating agent was introduced into the reactor, reacted for 5 h, and then, the resultant was adjusted with HCl to an acidic pH value, washed with a 15% NaCl aqueous solution twice, converted with a MgOH aqueous solution into the corresponding magnesium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 4 as 4-5, and the 1H NMR spectrum of which was listed in Table 8.

Example 30

2 mol 1-chloro-9-octadecene and 20 mol monoethanolamine were introduced into a reactor, heated to a temperature of 180 degrees Celsius, reacted for 5 h, and then, was purified by chromatography to obtain N-octadecenyl monoethanolamine. Then 1 mol N-octadecenyl monoethanolamine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 31 mol propylene oxide was introduced into the reactor, reacted for 5 h, and then with the help of nitrogen gas at the pressure of 0.8 MPa 11 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 2.2 mol chlorocyclohexane as the quaternizing agent. The reaction system was heated to a temperature of 80 degrees Celsius and then reacted for 3-10 h, depressurized to remove excessive chlorocyclohexane as the quaternizing agent and ethanol as the solvent to obtain a quaternized product. Then 1 mol of the quaternized product, 10 L benzene as the solvent and 2.2 mol KOH were introduced into a reactor, heated to a temperature of 80 degrees Celsius, continuously stirred, water generated from the reaction system was distilled away under azeotropy until the quaternized product was converted into the corresponding potassium alkoxide. 2.2 mol sodium chloroacetate as the carboxylating agent was introduced into the reactor, reacted for 5 h, and then, the resultant was adjusted with HCl to an acidic pH value, washed with a 15% NaBr aqueous solution twice, converted with a CaOH aqueous solution into the corresponding potassium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 4 as 4-6, and the 1H NMR spectrum of which was listed in Table 8.

Example 31

2 mol methyl laurate and 20 mol hydroxyethyl ethylenediamine were introduced into a reactor, heated to a temperature of 180 degrees Celsius, reacted for 5 h, and then, was purified by chromatography to obtain N-lauroyl —N'-hydroxyethyl ethylenediamine. Then 1 mol N-lauroyl —N'-hydroxyethyl ethylenediamine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 42 mol propylene oxide was introduced into the reactor, reacted for 5 h, and then with the help of nitrogen gas at the pressure of 0.8 MPa 17 mol ethylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 2.2 mol chlorocyclohexane as the quaternizing agent. The reaction system was heated to a temperature of 80 degrees Celsius and then reacted for 3-10 h, depressurized to remove excessive chlorocyclohexane as the quaternizing agent and ethanol as the solvent to obtain a quaternized product. Then 1 mol of the quaternized product, 20 L benzene as the solvent and 2.2 mol KOH were introduced into a reactor, heated to a temperature of 80 degrees Celsius, continuously stirred, water generated from the reaction system was distilled away under azeotropy until the quaternized product was converted into the corresponding potassium alkoxide. 2.2 mol sodium chloroacetate as the carboxylating agent was introduced into the reactor, reacted for 5 h, and then, the resultant was adjusted with HCl to an acidic pH value, washed with a 15% NaI aqueous solution twice, converted with a KOH aqueous solution into the corresponding potassium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 4 as 4-7, and the 1H NMR spectrum of which was listed in Table 8.

Example 32

2 mol methyl oleate and 20 mol hydroxyethyl ethylenediamine were introduced into a reactor, heated to a temperature of 180 degrees Celsius, reacted for 5 h, and then, was purified by chromatography to obtain N-oleoyl —N'-hydroxyethyl ethylenediamine. Then 1 mol N-oleoyl —N'-hydroxyethyl ethylenediamine and 0.1 mol KOH were introduced into a reactor, heated to a temperature of 80 degrees Celsius, depressurized to a vacuum degree of 0.9, stirred for 30 minutes to remove any volatile, the atmosphere in the reactor was replaced by nitrogen gas for 4 times, the pressure in the reactor was adjusted to 0.2 MPa. The reaction system was heated to a temperature of 220 degrees Celsius, with the help of nitrogen gas at the pressure of 0.8 MPa 2 mol propylene oxide was introduced into the reactor, reacted for 5 h, to obtain an ether product. The whole amount of the ether product was dissolved in absolute ethanol and formulated into a 40% solution and then added to a reactor, with the help of nitrogen gas at the pressure of 0.8 MPa, there was added 2.2 mol chloromethane as the quaternizing agent. The reaction system was heated to a temperature of 80 degrees Celsius and then reacted for 3-10 h, depressurized to remove excessive chloromethane as the quaternizing agent and ethanol as the solvent to obtain a quaternized product. Then 1 mol of the quaternized product, 10 L benzene as the solvent and 2.2 mol KOH were introduced into a reactor, heated to a temperature of 80 degrees Celsius, continuously stirred, water generated from the reaction system was distilled away under azeotropy until the quaternized product was converted into the corresponding potassium alkoxide. 2.2 mol chloromethyl sodium sulfonate as the sulfonating agent was introduced into the reactor, reacted for 5 h, and then, the resultant was adjusted with HCl to an acidic pH value, washed with a 15% NaCl aqueous solution twice, converted with a NaOH aqueous solution into the corresponding sodium salt. The resultant was dissolved in a massive amount of absolute ethanol, removing by filtration any inorganic salt in the resultant, the solvent was removed by vacuum distillation to obtain an anionic-cationic-nonionic surfactant, the chemical structure of which was listed in Table 4 as 4-8, and the 1H NMR spectrum of which was listed in Table 8.

Example 33

0.30 wt % of the anionic-cationic-nonionic surfactant produced in Example 19 and a 0.15 wt % aqueous solution of polyacrylamide (having a molecular weight of 26000000) were mixed till homogenous, to obtain a flooding fluid composition for tertiary oil recovery.

TABLE 1

Chemical structure of the anionic-cationic-nonionic surfactant

| Surfactant No. | Chemical structure of the anionic-cationic-nonionic surfactant |
|---|---|
| 1-1 | |
| 1-2 | |
| 1-3 | |
| 1-4 | |

TABLE 1-continued

Chemical structure of the anionic-cationic-nonionic surfactant

| Surfactant No. | Chemical structure of the anionic-cationic-nonionic surfactant |
|---|---|
| 1-5 | |
| 1-6 | |
| 1-7 | $\Sigma m = 11, \Sigma n = 27$ |
| 1-8 | $\Sigma n = 48$ |

TABLE 2

Chemical structure of the anionic-cationic-nonionic surfactant

| Surfactant No. | Chemical structure of the anionic-cationic-nonionic surfactant |
|---|---|
| 2-1 | |
| 2-2 | |

TABLE 2-continued
Chemical structure of the anionic-cationic-nonionic surfactant
| Surfactant No. | Chemical structure of the anionic-cationic-nonionic surfactant |
|---|---|
| 2-3 | 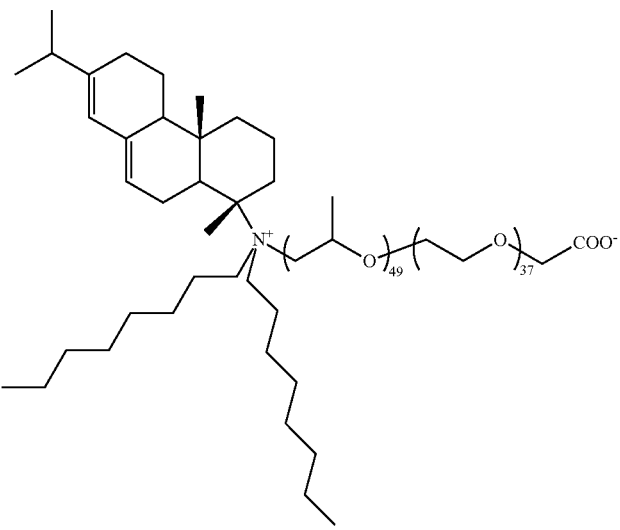 |
| 2-4 | 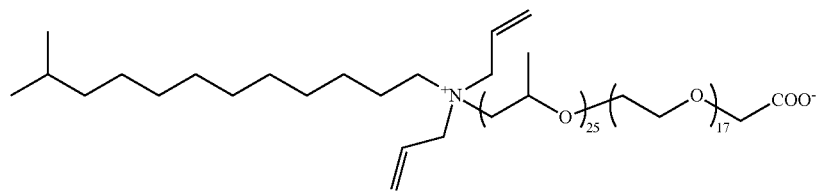 |
| 2-5 | 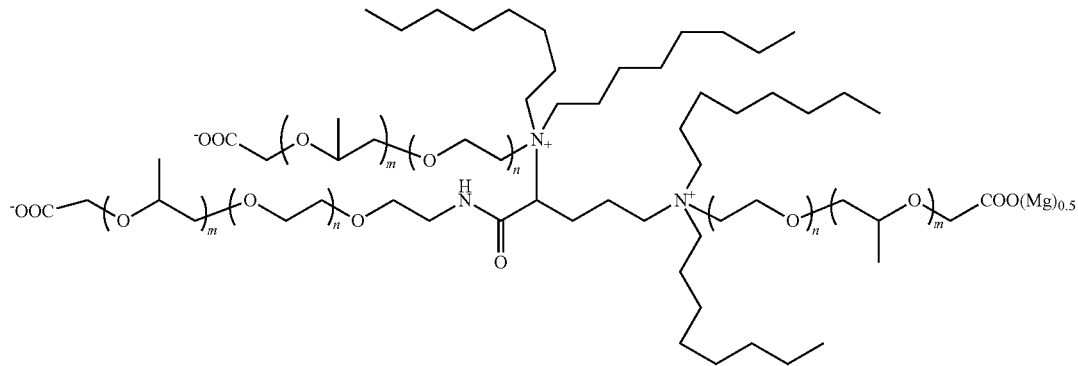 $\Sigma m = 15, \Sigma n = 39$ |
| 2-6 | 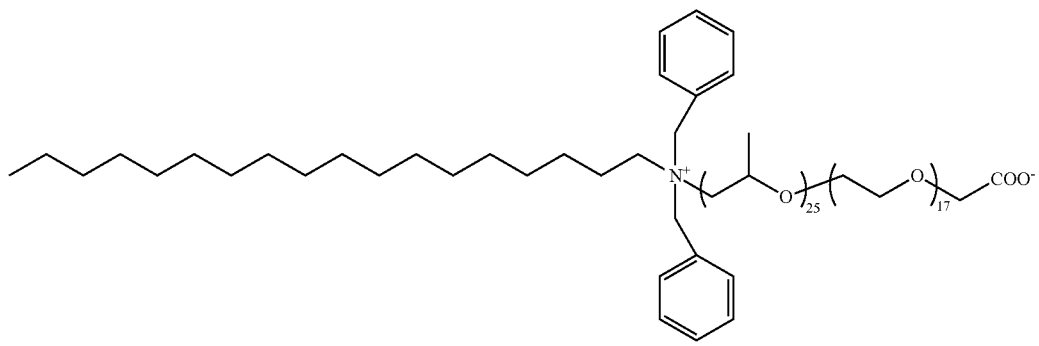 |

TABLE 2-continued
Chemical structure of the anionic-cationic-nonionic surfactant
| Surfactant No. | Chemical structure of the anionic-cationic-nonionic surfactant |
|---|---|
| 2-7 | 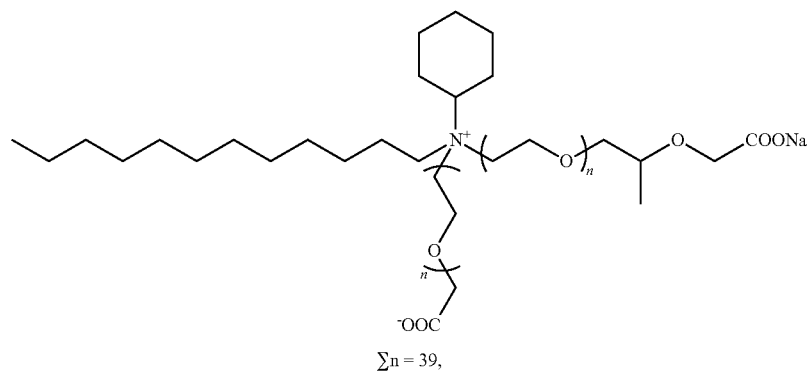 $\sum n = 39$, |
| 2-8 | 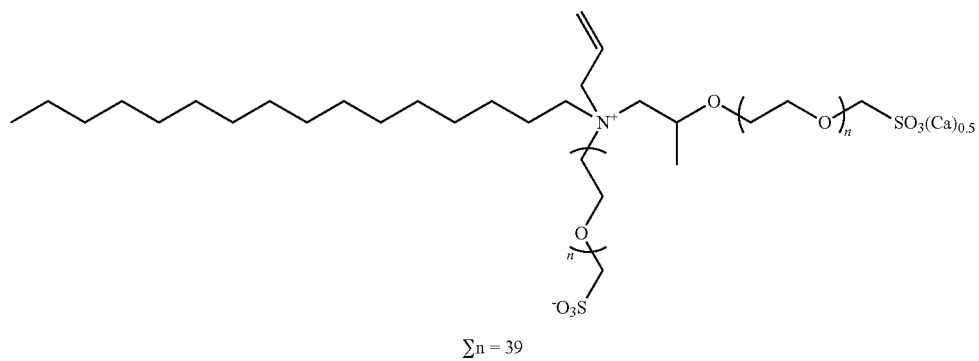 $\sum n = 39$ |
TABLE 3
Chemical structure of the anionic-cationic-nonionic surfactant
| Surfactant No. | Chemical structure of the anionic-cationic-nonionic surfactant |
|---|---|
| 3-1 |  |

TABLE 3-continued
Chemical structure of the anionic-cationic-nonionic surfactant
| Surfactant No. | Chemical structure of the anionic-cationic-nonionic surfactant |
|---|---|
| 3-2 | 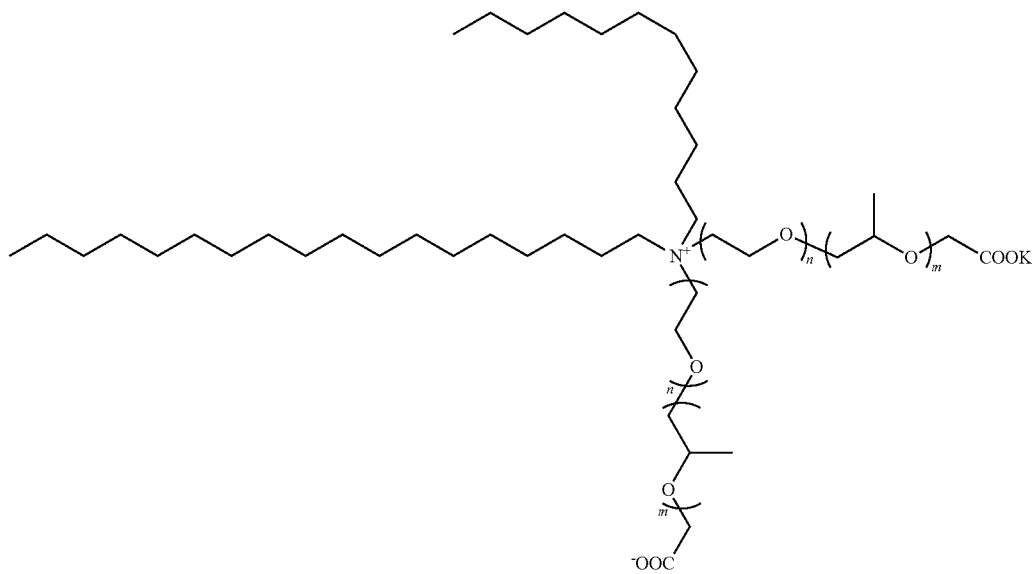 $\Sigma m = 22, \Sigma n = 6$ |
| 3-3 | 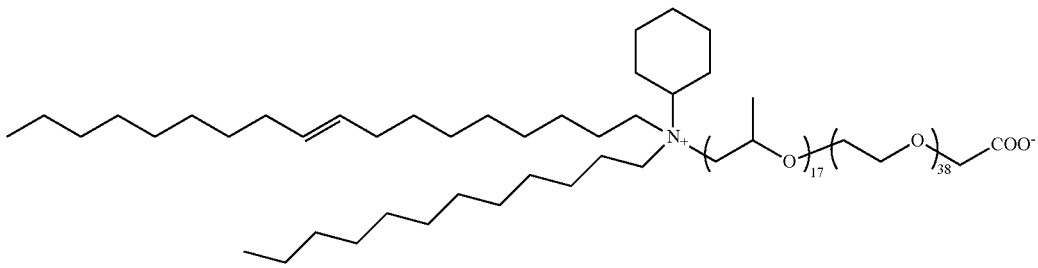 |
| 3-4 | 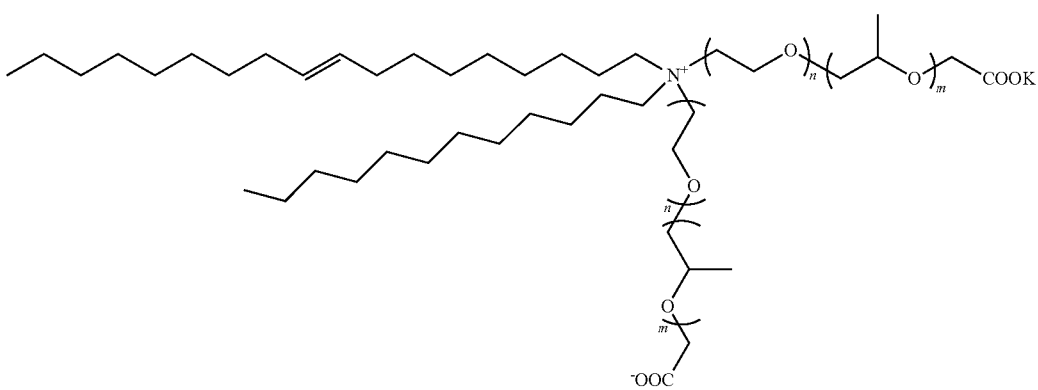 $\Sigma m = 49, \Sigma n = 18$ |

TABLE 3-continued
Chemical structure of the anionic-cationic-nonionic surfactant
| Surfactant No. | Chemical structure of the anionic-cationic-nonionic surfactant |
|---|---|
| 3-5 | 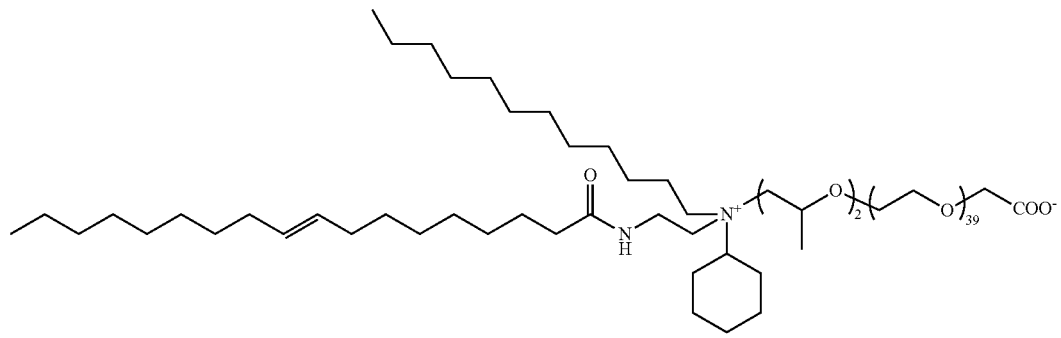<br>$\sum m = 2, \sum n = 39$ |
| 3-6 | 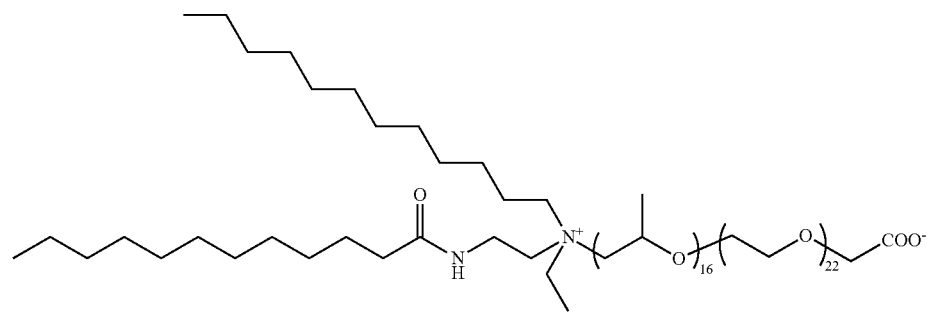 |
| 3-7 | 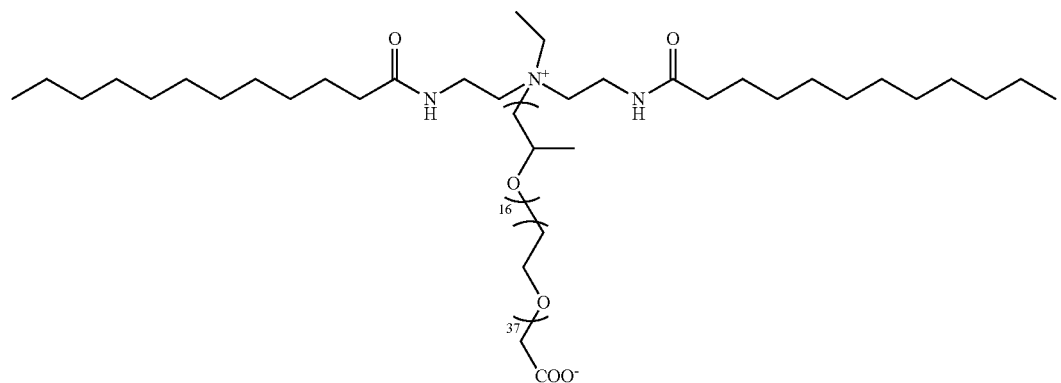 |
| 3-8 | 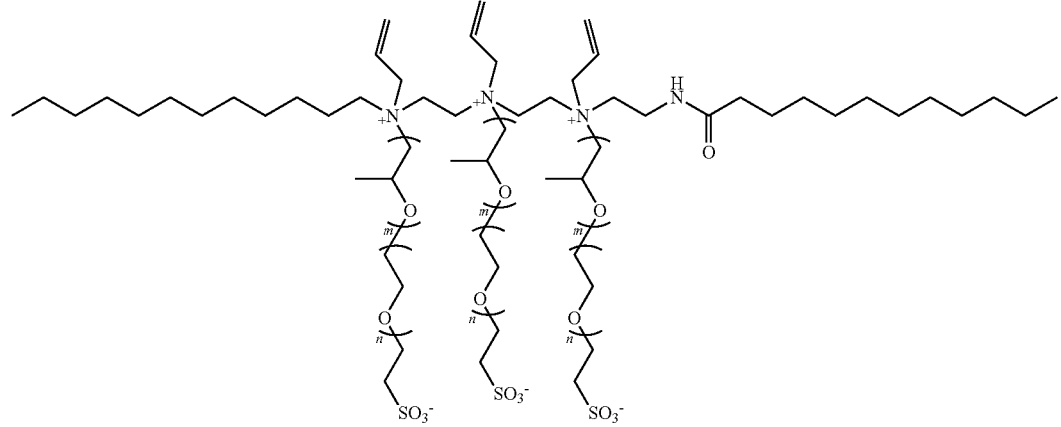<br>$\sum m = 31, \sum n = 9$ |

TABLE 4
Chemical structure of the anionic-cationic-nonionic surfactant
| Surfactant No. | Chemical structure of the anionic-cationic-nonionic surfactant |
|---|---|
| 4-1 | 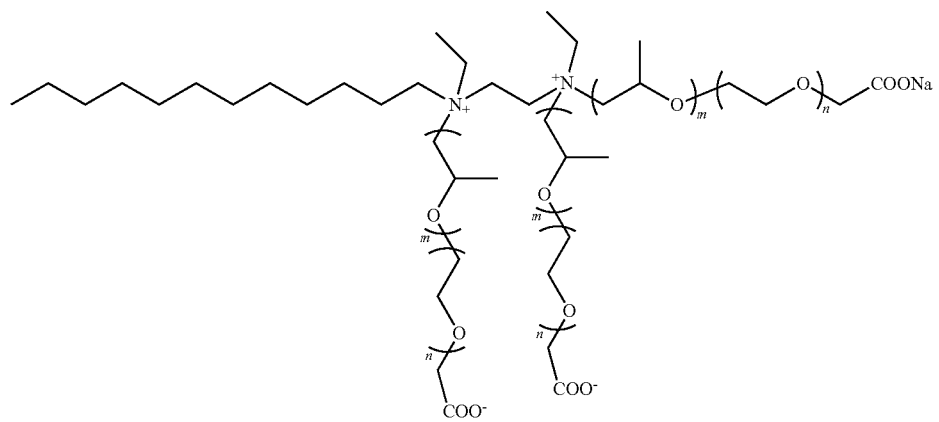
$\sum m = 23, \sum n = 19,$ |
| 4-2 | 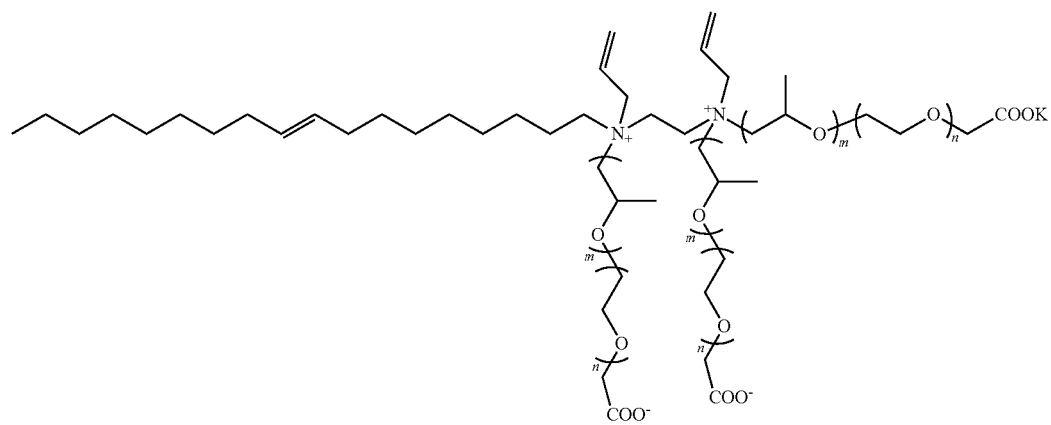
$\sum m = 11, \sum n = 9,$ |
| 4-3 | 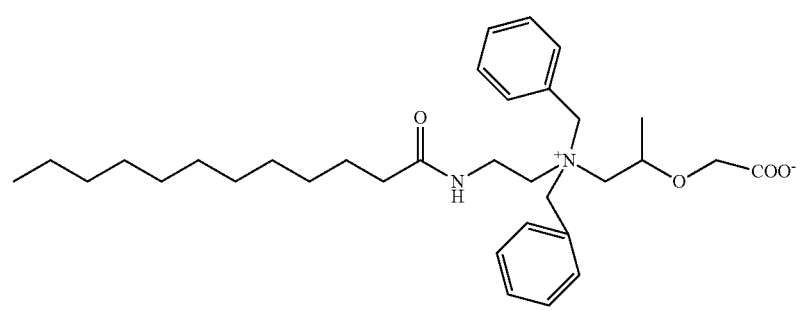 |

TABLE 4-continued
Chemical structure of the anionic-cationic-nonionic surfactant
| Surfactant No. | Chemical structure of the anionic-cationic-nonionic surfactant |
|---|---|
| 4-4 | 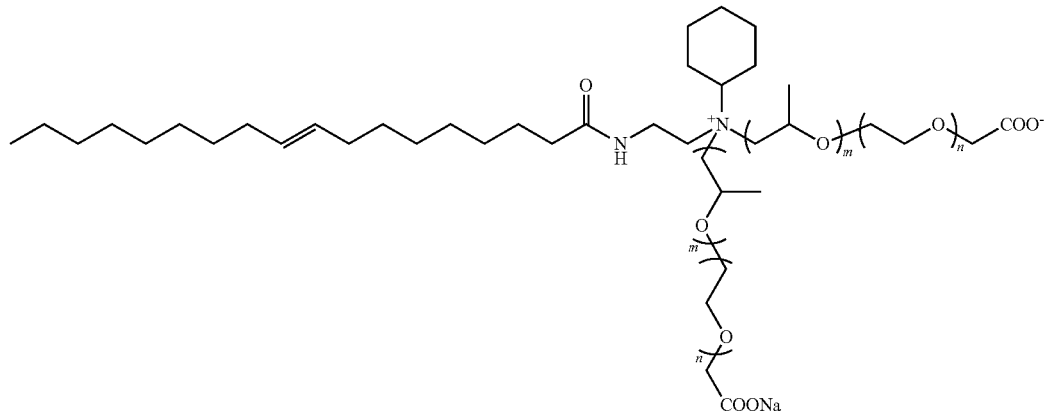<br>$\Sigma m = 47, \Sigma n = 32,$ |
| 4-5 | 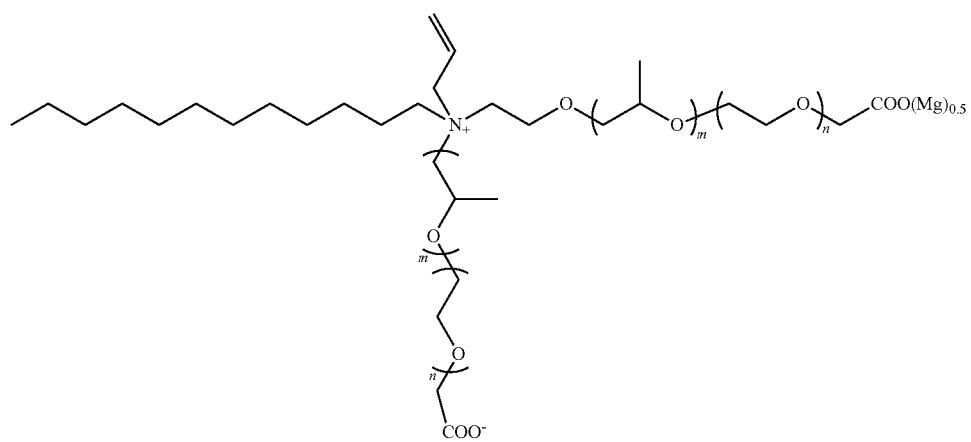<br>$\Sigma m = 41, \Sigma n = 21,$ |
| 4-6 | 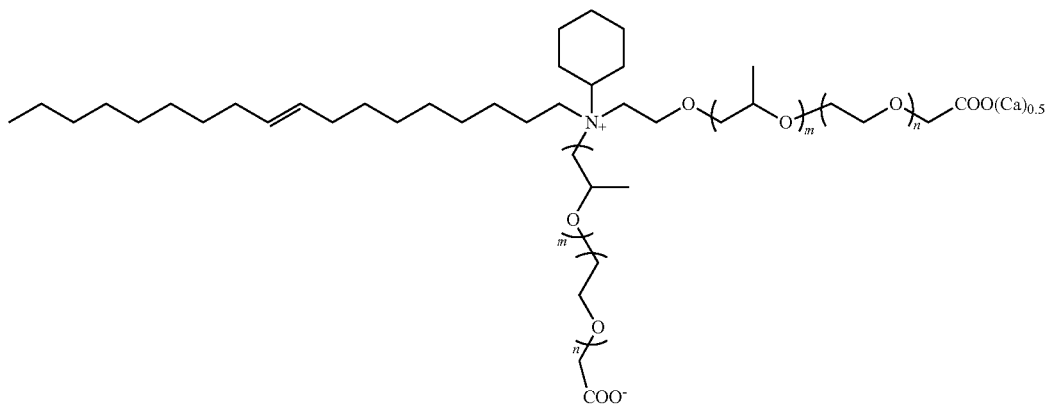<br>$\Sigma m = 31, \Sigma n = 11,$ |

TABLE 4-continued

Chemical structure of the anionic-cationic-nonionic surfactant

| Surfactant No. | Chemical structure of the anionic-cationic-nonionic surfactant |
|---|---|
| 4-7 | [Structure: dodecanoylamide-NH-CH₂CH₂-N⁺(cyclohexyl)(CH₂CH(CH₃)-O-branch)-CH₂CH₂-O-(CH(CH₃)CH₂O)ₘ-(CH₂CH₂O)ₙ-COOK; branch: -O-(CH(CH₃)CH₂O)ₘ-(CH₂CH₂O)ₙ-COO⁻] $\sum m = 42, \sum n = 17$ |
| 4-8 | [Structure: dodecanoylamide-NH-CH₂CH₂-N⁺(CH₃)(branch)-CH₂CH₂-O-CH(CH₃)CH₂-O-CH₂-SO₃Na; branch: -CH₂CH(CH₃)-O-CH₂-SO₃⁻] $\sum m = 2$ |

TABLE 5

The 1H NMR spectrum of the anionic-cationic-nonionic surfactant

| Surfactant No. | The peaks in the 1H NMR spectrum |
|---|---|
| 1-1 | 1H (300 MHz, CDCl₃, ppm): δ 7.48-7.9(m, 4H, Ar—H), 4.31(s, 2H, CH₂), 3.72(s, 6H, N—CH₃), 3.64(m, 1H, CH), 3.49(m, 1H, CH₂), 3.24(m, 1H, CH₂), 2.55(m, 2H, Ar—CH₂), 1.29-1.62(m, 18H, CH₂), 1.21(m, 3H, CH₃), 0.96(t, 3H, CH₃). |
| 1-2 | 1H (300 MHz, CDCl₃, ppm): δ 7.48-7.9(m, 4H, Ar—H), 4.31(s, 2H, CH₂—COONa), 3.72(s, 6H, N—CH₃), 3.41-3.81(m, 4H, CH₂), 2.55(m, 2H, Ar—CH₂), 1.29-1.62(m, 12H, CH₂), 0.96(t, 3H, CH₃). |
| 1-3 | 1H (300 MHz, CDCl₃, ppm): δ 7.48-7.9(m, 4H, Ar—H), 4.97-5.70(s, 8H, C=C—H), 4.33(s, 2H, CH₂—COONa), 3.91(m, 4H, CH₂), 3.54(m, 148H, CH₂), 2.55(m, 2H, Ar—CH₂), 1.29-1.62(m, 12H, CH₂), 1.21(m, 147H, CH₃), 0.96(t, 3H, CH₃). |
| 1-4 | 1H(300 MHz, CDCl₃, ppm): δ 7.48-7.9(m, 14H, Ar—H), 4.97-5.48(s, 2H, C=C—H), 4.5(s, 4H, CH₂), 4.33(s, 2H, CH₂—COONa), 3.63-3.64(m, 39H, CH₂, CH), 3.38(m, 38H, CH₂), 3.34(m, 38H, CH), 2.55(m, 2H, Ar—CH₂), 1.96(m, 4H, CH₂), 1.29-1.62(m, 22H, CH₂), 1.21(m, 117H, CH₃), 0.96(t, 3H, CH₃). |
| 1-5 | 1H (300 MHz, CDCl₃, ppm): δ 6.74(m, 3H, Ar—H), 4.5(s, 2H, CH₂), 4.33(s, 2H, CH₂—COONa), 3.79(m, 2H, CH₂), 3.54(m, 118H, CH₂, CH), 3.34(m, 38H, CH), 3.10(m, 1H, CH₂), 2.55(m, 2H, Ar—CH₂), 1.29-1.62(m, 22H, CH₂), 1.21(m, 117H, CH₃), 0.96(t, 3H, CH₃). |
| 1-6 | 1H (300 MHz, CDCl₃, ppm): δ 7.00-7.01(s, 4H, Ar—H), 4.5(d, 2H, CH₂), 4.48(s, 2H, CH₂—COONa), 3.63(m, 1H, CH₂), 3.54(m, 84H, CH₂), 3.38(m, 1H, CH₂, CH), 3.34(m, 1H, CH₂), 2.55(m, 2H, Ar—CH₂), 1.29-1.62(m, 14H, CH₂), 1.21(m, 51H, CH₃), 0.96(t, 3H, CH₃). |
| 1-7 | 1H (300 MHz, CDCl₃, ppm): δ 8.0 (s, 1H, CO—NH), 4.97-5.7(m, 3H, C=C—H), 4.48(s, 6H, CH₂—COONa), 3.91(d, 2H, N—CH₂—C=C), 3.64(m, 3H, CH), 3.63 (m, 9H, O—CH₂—C=), 3.38(m, 9H, CH₂), 3.34(m, 9H, CH), |

TABLE 5-continued

The 1H NMR spectrum of the anionic-cationic-nonionic surfactant

| Surfactant No. | The peaks in the 1H NMR spectrum |
|---|---|
|  | 3.54(m, 108H, O—CH$_2$), 3.45(m, 1H, C (O) —N—CH$_2$—C=), 3.49(m, 2H, N—CH$_2$—C=), 2.55(m, 2H, Ar—CH$_2$), 3.24(m, 2H, N—CH$_2$—C=), 3.20(m, 1H, C (O) —N—CH$_2$—C=), 1.29-1.62(m, 20H, CH$_2$), 1.21(m, 12H, =C—CH$_3$), 0.96(t, 3H, CH$_3$). |
| 1-8 | 1H (300 MHz, CDCl$_3$, ppm): δ 7.06-8.46(s, 13H, Ar—H), 4.5(m, 2H, N—CH$_2$—Ar), 5.49(s, 2H, CH$_2$—SO$_3$), 3.81(m, 4H, CH$_2$), 3.64(m, 2H, CH$_2$), 3.54(m, 164H, O—CH$_2$), 3.49(m, 4H, CH), 3.41(m, 4H, N—CH$_2$—CH$_2$—O), 2.55(m, 2H, Ar—CH$_2$), 1.29-1.62(m, 34H, CH$_2$), 1.21(m, 6H, =C—CH$_3$), 0.96(t, 3H, CH$_3$). |

TABLE 6

The 1H NMR spectrum of the anionic-cationic-nonionic surfactant

| Surfactant No. | The peaks in the 1H NMR spectrum |
|---|---|
| 2-1 | 1H (300 MHz, CDCl$_3$, ppm): δ 4.48 (s, 2H, CH$_2$—COONa), 3.64(m, 1H, CH), 3.49(m, 2H, CH$_2$), 3.3(m, 6H, CH$_2$), 1.29-1.73(m, 20H, CH$_2$), 1.21(m, 3H, CH$_3$), 0.96(t, 3H, CH$_3$) |
| 2-2 | 1H (300 MHz, CDCl$_3$, ppm): δ 5.48 (s, 2H,C=C—CH$_2$), 4.48(m, 2H, CH$_2$COONa), 3.81(m, 2H, CH$_2$), 3.3(m, 6H, CH$_2$), 1.96(m, 4H, CH$_2$), 1.29-1.73(m, 24H, CH$_2$), 0.96(t, 3H, CH$_3$) |
| 2-3 | 1H (300 MHz, CDCl$_3$, ppm): δ 5.50-5.70 (m, 2H,C=C—H), 4.33(m, 2H, CH$_2$COONa), 3.63(m, 48H, CH$_2$), 3.38(m, 48H, CH$_2$), 3.34(m, 49H, CH$_2$), 3.54(m, 118H, CH$_2$), 3.49(m, 2H, N—CH$_2$—C=), 2.06(m, 1H, CH), 1.91-2.04(m, 5H, C=C—CH$_2$, C=C—CH), 1.29-1.73(m, 18H, CH$_2$), 1.16(m, 3H, CH$_3$), 0.96(t, 3H, CH$_3$) |
| 2-4 | 1H (300 MHz, CDCl$_3$, ppm): δ 4.33 (s, 2H, CH$_2$—COONa), 3.64(m, 1H, CH), 3.63(m, 24H, CH$_2$), 3.38(m, 24H, CH$_2$), 3.34(m, 24H, CH), 3.54(m, 68H, CH$_2$), 3.49(m, 2H, CH$_2$), 3.24(m, 6H, CH$_2$), 1.29-1.77(m, 23H, CH$_2$), 0.96(t, 3H, CH$_3$) |
| 2-5 | 1H (300 MHz, CDCl$_3$, ppm): δ 4.31 (s, 6H, CH$_2$—COONa), 3.64(m, 1H, CH), 3.63(m, 15H, CH$_2$), 3.38(m, 15H, CH$_2$), 3.34(m, 15H, CH$_2$), 3.54(m, 145H, CH$_2$), 3.41(m, 4H, CH$_2$), 3.81(m, 4H, CH$_2$), 3.24(m, 6H, CH$_2$), 1.29-1.73(m, 30H, CH$_2$), 1.21(m, 3H, CH$_3$), 0.96(t, 3H, CH$_3$) |
| 2-6 | 1H (300 MHz, CDCl$_3$, ppm): δ 7.06-7.14 (m, 10H, Ar—H), 4.50(m, 4H, Ben-CH$_2$), 4.31(s, 2H, CH$_2$—COONa), 3.63-3.64(m, 25H, CH$_2$), 3.38(m, 24H, CH$_2$), 3.34(m, 24H, CH), 3.54(m, 68H, CH$_2$), 3.49(m, 2H, CH$_2$), 3.24(m, 6H, CH$_2$), 1.29-1.73(m, 32H, CH$_2$, CH), 1.21(m, 75H, CH$_3$), 0.96(t, 3H, CH$_3$) |
| 2-7 | 1H (300 MHz, CDCl$_3$, ppm): δ 4.48 (m, 2H, CH$_2$—COONa), 3.54(m, 156H, CH$_2$), 3.52(m, 2H, CH), 3.24(m, 4H, CH$_2$), 3.01(t, 1H, CH), 1.86(m, 2H, CH$_2$), 1.29-1.97(m, 40H, CH$_2$), 0.96(t, 3H, CH$_3$) |
| 2-8 | 1H (300 MHz, CDCl$_3$, ppm): δ 5.03-5.70 (m, 6H, C=C—H), 5.49(s, 2H, CH$_2$—SO$_3$), 3.91(m, 4H, CH$_2$), 3.54(m, 152H, CH$_2$), 3.24(m, 4H, CH$_2$), 3.01(t, 1H, CH), 1.29-1.97(m, 28H, CH$_2$), 1.21(m, 3H, CH$_3$), 0.96(t, 3H, CH$_3$) |

TABLE 7

The 1H NMR spectrum of the anionic-cationic-nonionic surfactant

| Surfactant No. | The peaks in the 1H NMR spectrum |
|---|---|
| 3-1 | 1H (300 MHz, CDCl$_3$, ppm): δ 4.31 (s, 2H,CH$_2$—COONa), 3.63(m, 20H, CH$_2$), 3.38(m, 20H, CH$_2$), 3.34(m, 24H, CH), 3.54(m, 68H, CH$_2$), 3.3(m, 2H, CH$_3$), 3.24(m, 6H, CH$_2$), 1.29-1.73(m, 40H, CH$_2$), 1.21(m, 22H, CH$_3$), 0.96(t, 3H, CH$_3$) |
| 3-2 | 1H (300 MHz, CDCl$_3$, ppm): δ 4.31 (s, 4H, CH$_2$—COONa), 3.81(m, 4H, CH$_2$), 3.63(m, 22H, CH$_2$), 3.38(m, 22H, CH$_2$), 3.34(m, 22H, CH), 3.54(m, 20H, CH$_2$), 3.41(m, 4H, CH$_2$), 1.29-1.73(m, 52H, CH$_2$), 1.21(m, 66H, CH$_3$), 0.96(t, 3H, CH$_3$) |
| 3-3 | 1H (300 MHz, CDCl$_3$, ppm): δ 4.31 (s, 2H, CH$_2$—COONa), 3.81(m, 2H, CH$_2$), 3.63(m, 17H, CH$_2$), 3.38(m, 17H, CH$_2$), 3.34(m, 17H, CH), 3.54(m, 148H, CH$_2$), 3.52(m, 1H, CH), 3.24(m, 4H, CH$_2$), 1.29-1.73(m, 44H, CH$_2$), 1.21(m, 34H, CH$_3$), 0.96(t, 6H, CH$_3$) |
| 3-4 | 1H (300 MHz, CDCl$_3$, ppm): δ 4.31 (s, 4H, CH$_2$—COONa), 3.63(m, 49H, CH$_2$), 3.38(m, 49H, CH$_2$), 3.34(m, 49H, CH), 3.54(m, 60H, CH$_2$), 3.41(m, 4H, CH), 3.24(m, 4H, CH$_2$), 1.29-1.73(m, 52H, CH$_2$), 1.21(m, 147H, CH$_3$), 0.96(t, 6H, CH$_3$) |

TABLE 7-continued

The 1H NMR spectrum of the anionic-cationic-nonionic surfactant

| Surfactant No. | The peaks in the 1H NMR spectrum |
|---|---|
| 3-5 | 1H (300 MHz, CDCl$_3$, ppm): δ 4.31 (s, 2H,CH$_2$—COONa), 3.64(m, 2H, CH$_2$), 3.63(m, 2H, CH$_2$), 3.54(m, 156H, CH$_2$), 3.52(m, 1H, CH), 3.5(m, 2H, CH$_2$), 3.49(m, 2H, CH$_2$), 3.38(m, 1H, CH$_2$), 3.34(m, 1H, CH), 3.24(m, 2H, CH$_2$), 1.29-1.73(m, 42H, CH$_2$), 1.21(m, 6H, CH$_3$), 0.96(t, 3H, CH$_3$) |
| 3-6 | 1H (300 MHz, CDCl$_3$, ppm): δ 4.31 (s, 2H, CH$_2$—COONa), 3.64(m, 2H, CH$_2$), 3.63(m, 15H, CH$_2$), 3.38(m, 15H, CH$_2$), 3.34(m, 16H, CH), 3.54(m, 88H, CH$_2$), 3.5(m, 2H, CH$_2$), 3.49(m, 2H, CH$_2$), 3.24(m, 4H, CH$_2$), 2.18(t, 2H, CH$_2$), 1.29-1.73(m, 38H, CH$_2$), 1.25(t, 3H, CH$_3$), 1.21(m, 48H, CH$_3$), 0.96(t, 6H, CH$_3$) |
| 3-7 | 1H (300 MHz, CDCl$_3$, ppm): δ 4.48 (s, 2H, CH$_2$—COONa), 3.64(m, 2H, CH$_2$), 3.63(m, 15H, CH$_2$), 3.38(m, 15H, CH$_2$), 3.34(m, 16H, CH), 3.54(m, 148H, CH$_2$), 3.5(m, 2H, CH$_2$), 3.49(m, 2H, CH$_2$), 3.24(m, 4H, CH$_2$), 2.18(t, 4H, CH$_2$), 1.29-1.73(m, 36H, CH$_2$), 1.25(t, 3H, CH$_3$), 1.21(m, 48H, CH$_3$), 0.96(t, 6H, CH$_3$) |
| 3-8 | 1H (300 MHz, CDCl$_3$, ppm): δ 5.49 (s, 4H, CH$_2$—COONa), 4.97(m, 2H, C=C—H), 5.03(m, 2H, C=C—H), 5.70(m, 2H, C=C—H), 3.64(m, 4H, CH$_2$), 3.63(m, 29H, CH$_2$), 3.38(m, 29H, CH$_2$), 3.34(m, 31H, CH), 3.54(m, 36H, CH$_2$), 3.5(m, 4H, CH$_2$), 3.49(m, 2H, CH$_2$), 3.24(m, 2H, CH$_2$), 2.18(t, 4H, CH$_2$), 1.29-1.73(m, 38H, CH$_2$), 1.21(m, 93H, CH$_3$), 0.96(t, 6H, CH$_3$) |

TABLE 8

The 1H NMR spectrum of the anionic-cationic-nonionic surfactant

| Surfactant No. | The peaks in the 1H NMR spectrum |
|---|---|
| 4-1 | 1H (300 MHz, CDCl$_3$, ppm): δ 4.31 (s, 6H, CH$_2$—COONa), 3.63(m, 21H, CH$_2$), 3.49(m, 2H, CH$_2$), 3.38(m, 21H, CH$_2$), 3.34(m, 21H, CH), 3.54(m, 76H, CH$_2$), 3.24(m, 2H, CH$_2$), 1.29-1.73(m, 20H, CH$_2$), 1.25(t, 3H, CH$_3$), 1.21(m, 69H, CH$_3$), 0.96(t, 3H, CH$_3$) |
| 4-2 | 1H (300 MHz, CDCl$_3$, ppm): δ 5.48 (m, 2H, C=C—H), 4.31 (s, 6H, CH$_2$—COONa), 3.64(m, 3H, CH), 3.63(m, 8H, CH$_2$), 3.49(m, 3H, CH$_2$), 3.38(m, 8H, CH$_2$), 3.34(m, 8H, CH), 3.54(m, 36H, CH$_2$), 3.24(m, 3H, CH$_2$), 1.96(m, 4H, CH$_2$), 1.29-1.73(m, 24H, CH$_2$), 1.25(t, 6H, CH$_3$), 1.21(m, 33H, CH$_3$), 0.96(t, 3H, CH$_3$) |
| 4-3 | 1H (300 MHz, CDCl$_3$, ppm): δ 8.0 (m, 1H, C(O)N—H), 7.06-7.14(m, 10H, Ar—H), 4.5(m, 2H, CH$_2$), 4.48 (s, 2H, CH$_2$—COONa), 3.64(t, 2H, CH$_2$), 3.49(d, 1H, CH$_2$), 3.5(t, 2H, CH$_2$), 3.24(d, 1H, CH$_2$), 2.18(t, 2H, CH$_2$), 1.29-1.73(m, 18H, CH$_2$), 1.21(m, 3H, CH$_3$), 0.96(t, 3H, CH$_3$) |
| 4-4 | 1H (300 MHz, CDCl$_3$, ppm): δ 4.31(s, 4H, CH$_2$—COONa), 3.64(m, 2H, CH$_2$), 3.63(m, 45H, CH$_2$), 3.5(t, 2H, CH$_2$), 3.49(t, 2H, CH$_2$), 3.38(m, 45H, CH$_2$), 3.34(m, 47H, CH), 3.24(d, 2H, CH$_2$), 2.18(t, 2H, CH$_2$), 1.29-1.73(m, 36H, CH$_2$), 1.21(m, 141H, CH$_3$), 0.96(t, 3H, CH$_3$) |
| 4-5 | 1H (300 MHz, CDCl$_3$, ppm): δ 4.97-5.7(m, 3H, C=C—H), 4.31 (s, 2H, CH$_2$—COONa), 3.91(m, 2H, CH$_2$), 3.81(m, 2H, CH$_2$), 3.64(m, 1H, CH$_2$), 3.63(m, 40H, CH$_2$), 3.49(m, 1H, CH$_2$), 3.38(m, 40H, CH$_2$), 3.34(m, 40H, CH), 3.54(m, 84H, CH$_2$), 3.24(m, 3H, CH$_2$), 1.29-1.73(m, 20H, CH$_2$), 1.21(m, 123H, CH$_3$), 0.96(t, 3H, CH$_3$) |
| 4-6 | 1H (300 MHz, CDCl$_3$, ppm): δ 5.48(m, 2H, C=C—H), 4.31(s, 4H, CH$_2$—COONa), 3.64(m, 2H, CH$_2$), 3.63(m, 29H, CH$_2$), 3.49(m, 2H, CH$_2$), 3.38(m, 29H, CH$_2$), 3.34(m,31H, CH), 3.54(m, 44H, CH$_2$), 3.24(m, 2H, CH$_2$), 1.29-1.73(m, 42H, CH$_2$), 1.21(m, 93H, CH$_3$), 0.96(t, 3H, CH$_3$) |
| 4-7 | 1H (300 MHz, CDCl$_3$, ppm): δ 8.0 (m, 1H, C(O)N—H), 5.48(m, 2H, C=C—H), 4.31(s, 4H, CH$_2$), 3.64(t, 2H, CH$_2$), 3.63(m, 40H, CH$_2$), 3.54(m, 68H, CH$_2$), 3.52(m, 1H, CH), 3.49(d, 2H, CH$_2$), 3.38(m, 40H, CH$_2$), 3.34(m, 42H, CH$_2$), 3.24(d, 2H, CH$_2$), 2.18(t, 2H, CH$_2$), 1.29-1.73(m, 28H, CH$_2$), 1.21(m, 126H, CH$_3$), 0.96(t, 3H, CH$_3$) |
| 4-8 | 1H (300 MHz, CDCl$_3$, ppm): δ 5.49(m, 2H, CH$_2$—SO$_3$), 3.81(m, 2H, CH$_2$), 3.64(m, 3H, CH$_2$, CH), 3.50(m, 2H, CH$_2$), 3.49(m, 1H, CH$_2$), 3.41(m, 2H, CH$_2$), 3.24(m, 1H, CH$_2$), 3.3(s, 3H, CH$_3$), 2.18(m, 2H, CH$_2$), 1.29-1.73(m, 26H, CH$_2$), 1.21(m, 3H, CH$_3$), 0.96(t, 3H, CH$_3$) |

Example 34 Interfacial Activity Test of the Surfactant

A TX-500C type spinning drop interfacial tensiometer was used to identify the oil-water interfacial tension between each surfactant and the IV5-11 reservoir crude oil from the Henan Shuanghe Oilfield, at a surfactant concentration of 0.3 wt %, with a test temperature of 81 degrees Celsius, a formation water of NaHCO$_3$ type, a TDS of 7947 mg/L, a chloride ion content of 2002 mg/L, a Ca$^{2+}$ content of 20 mg/L, a Mg$^{2+}$ content of 12.2 mg/L.

TABLE 9

The oil-water interfacial tension between the surfactant and the IV5-11 reservoir crude oil from the Henan Shuanghe Oilfield

| Example No. | Interfacial tension (mN/m) |
|---|---|
| 1 | 0.01 |
| 2 | 0.02 |
| 3 | 0.0006 |
| 4 | 0.0004 |
| 5 | 0.0007 |
| 6 | 0.004 |
| 7 | 0.0007 |
| 8 | 0.0006 |
| 9 | 0.009 |
| 10 | 0.0009 |
| 11 | 0.0004 |
| 12 | 0.0005 |
| 13 | 0.0006 |
| 14 | 0.0007 |
| 15 | 0.005 |
| 16 | 0.0007 |
| 17 | 0.0004 |
| 18 | 0.005 |
| 19 | 0.0003 |
| 20 | 0.006 |
| 21 | 0.0007 |
| 22 | 0.0005 |
| 23 | 0.0006 |
| 24 | 0.0007 |
| 25 | 0.0006 |
| 26 | 0.0004 |
| 27 | 0.04 |
| 28 | 0.0008 |
| 29 | 0.0007 |
| 30 | 0.0006 |
| 31 | 0.0005 |
| 32 | 0.08 |
| 33 | 0.0003 |

As can be seen from Table 9, the surfactant produced by each Example (except for Examples 1, 2, 27 and 32) exhibits a desirable interfacial activity with the crude oil from the Henan Oilfield. Example 33 reveals that, the surfactant produced according to this invention, even after compounded with a polymer, still exhibits a desirable interfacial activity.

The surfactant produced by Example 33 was formulated into different concentrations, each was tested the oil-water interfacial tension with the IV5-11 reservoir crude oil from the Henan Shuanghe Oilfield. The results were listed in Table 10.

TABLE 10

The oil-water interfacial tension between the surfactant 19 (at different concentrations) and the IV5-11 reservoir crude oil from the Henan Shuanghe Oilfield

| | Surfactant concentration (wt %) | | | | | |
|---|---|---|---|---|---|---|
| | 0.01 | 0.02 | 0.05 | 0.1 | 0.2 | 0.3 |
| Interfacial tension (mN/m) | 0.006 | 0.003 | 0.0009 | 0.0004 | 0.0003 | 0.0003 |

These results reveals that, the surfactant of this invention exhibits a relatively higher oil-water interfacial activity for the crude oil from the Henan Oilfield.

A TX-500C type spinning drop interfacial tensiometer was used to further identify the oil-water interfacial tension between the surfactant produced by each of Examples 1 to 4 and a crude oil from the third oil plant of the Zhongyuan Oilfield, with a test temperature of 80 degrees Celsius, a formation water with a TDS of 79439 mg/L, a $Ca^{2+}$ content of 592 mg/L, a $Mg^{2+}$ content of 2871 mg/L, a surfactant concentration of 0.3 wt %. The oil-water interfacial tension was observed as low as 0.003 mN/m. This reveals that the surfactant of this invention is widely applicable, not only to a reservoir with a low TDS, but also to a reservoir at elevated temperatures and with high salinity, by showing a desirable interfacial activity.

Example 35 Oil Washing Capability Test of the Surfactant

The IV5-11 reservoir oil sand from the Henan Shuanghe Oilfield at an oil:sand ratio of 1:4 (by weight) was aged at 81 degrees Celsius for 7 days, stirred for 5 minutes per 2 hours. Then 5 g of the thus aged oil sand and a 0.3 wt % solution of the surfactant at an oil sand:solution ratio of 1:10 (by weight) were mixed till homogenous, aged at the reservoir temperature for 48 h, then any crude oil in the solution was extracted with petroleum ether, adjusted with a 50 ml colorimetric tube to a metered volume, colorimetric analysed with a spectrophotometer at a wavelength of 430 nm. The concentration of crude oil in the surfactant solution was calculated by referring to the standard curve.

TABLE 11

The oil washing performance of the surfactant

| Example No. | Oil washing rate % |
|---|---|
| 1 | 39% |
| 2 | 31% |
| 3 | 68% |
| 4 | 77% |
| 5 | 66% |
| 6 | 51% |
| 7 | 65% |
| 8 | 67% |
| 9 | 49% |
| 10 | 61% |
| 11 | 73% |
| 12 | 71% |
| 13 | 66% |
| 14 | 64% |
| 15 | 49% |
| 16 | 65% |
| 17 | 73% |
| 18 | 46% |
| 19 | 81% |
| 20 | 48% |
| 21 | 63% |
| 22 | 73% |
| 23 | 67% |
| 24 | 66% |
| 25 | 69% |
| 26 | 78% |
| 27 | 28% |
| 28 | 60% |
| 29 | 63% |
| 30 | 66% |
| 31 | 74% |
| 32 | 25% |
| 33 | 81% |

Example 36 Study on the Oil Displacement Performance of the Surfactant

The oil displacement test was performed on a corestone having a length of 30 cm, a diameter of 2.5 cm and a permeability of 1.5 μm². The corestone was firstly displaced by the IV5-11 reservoir formation water from the Henan Shuanghe Oilfield till no crude oil was found in the effluent, then by a 0.3PV (the pore volume of the corestone) of the surfactant, then by water till no crude oil was found in the effluent. The results were listed in Table 7.

TABLE 12

Oil displacement results of the surfactant

| Example No. | Oil recovery increased by % |
|---|---|
| 1 | 2.8% |
| 2 | 2.5% |
| 3 | 4.9% |
| 4 | 8.9% |
| 5 | 4.7% |
| 6 | 4.1% |
| 7 | 5.5% |
| 8 | 5.6% |
| 9 | 4.0% |
| 10 | 5.0% |
| 11 | 7.5% |
| 12 | 7.1% |
| 13 | 6.7% |
| 14 | 6.4% |
| 15 | 4.0% |
| 16 | 6.5% |
| 17 | 7.1% |
| 18 | 4.2% |
| 19 | 9.7% |
| 20 | 4.1% |
| 21 | 6.4% |
| 22 | 7.0% |
| 23 | 5.6% |
| 24 | 6.7% |
| 25 | 6.9% |
| 26 | 9.0% |
| 27 | 1.8% |
| 28 | 6.1% |
| 29 | 6.5% |
| 30 | 6.8% |
| 31 | 7.2% |
| 32 | 1.2% |
| 33 | 10.9% |

Example 37 Study on the Long Term Stability of the Surfactant

Each surfactant produced in Examples was formulated into a 0.3 wt % solution with the IV5-11 reservoir formation water from the Henan Shuanghe Oilfield, placed into a thermostat oven, at 81 degrees Celsius aged for 1 day, 1 month, 2 months, 3 months respectively, and then taken out from the thermostat oven, with the appearance of the solution observed and the interfacial tension of the solution tested. A TX-500C type spinning drop interfacial tensiometer was used to identify the oil-water interfacial tension between each surfactant and the IV5-11 reservoir crude oil from the Henan Shuanghe Oilfield, with a test temperature of 81 degrees Celsius, a formation water of $NaHCO_3$ type, a TDS of 7947 mg/L, a chloride ion content of 2002 mg/L, a $Ca^{2+}$ content of 20 mg/L, a $Mg^{2+}$ content of 12.2 mg/L. The results were listed in Table 13, wherein the interfacial tension has a unit of mN/m.

TABLE 13

Long term stability results of the surfactant

| Example No. | 1 day | 1 month | 2 months | 3 months |
|---|---|---|---|---|
| 1 | clear and transparent, 0.01 | clear and transparent, 0.01 | clear and transparent, 0.02 | clear and transparent, 0.02 |
| 2 | clear and transparent, 0.02 | clear and transparent, 0.02 | clear and transparent, 0.04 | clear and transparent, 0.04 |
| 3 | clear and transparent, 0.0006 | clear and transparent, 0.0007 | clear and transparent, 0.0007 | clear and transparent, 0.0007 |
| 4 | clear and transparent, 0.0004 | clear and transparent, 0.0004 | clear and transparent, 0.0004 | clear and transparent, 0.0005 |
| 5 | clear and transparent, 0.0007 | clear and transparent, 0.0007 | clear and transparent, 0.0007 | clear and transparent, 0.0008 |
| 6 | clear and transparent, 0.004 | clear and transparent, 0.005 | clear and transparent, 0.006 | clear and transparent, 0.007 |
| 7 | clear and transparent, 0.0007 | clear and transparent, 0.005 | clear and transparent, 0.01 | clear and transparent, 0.1 |
| 8 | clear and transparent, 0.0006 | clear and transparent, 0.0006 | clear and transparent, 0.0006 | clear and transparent 0.0007 |
| 9 | clear and transparent, 0.009 | clear and transparent, 0.009 | clear and transparent, 0.01 | clear and transparent, 0.01 |
| 10 | clear and transparent, 0.0009 | clear and transparent, 0.001 | clear and transparent 0.002 | clear and transparent, 0.003 |
| 11 | clear and transparent, 0.0004 | clear and transparent, 0.0007 | clear and transparent, 0.0009 | clear and transparent 0.001 |
| 12 | clear and transparent, 0.0005 | clear and transparent, 0.0005 | clear and transparent, 0.0006 | clear and transparent, 0.0007 |
| 13 | clear and transparent, 0.0006 | clear and transparent, 0.009 | clear and transparent 0.01 | clear and transparent 0.015 |
| 14 | clear and transparent, 0.0007 | clear and transparent, 0.0007 | clear and transparent, 0.0007 | clear and transparent, 0.0008 |
| 15 | clear and transparent, 0.005 | clear and transparent, 0.005 | clear and transparent, 0.006 | clear and transparent, 0.007 |
| 16 | clear and transparent, 0.0007 | clear and transparent, 0.0009 | clear and transparent, 0.0011 | clear and transparent, 0.0014 |
| 17 | clear and transparent, 0.0004 | clear and transparent, 0.0004 | clear and transparent, 0.0005 | clear and transparent, 0.0005 |
| 18 | clear and transparent, 0.005 | clear and transparent, 0.008 | clear and transparent, 0.009 | clear and transparent, 0.009 |
| 19 | clear and transparent, 0.0003 | clear and transparent, 0.0003 | clear and transparent, 0.0004 | clear and transparent, 0.0004 |
| 20 | clear and transparent, 0.006 | clear and transparent, 0.007 | clear and transparent, 0.007 | clear and transparent, 0.01 |
| 21 | clear and transparent, 0.0007 | clear and transparent, 0.002 | clear and transparent 0.003 | clear and transparent, 0.01 |
| 22 | clear and transparent, 0.0005 | clear and transparent, 0.004 | clear and transparent, 0.005 | clear and transparent, 0.009 |
| 23 | clear and transparent, 0.0006 | clear and transparent, 0.002 | clear and transparent, 0.004 | clear and transparent, 0.005 |
| 24 | clear and transparent, 0.0007 | clear and transparent, 0.001 | clear and transparent, 0.003 | clear and transparent, 0.0 7 |
| 25 | clear and transparent, 0.0006 | clear and transparent, 0.0008 | clear and transparent, 0.0008 | clear and transparent, 0.0009 |
| 26 | clear and transparent, 0.0004 | clear and transparent, 0.0006 | clear and transparent, 0.0007 | clear and transparent, 0.0007 |
| 27 | clear and transparent, 0.04 | clear and transparent, 0.09 | clear and transparent, 0.1 | clear and transparent, 0.2 |

TABLE 13-continued

Long term stability results of the surfactant

| Example No. | 1 day | 1 month | 2 months | 3 months |
|---|---|---|---|---|
| 28 | clear and transparent, 0.0008 | clear and transparent, 0.0015 | clear and transparent, 0.003 | clear and transparent, 0.01 |
| 29 | clear and transparent, 0.0007 | clear and transparent, 0.0007 | clear and transparent, 0.0008 | clear and transparent, 0.0009 |
| 30 | clear and transparent, 0.0006 | clear and transparent, 0.0007 | clear and transparent, 0.0007 | clear and transparent, 0.0007 |
| 31 | clear and transparent, 0.0005 | clear and transparent, 0.009 | clear and transparent, 0.01 | clear and transparent, 0.02 |
| 32 | clear and transparent, 0.08 | clear and transparent, 0.2 | clear and transparent, 0.3 | clear and transparent, 0.5 |

As can be seen from these data that, the anionic-cationic-nonionic surfactant according to this invention, even at elevated temperatures, exhibits very well solubility in water, and preferably, even after stored for a long term, is excellent in terms of the interfacial activity stability.

Example 38 Study on the Chromatographic Fractionation of the Anionic-Cationic-Nonionic Surfactant Each surfactant produced in Examples was formulated into a 0.3 wt % solution with the IV5-11 reservoir formation water from the Henan Shuanghe Oilfield. A slimline model having an inner diameter of 0.4 cm and a length of 4.5 m was filled with the mixture of 30% IV5-11 reservoir oil sand from the Henan Shuanghe Oilfield and 70% quartz sand. With the mixed sand model, chromatographic fractionation experiments were conducted as follows: 1) (Experiment 1 #) injected thereto a 2PV of the formulated surfactant solution; 2) (Experiment 2 #) injected thereto a combination of the surfactant solution and an alkali (NaOH as the alkali at a concentration of 2000 mg/L); 3) (Experiment 3 #) firstly injected thereto a 1PV of a 2000 mg/l NaOH solution in the formation water, and then a combination of the surfactant solution and an alkali (NaOH as the alkali at a concentration of 2000 mg/L), with an injection flow velocity of 0.2 mL/min. After injected with a predetermined slug of the combination, the mixed sand model was displaced by the formation water at the same flow rate, and the effluent was collected. High performance liquid chromatography (HPLC) and total organic carbon analysis (TOC) were co-used to determine the change in the concentration of the surfactant in the effluent as the volume of the injected liquid changes. If the surfactant was fractionated into different components, each surfactant component was calculated respectively with its recovery yield on the basis of the amount injected and the amount collected according to the following formula.

$$\text{chromatographic fractionation factor} = \frac{\text{yield of a first surfactant component}}{\text{yield of a second surfactant component}}$$

If multiple surfactant components were identified, one of them was taken as the reference, and others were then compared with the reference. The results were listed in Table 14.

TABLE 14

Chromatographic fractionation results of the anionic-cationic-nonionic surfactant

| Example No. | Experiment 1# | Experiment 2# | Experiment 3# |
|---|---|---|---|
| 1 | components not fractionated, no chromatographic fractionation problem | components not fractionated, no chromatographic fractionation problem | components not fractionated, no chromatographic fractionation problem |
| 2 | components not fractionated, no chromatographic fractionation problem | components not fractionated, no chromatographic fractionation problem | components not fractionated, no chromatographic fractionation problem |
| 3 | components not fractionated, no chromatographic fractionation problem | components not fractionated, no chromatographic fractionation problem | components not fractionated, no chromatographic fractionation problem |
| 4 | components not fractionated, no chromatographic fractionation problem | components not fractionated, no chromatographic fractionation problem | components not fractionated, no chromatographic fractionation problem |
| 5 | components not fractionated, no chromatographic fractionation problem | components not fractionated, no chromatographic fractionation problem | components not fractionated, no chromatographic fractionation problem |
| 6 | components not fractionated, no chromatographic fractionation problem | components not fractionated, no chromatographic fractionation problem | components not fractionated, no chromatographic fractionation problem |
| 7 | components not fractionated, no chromatographic fractionation problem | components not fractionated, no chromatographic fractionation problem | components not fractionated, no chromatographic fractionation problem |
| 8 | components not fractionated, no chromatographic fractionation problem | components not fractionated, no chromatographic fractionation problem | components not fractionated, no chromatographic fractionation problem |

TABLE 14-continued

Chromatographic fractionation results of the anionic-cationic-nonionic surfactant

| Example No. | Experiment 1# | Experiment 2# | Experiment 3# |
|---|---|---|---|
| 9 | components not fractionated, no chromatographic fractionation problem | components not fractionated, no chromatographic fractionation problem | components not fractionated, no chromatographic fractionation problem |
| 10 | components not fractionated, no chromatographic fractionation problem | components not fractionated, no chromatographic fractionation problem | components not fractionated, no chromatographic fractionation problem |
| 11 | components not fractionated, no chromatographic fractionation problem | components not fractionated, no chromatographic fractionation problem | components not fractionated, no chromatographic fractionation problem |
| 12 | components not fractionated, no chromatographic fractionation problem | components not fractionated, no chromatographic fractionation problem | components not fractionated, no chromatographic fractionation problem |
| 13 | components not fractionated, no chromatographic fractionation problem | components not fractionated, no chromatographic fractionation problem | components not fractionated, no chromatographic fractionation problem |
| 14 | components not fractionated, no chromatographic fractionation problem | components not fractionated, no chromatographic fractionation problem | components not fractionated, no chromatographic fractionation problem |
| 15 | components not fractionated, no chromatographic fractionation problem | components not fractionated, no chromatographic fractionation problem | components not fractionated, no chromatographic fractionation problem |
| 16 | components not fractionated, no chromatographic fractionation problem | components not fractionated, no chromatographic fractionation problem | components not fractionated, no chromatographic fractionation problem |
| 17 | components not fractionated, no chromatographic fractionation problem | components not fractionated, no chromatographic fractionation problem | components not fractionated, no chromatographic fractionation problem |
| 18 | components not fractionated, no chromatographic fractionation problem | components not fractionated, no chromatographic fractionation problem | components not fractionated, no chromatographic fractionation problem |
| 19 | components not fractionated, no chromatographic fractionation problem | components not fractionated, no chromatographic fractionation problem | components not fractionated, no chromatographic fractionation problem |
| 20 | components not fractionated, no chromatographic fractionation problem | components not fractionated, no chromatographic fractionation problem | components not fractionated, no chromatographic fractionation problem |
| 21 | components not fractionated, no chromatographic fractionation problem | components not fractionated, no chromatographic fractionation problem | components not fractionated, no chromatographic fractionation problem |
| 22 | components not fractionated, no chromatographic fractionation problem | components not fractionated, no chromatographic fractionation problem | components not fractionated, no chromatographic fractionation problem |
| 23 | components not fractionated, no chromatographic fractionation problem | components not fractionated, no chromatographic fractionation problem | components not fractionated, no chromatographic fractionation problem |
| 24 | components not fractionated, no chromatographic fractionation problem | components not fractionated, no chromatographic fractionation problem | components not fractionated, no chromatographic fractionation problem |
| 25 | components not fractionated, no chromatographic fractionation problem | components not fractionated, no chromatographic fractionation problem | components not fractionated, no chromatographic fractionation problem |
| 26 | components not fractionated, no chromatographic fractionation problem | components not fractionated, no chromatographic fractionation problem | components not fractionated, no chromatographic fractionation problem |

TABLE 14-continued

Chromatographic fractionation results of the anionic-cationic-nonionic surfactant

| Example No. | Experiment 1# | Experiment 2# | Experiment 3# |
| --- | --- | --- | --- |
| 27 | components not fractionated, no chromatographic fractionation problem | components not fractionated, no chromatographic fractionation problem | components not fractionated, no chromatographic fractionation problem |
| 28 | components not fractionated, no chromatographic fractionation problem | components not fractionated, no chromatographic fractionation problem | components not fractionated, no chromatographic fractionation problem |
| 29 | components not fractionated, no chromatographic fractionation problem | components not fractionated, no chromatographic fractionation problem | components not fractionated, no chromatographic fractionation problem |
| 30 | components not fractionated, no chromatographic fractionation problem | components not fractionated, no chromatographic fractionation problem | components not fractionated, no chromatographic fractionation problem |
| 31 | components not fractionated, no chromatographic fractionation problem | components not fractionated, no chromatographic fractionation problem | components not fractionated, no chromatographic fractionation problem |
| 32 | components not fractionated, no chromatographic fractionation problem | components not fractionated, no chromatographic fractionation problem | components not fractionated, no chromatographic fractionation problem |

As can be seen from these test results, the anionic-cationic-nonionic surfactant according to this invention does not suffer from the chromatographic fractionation problem.

Comparative Example 1

According to the method proposed by Journal of Northwest University (Natural Science Edition), Gong Yujun et. al, Vol. 30 (1), pp. 28 to 31, February 2000, hexadecyl trimethyl ammonium bromide (CTAB) and sodium dodecyl sulfate (SDS) were formulated into a mixture at a ratio by molar of 1:1.5, and tested at a concentration of 0.3 wt % for its oil-water interfacial tension, oil washing rate and oil displacement performance with the IV5-11 reservoir crude oil from the Henan Shuanghe Oilfield. The results were listed as follows.

TABLE 15

The performances of the reference flooding fluid

| Interfacial tension (mN/m) | Oil washing rate % | Oil recovery increased by % |
| --- | --- | --- |
| 0.03 | 45.6 | 2.8 |

Comparative Example 2

According to the method proposed by Journal of Oil and Gas Technology, Huang Hongdu et. al, Vol. 29(4), August 2007 (pp. 101 to 104), 0.01 wt % hexadecyl trimethyl ammonium bromide, 0.02 wt % petroleum sulfonate salt as the anionic surfactant and 1.8 wt % $Na_2CO_3$ were formulated into a mixture, and tested at a concentration of 0.3 wt % for its oil-water interfacial tension, oil washing rate and oil displacement performance with the IV5-11 reservoir crude oil from the Henan Shuanghe Oilfield. The results were listed as follows.

TABLE 16

The performances of the reference flooding fluid

| Interfacial tension (mN/m) | Oil washing rate % | Oil recovery increased by % |
| --- | --- | --- |
| 0.008 | 56.3 | 4.2 |

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. An anionic-cationic-nonionic surfactant represented by formula (I-3) or formula (I-4), with the proviso that, at least one N atom contained in the molecular structure thereof bonds to Rh and X so as to form into a quaternary ammonium salt/hydroxide group represented by the formula

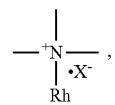

in which:
the group $N^+$ represents the at least one N atom in the form of quaternary nitrogen cation;
the group Rh represents a second optionally substituted $C_{5-50}$ monocyclic or polycyclic cycloalkyl, a second optionally substituted $C_{2-50}$ linear or branched alkenyl, or a second optionally substituted $C_{6-50}$ aryl; the group $X^-$ represents a halogen ion or hydroxide ion, and
wherein "second optionally substituted" refers to optionally substituted by one or more substituent selected from the group consisting of oxo, hydroxyl, a $C_{1-20}$ linear or branched alkyl, a $C_{5-10}$ monocyclic or polycyclic cycloalkyl, a $C_{2-20}$ linear or branched alkenyl, and a $C_{6-20}$ aryl, wherein, in formula (I-3):

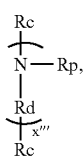
(I-3)

the plural group Rc is identical with or different from one another, each independently selected from the group consisting of a third optionally substituted $C_{8-20}$ linear or branched alkyl, a third optionally substituted $C_{8-20}$ linear or branched alkenyl, a third optionally substituted $C_{8-20}$ linear or branched alkyl carbonyl; and a third optionally substituted $C_{8-20}$ linear or branched alkenyl carbonyl;

the plural group Rd is identical with or different from one another, each independently selected from the group consisting of a third optionally substituted $C_{1-10}$ linear or branched alkylene, a third optionally substituted $C_{2-10}$ linear or branched alkenylene, a third optionally substituted $C_{1-10}$ linear or branched alkylene carbonyl, a third optionally substituted $C_{2-10}$ linear or branched alkenylene carbonyl, a third optionally substituted carbonyl $C_{1-10}$ linear or branched alkylene carbonyl, and a third optionally substituted carbonyl $C_{2-10}$ linear or branched alkenylene carbonyl;

the numerical value x''' represents 1;

the plural group Rp is identical with or different from one another, each independently selected from the group consisting of a group represented by the formula

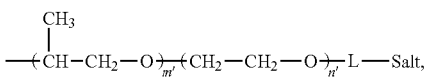

hydrogen, a third optionally substituted $C_{1-50}$ linear or branched alkyl, a third optionally substituted $C_{5-50}$ monocyclic or polycyclic cycloalkyl, a third optionally substituted $C_{2-50}$ linear or branched alkenyl and a third optionally substituted $C_{6-50}$ aryl, with the proviso that at least one of the groups Rp represents a group represented by the formula

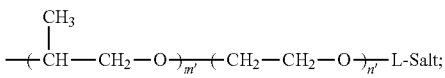

in which:

the plural numerical value m' is identical with or different from one another, each independently represents a value from 15 to 100, plural numerical value n' is identical with or different from one another, each independently represents a value from 0 to 35, with the proviso that the sum of all numerical values m' and all numerical values n' is greater than 0 but not greater than 100;

the plural group L is identical with or different from one another, each independently selected from the group consisting of a third optionally substituted $C_{1-10}$ linear or branched alkylene and a third optionally substituted $C_{2-10}$ linear or branched alkenylene, the plural group Salt is identical with or different from one another, each independently represents a group represented by the formula $-A^-(M)_r^+$, wherein the group A represents a carboxylate ion ($COO^-$) or a sulfonate ion ($SO_3^-$);

the group M represents alkali metal, alkaline earth metal or ammonium ($NH_4$), wherein when the group M represents alkali metal or ammonium, r=1; and when the group M represents alkaline earth metal, r=0.5, with the proviso that at least one of the plural group Rc comprises in molecular structure thereof a $C_8$ linear moiety, and the overall average number of the units $-O-CH_2-CH_2-$ and/or

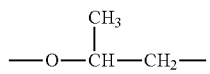

is 10.0 or more, wherein, in formula (I-4):

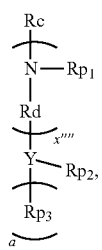
(I-4)

the plural group Rc represents a third optionally substituted $C_{1-20}$ linear or branched alkyl, a third optionally substituted $C_{2-20}$ linear or branched alkenyl, a third optionally substituted $C_{1-20}$ linear or branched alkyl carbonyl or a third optionally substituted $C_{2-20}$ linear or branched alkenyl carbonyl;

the plural group Rd is identical with or different from one another, each independently selected from the group consisting of a third optionally substituted $C_{1-10}$ linear or branched alkylene, a third optionally substituted $C_{2-10}$ linear or branched alkenylene, a third optionally substituted $C_{1-10}$ linear or branched alkylene carbonyl, a third optionally substituted $C_{2-10}$ linear or branched alkenylene carbonyl, a third optionally substituted carbonyl $C_{1-10}$ linear or branched alkylene carbonyl and a third optionally substituted carbonyl $C_{2-10}$ linear or branched alkenylene carbonyl; the group Y represents N or O, with the proviso that when the group Y represents N, a=1, when the group Y represents O, a=0;

the numerical value x'''' represents 1;

the plural group $Rp_1$ is identical with or different from one another, each independently selected from the group consisting of a group represented by the formula

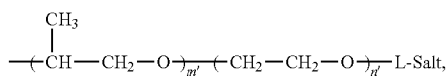

hydrogen, a third optionally substituted $C_{1-50}$ linear or branched alkyl, a third optionally substituted $C_{5-50}$ monocyclic or polycyclic cycloalkyl, a third optionally substituted $C_{2-50}$ linear or branched alkenyl and a third optionally substituted $C_{6-50}$ aryl, with the proviso that at least one of the groups $Rp_1$ represents a group represented by the formula

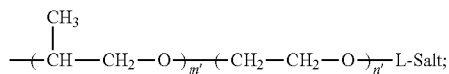

the plural group $Rp_2$ is identical with or different from one another, each independently is a group represented by the formula

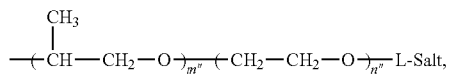

the plural group $Rp_3$ is identical with or different from one another, each independently is a group represented by the formula

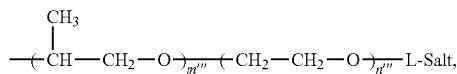

the plural numerical value m' is identical with or different from one another, each independently represents a value from 15 to 100, the plural numerical value n' is identical with or different from one another, each independently represents a value from 0 to 35, the plural numerical value m" is identical with or different from one another, each independently represents a value from 0.5 to 100, the plural numerical value n" is identical with or different from one another, each independently represents a value from 0 to 100, the plural numerical value m'" is identical with or different from one another, each independently represents a value from 0.5 to 100, the plural numerical value n'" is identical with or different from one another, each independently represents a value from 0 to 100, with the proviso that the sum of all numerical values m' and all numerical values m" and all numerical values m'" and all numerical values n' and all numerical values n" and all numerical values n'" is greater than 0 but not greater than 200;

wherein the plural group L is identical with or different from one another, each independently selected from the group consisting of a third optionally substituted $C_{1-10}$ linear or branched alkylene and a third optionally substituted $C_{2-10}$ linear or branched alkenylene, wherein the plural group Salt is identical with or different from one another, each independently represents a group represented by the formula $-A^-(M)_r^+$, wherein the group $A^-$ represents a carboxylate ion ($COO^-$) or a sulfonate ion ($SO_3^-$); the group M represents alkali metal, alkaline earth metal or ammonium ($NH_4$); wherein, when the group M represents alkali metal or ammonium, r=1; when the group M represents alkaline earth metal, r=0.5;

with the proviso that at least one of the plural group Rc and the plural group Rh comprises in molecular structure thereof a $C_8$ linear moiety, and the overall average number of the units $-O-CH_2-CH_2-$ and/or

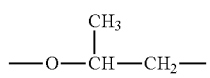

is 10.0 or more, wherein "third optionally substituted" refers to optionally substituted by one or more substituent selected from the group consisting of hydroxyl, a $C_{1-20}$ linear or branched alkyl, a $C_{5-10}$ monocyclic or polycyclic cycloalkyl, a $C_{2-20}$ linear or branched alkenyl, and a $C_{6-20}$ aryl.

2. The anionic-cationic-nonionic surfactant according to claim 1, wherein the numerical value m' is identical with or different from one another, each independently represents a value from 15 to 50, the plural numerical value n' is identical with or different from one another, each independently represents a value from 0 to 35, the plural numerical value m" is identical with or different from one another, each independently represents a value from 0.5 to 50, and the plural numerical value n" is identical with or different from one another, each independently represents a value from 0 to 50.

3. The anionic-cationic-nonionic surfactant according to claim 1, wherein throughout the molecular structure of the anionic-cationic-nonionic surfactant, assuming that a total number of the group $X^-$ is e1, a total number of the group $N^+$ is e2, a total number of the group $A^-$ is e3, a total number of the group $(M)_r^+$ is e4, when e2=e3, then 0≤e1≤e2, 0≤e4≤e3; or, when e2>e3, then 0<e1≤e2, 0≤e4≤e3; or, when e2<e3, then 0≤e1≤e2, 0<e4≤e3, with the proviso that e1+e3=e2+e4, or e2=e3, e1=0, and e4=0.

4. A flooding fluid composition for tertiary oil recovery, comprising an anionic-cationic-nonionic surfactant according to claim 1, and water, wherein the content of the anionic-cationic-nonionic surfactant is 0.001-10 wt %, relative to the total weight (as 100 wt %) of the flooding fluid composition for tertiary oil recovery.

5. The flooding fluid composition for tertiary oil recovery according to claim 4, comprising no inorganic alkali.

6. A tertiary oil recovery process, comprising a step of conducting tertiary oil recovery in the presence of the anionic-cationic-nonionic surfactant according to claim 1 as a flooding fluid.

7. The tertiary oil recovery process according to claim 6, wherein no inorganic alkali is used.

* * * * *